US010759821B2

(12) United States Patent
Swarts

(10) Patent No.: US 10,759,821 B2
(45) Date of Patent: Sep. 1, 2020

(54) TREHALOSE ANALOGUES

(71) Applicant: Central Michigan University, Mount Pleasant, MI (US)

(72) Inventor: Benjamin M. Swarts, Mount Pleasant, MI (US)

(73) Assignee: CENTRAL MICHIGAN UNIVERSITY, Mount Pleasant, MI (US)

( * ) Notice: Subject to any disclaimer, the term of this patent is extended or adjusted under 35 U.S.C. 154(b) by 0 days.

(21) Appl. No.: 15/701,084

(22) Filed: Sep. 11, 2017

(65) Prior Publication Data

US 2018/0072767 A1 Mar. 15, 2018

Related U.S. Application Data

(60) Provisional application No. 62/385,772, filed on Sep. 9, 2016, provisional application No. 62/411,999, filed on Oct. 24, 2016.

(51) Int. Cl.
| | |
|---|---|
| *C07H 7/06* | (2006.01) |
| *G01N 33/60* | (2006.01) |
| *C12Q 1/16* | (2006.01) |
| *G01N 33/58* | (2006.01) |
| *C12Q 1/04* | (2006.01) |

(52) U.S. Cl.
CPC .......... *C07H 7/06* (2013.01); *C12Q 1/04* (2013.01); *C12Q 1/16* (2013.01); *G01N 33/582* (2013.01); *G01N 33/60* (2013.01); *G01N 2333/35* (2013.01)

(58) Field of Classification Search
None
See application file for complete search history.

(56) References Cited

U.S. PATENT DOCUMENTS

| | | | |
|---|---|---|---|
| 2012/0263649 | A1 | 10/2012 | Backus et al. |
| 2013/0302857 | A1 | 11/2013 | Van Der Borght et al. |
| 2014/0051599 | A1* | 2/2014 | Gwenin .............. G01N 33/5695 506/9 |
| 2015/0125884 | A1 | 5/2015 | Budin et al. |
| 2015/0252402 | A1 | 9/2015 | Swarts et al. |

FOREIGN PATENT DOCUMENTS

| | | |
|---|---|---|
| WO | 2011030160 | 3/2011 |

OTHER PUBLICATIONS

Asensio et al. The Virulence-associated two-component PhoP-PhoR system controls the biosynthesis of polyketide-derived lipids in *Mycobacterium tuberculosis*. The Journal of Biological Chemistry, vol. 281, No. 3, pp. 1313-1316. Jan. 20, 2006.*

Aisaka et al., "Enzymatic synthesis of novel disaccharides using disaccharide phosphorylases," J. Biosci. Bioeng., 2000, vol. 90, 208-213.
Backus et al., "Uptake of unnatural trehalose analogs as a reporter for *Mycobacterium tuberculosis*," Nat. Chem. Biol., 2011, vol. 7, 228-235.
Belisle et al., "Role of the major antigen of *Mycobacterium tuberculosis* in cell wall biogenesis," Science, 1997, 276, 1420-2.
Belocopitow et al., "Enzymic synthesis of 6-deoxy-α-D-glucopyranosyl α-D-glucopyranoside and α-D-xylopyranosyl α-D-glucopyranoside," Carbohydr. Res., 1971, vol. 19, pp. 268-271.
Breidenbach et al., "Targeted metabolic labeling of yeast N-glycans with unnatural sugars," Proc. Natl. Acad. Sci. U.S.A., 2010, 107, 3988-3993.
Brennan et al., "The envelope of mycobacteria," Annu. Rev. Biochem., 1995, 64, 29-63.
Chaen et al.,"Efficient Enzymatic Synthesis of Disaccharide, α-D-Galactosyl α-D-Glucoside, by Trehalose Phosphorylase from Thermoanaerobacter brockii," J. Appl. Glycosci., 2001, vol. 48, pp. 135-137.
Elbein et al., "New insights on trehalose: a multifunctional molecule," Glycobiology, 2003, 13, 17R-27R.
Foley et al., "Bioorthogonal Chemical Reporters for Selective In Situ Probing of Mycomemembrane Components in Mycobacteria," Angew Chem Int Ed Engl. Feb. 5, 2016;55(6):2053-7.
Gobec et al., "Design, synthesis, biochemical evaluation and antimycobacterial action of phosphonate inhibitors of antigen 85C, a crucial enzyme involved in biosynthesis of the mycobacterial cell wall," Eur. J. Med. Chem., 2007, 42, 54.
Grzegorzewicz et al., "Inhibition of mycolic acid transport across the *Mycobacterium tuberculosis* plasma membrane," Nat. Chem. Biol., 2012, 19, 334-41.
Haberkant et al., In vivo profiling and visualization of cellular protein-lipid interactions using bifunctional fatty acids, Angew Chem Int Ed 2013, 52:4033-4038.
Kalscheuer et al., "Trehalose-recycling ABC transporter LpqY-SugA-SugB-SugC is essential for virulence of *Mycobacterium tuberculosis*," Proc. Natl. Acad. Sci. U.S.A., 2010, 107, 21761-66.
Kim et al., "Enzymatic synthesis of a galactose-containing trehalose analogue disaccharide by Pyrococcus horikoshii trehalose-synthesizing glycosyltransferase: Inhibitory effects on several disaccharidase activities," Journal of Molecular Catalysis B: Enzymatic 49, 2007, 98-103.
Kouril et al., "A novel trehalose synthesizing pathway in the hyperthermophilic Crenarchaeon Thermoproteus tenax: the unidirectional TreT pathway," Arch Microbiol, 2008, 190:355-369.
La Rosa et al., "MmpL3 Is the Cellular Target of the Antitubercular Pyrrole Derivative BM212," Antimicrob. Agents Chemother., 2012, 56, 324-331.
Marrakchi et al., "Mycolic acids: structures, biosynthesis, and beyond," Chem. Biol., 2013, 21, 67-85.

(Continued)

*Primary Examiner* — Samantha L Shterengarts
(74) *Attorney, Agent, or Firm* — Micheal Best & Friedrich LLP

(57) ABSTRACT

Described herein are trehalose analogues. Also described herein are methods of making the trehalose analogues and uses of the analogues. For example, the disclosed trehalose analogues may be useful in the detection of bacteria.

20 Claims, 69 Drawing Sheets

(56) References Cited

OTHER PUBLICATIONS

Maruta et al., "Formation of Trehalose from Maltooligosaccharides by a Novel Enzymatic System," Biosci. Biotechnol. Biochem., 1995, vol. 59, pp. 1829-1834.

Ohtake et al., "Trehalose: Current Use and Future Applications," J. Pharm. Sci., 2011, vol. 100, pp. 2020-2053.

Rose et al., "Synthesis and biological evaluation of trehalose analogs as potential inhibitors of mycobacterial cell wall biosynthesis," Carbohydr. Res., 2002, 337, 105-20.

Rostovtsev et al., "A stepwise huisgen cycloaddition process: copper(I)-catalyzed regioselective "ligation" of azides and terminal alkynes," Angew. Chem. Int. Ed., 2002, 41, 2596-9.

Ryu et al., "Molecular cloning and characterization of trehalose synthase from Thermotoga maritima DSM3109: Syntheses of trehalose disaccharide analogues and NDP-glucoses," Enzyme and Microbial Technology 47, 2010, 249-256.

Sarpe et al., "Regioselective Protection and Functionalization of Trehalose," Trends in Carbohydrate Research, 2013, vol. 5, pp. 8-33.

Stanley et al., "Identification of Novel Inhibitors of M. tuberculosis Growth Using Whole Cell Based High-Throughput Screening," ACS Chem. Biol., 2012, 7, 1377-84.

Swarts et al.,Probing the mycobacterial trehalome with bioorthogonal chemistry, J. Am. Chem. Soc., 2012, vol. 134, pp. 16123-16126.

Tornøe et al., "Peptidotriazoles on Solid Phase: [1,2,3]-Triazoles by Regiospecific Copper(I)-Catalyzed 1,3-Dipolar Cycloadditions of Terminal Alkynes to Azides," J. Org. Chem., 2002, 67, 3057-64.

Tournu et al., "Relevance of Trehalose in Pathogenicity: Some General Rules, Yet Many Exceptions," Pathog., 2013, 9, e1003447.

Van Der Borght et al., "Enzymatic Properties and Substrate Specificity of the Trehalose Phosphorylase from Caldanaerobacter subterraneus," Appl. Environ. Microbiol., 2011, vol. 77, 6939-6944.

Wang et al., "Synthesis of trehalose-based compounds and their inhibitory activities against *Mycobacterium smegmatis*," Bioorg. Med. Chem., 2004, 12, 6397-413.

Walmagh et al., "Treehalose Analogues: Latest insights in properties and biocatalytic production," Int J Mol Sci, 2015, 16, 13729-45.

Garcia et al., "Syntheses of hepta-, hexa-, and penta-pivalates of trehalose by selective pivaloylation," Carbohydrate Research, 1990, 200:307-317.

Lin et al., "Synthesis of mono- and dideoxygenated α,α-trehalose analogs," Carbohydr Res, 2007, 342(14):2014-2030.

Rundell et al., "Deoxyfluoro-D-trehalose (FDTre) analoges as potential PET probes for imaging mycobacterial infection," Organic & Biomolecular Chemistry, 2016, 12 pages.

\* cited by examiner

TREHALOSE ANALOGUES

CROSS-REFERENCE TO RELATED APPLICATIONS

This application claims priority to U.S. Provisional Application No. 62/385,772 filed on Sep. 9, 2016 and U.S. Provisional Application No. 62/411,999 filed on Oct. 24, 2016, both of which are incorporated fully herein by reference.

STATEMENT REGARDING FEDERALLY SPONSORED RESEARCH

This invention was made with government support under grant number CHE-1654408 awarded by the National Science Foundation. The government has certain rights in the invention.

TECHNICAL FIELD

The present disclosure relates to trehalose analogues and methods of using the trehalose analogues in diagnostic and therapeutic applications. Aspects of the trehalose analogues as well as methods of preparing the trehalose analogues are also described herein.

BACKGROUND

Trehalose (D-glucose-α-1,1-α-D-glucose) is a disaccharide sugar that is prevalent throughout nature, but not found in mammals. Trehalose is an essential metabolite for mycobacteria, such as *Mycobacterium tuberculosis* (Mtb), and is responsible for millions of deaths yearly and is a major global health threat due to drug resistance. Because trehalose and its derivatives, such as O-acylated derivatives (e.g., trehalose mono- and dimycolate) are integral to Mtb physiology and pathogenesis, yet absent from the human host, trehalose metabolism may be a target for diagnostic and therapeutic applications.

SUMMARY

Known trehalose analogues have potential liabilities with respect to specificity for Mtb. For example, known trehalose analogues can undergo lipidation and subsequent non-covalent association with the Mtb cell wall. This may be problematic because non-covalently associated molecules can shed from the cell wall, potentially resulting in loss of specificity for the bacterium. In addition, known trehalose analogues can potentially be metabolized by microorganisms other than mycobacteria, which can reduce specificity for Mtb. Accordingly, there is need for improved trehalose analogues.

In some aspects, the present disclosure provides a compound of formula (I)

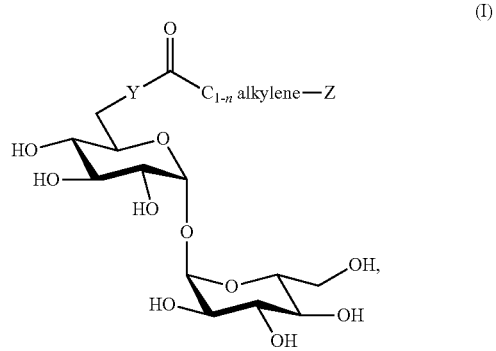

wherein Y is O or NH; Z is alkynyl, —$N_3$, a label or a therapeutic; and n is 0 to 50, wherein $C_{1-n}$ alkylene is optionally substituted.

In other aspects, the present disclosure provides a compound of formula (II)

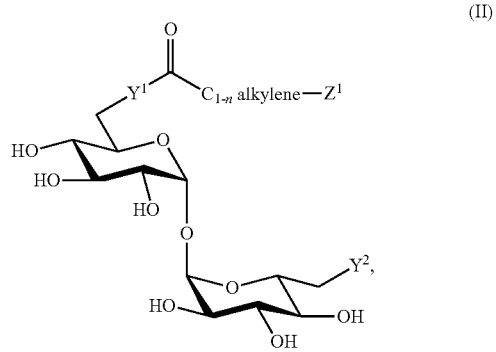

wherein $Y^1$ is O or NH; $Y^2$ is alkynyl, —$N_3$, OC(O)$C_{1-n}$ alkylene-$Z^2$, or NHC(O)$C_{1-n}$ alkylene-$Z^2$; $Z^1$ and $Z^2$ are each independently selected from the group consisting of alkynyl, —$N_3$, quencher, label and therapeutic; and n is 0 to 50, wherein $C_{1-n}$ alkylene is optionally substituted.

Use of compounds of formula (I) and (II) in methods of detecting and/or treating mycobacteria, and methods and processes for making the compounds are further described herein.

DETAILED DESCRIPTION

Figure 1:
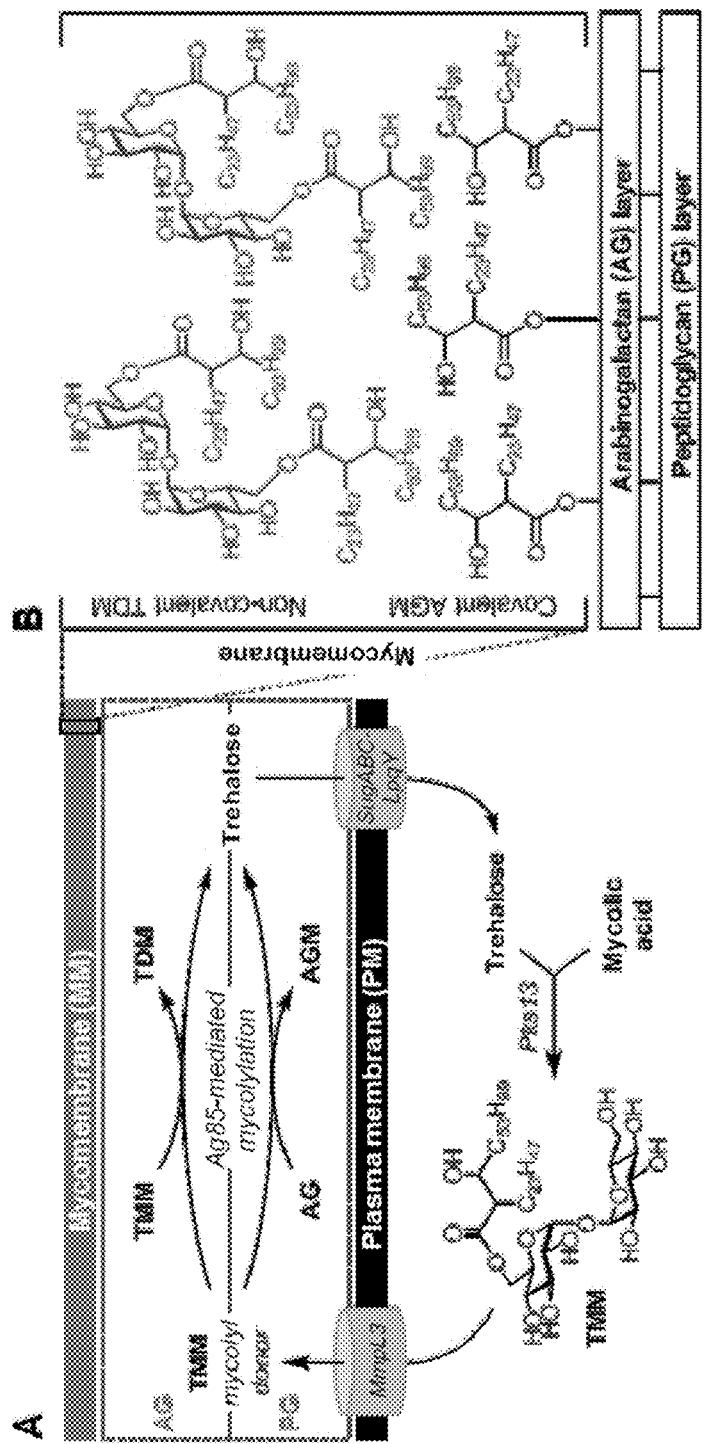
FIG. 1 shows a schematic of mycomembrane (MM) biosynthesis and simplified structure. A) Pathways involved in MM biosynthesis and B) Structures of the major constituents of the MM: Covalent arabinogalactan-mycolate (AGM) and trehalose dimycolate (TDM).

The present disclosure describes a class of trehalose analogues. The analogues can be used for the detection and therapeutic targeting of mycobacteria. Mycobacteria and other members of the Corynebacterineae have a unique cell envelope that is central to pathogenesis and provides intrinsic drug resistance (FIG. 1). Mycobacteria have plasma membrane (PM) and peptidoglycan (PG) layers, wherein PG is covalently attached to the arabinogalactan (AG) layer, which in turn is covalently modified with long-chain ($C_{60}$-$C_{90}$) fatty acids called mycolic acids. These AG-linked mycolates (AGM) are the foundation of the outer membrane, or mycomembrane (MM). In addition to AGM, the MM includes other noncovalently associated lipids and glycolipids, most prominently virulence-associated trehalose dimycolate (TDM).

Biosynthesis of the MM is mediated by the disaccharide trehalose (FIG. 1). In the cytoplasm, Pks13 links trehalose to mycolic acid to generate trehalose monomycolate (TMM), which, after translocation across the PM by MmpL3, acts as the mycolyl donor required for construction of the MM. The antigen 85 complex (Ag85), consisting of several mycolyl-transferases, is responsible for transferring mycolyl groups from the mycolyl donor TMM to either i) AG, leading to the formation of AGM, or ii) another molecule of TMM, generating TDM. During these processes, trehalose is released and recycled by the transporter SugABC-LpqY. The MM is essential to bacterial viability and many of its constituents are required for virulence in Mtb, so it presents a valuable target for TB diagnostic and drug development.

Figure 31:
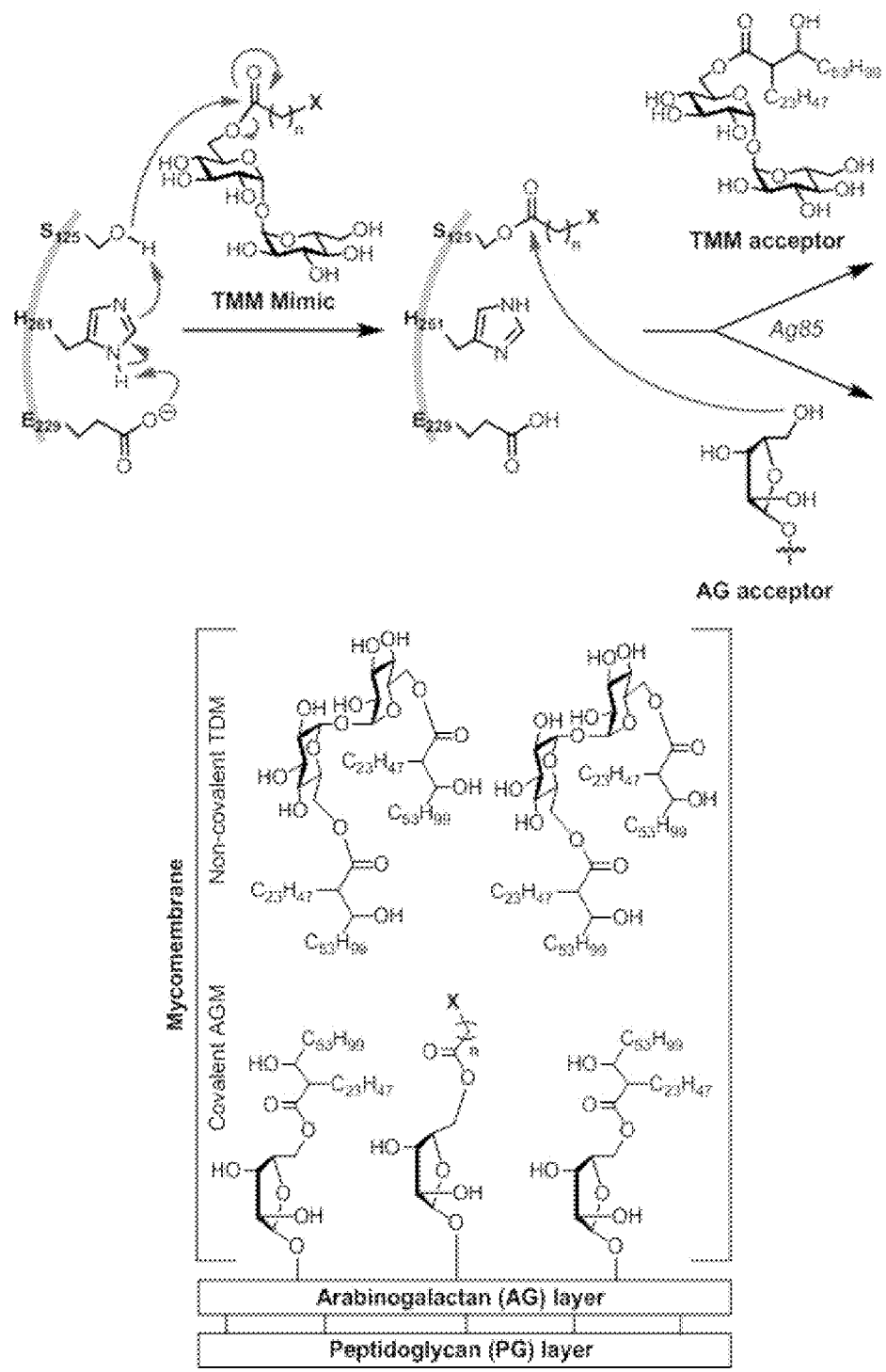
FIG. 31 shows a schematic of how the disclosed compounds are hypothesized to label bacterium cell walls. The arrow pointing upwards in the top portion of the figure leads to non-covalent labeling and the arrow pointing downwards leads to covalent labeling, which is represented in the lower portion of the figure.

It is hypothesized that the disclosed analogues can take advantage of the aforementioned trehalose metabolism of mycobacteria (FIG. 31). This affords the disclosed analogues to be covalently bound to the bacterium, which obviates specificity problems of known trehalose analogues that non-covalently modify bacterium. In addition, mammals do not have enzymes that act on trehalose monomycolate, so the disclosed trehalose analogues may exhibit higher specificity for Mtb in the host environment compared to known trehalose analogues that have their detectable tag located directly on the trehalose disaccharide, which may be broken down in mammals via trehalose-cleaving enzymes called trehalases, or broken down by others types of microorganisms.

Accordingly, the disclosed trehalose analogues can be advantageous for the detection and targeting of mycobacteria for both diagnostics and therapeutics. Furthermore, the disclosed analogues have a broad flexibility in structure (due in part to the tolerance of the targeted biological machinery), which can permit the delivery of a very broad range of cargo to mycobacteria.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkoxyalkyl" as used herein, refers to an alkoxy group, as defined herein, appended to the parent molecular moiety through an alkyl group, as defined herein.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylamino," as used herein, means at least one alkyl group, as defined herein, is appended to the parent molecular moiety through an amino group, as defined herein.

The term "alkenyl," as used herein, means a straight or branched, unsaturated hydrocarbon chain containing at least one carbon-carbon double bond and from 2 to 30 carbon atoms. The term "lower alkenyl" or "$C_2$-$C_6$ alkenyl" means a straight or branched chain hydrocarbon containing at least one carbon-carbon double bond and from 1 to 6 carbon atoms. The term "$C_6$-$C_{30}$ alkenyl" means a straight or branched chain hydrocarbon containing at least one carbon-carbon double bond and from 6 to 30 carbon atoms. The term "$C_{12}$-$C_{18}$ alkyl" means a straight or branched chain hydrocarbon containing at least one carbon-carbon double bond and from 12 to 18 carbon atoms. The alkenyl groups, as used herein, may have 1, 2, 3, 4, or 5 carbon-carbon double bonds. The carbon-carbon double bonds may be cis or trans isomers.

The term "alkylene," as used herein, refers to a divalent group derived from a straight or branched chain hydrocarbon of 1 to 50 carbon atoms, for example, of 2 to 5 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "alkynyl," as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "coupling reagent," as used herein, refers to a compound that aids the reaction, e.g., coupling, between two different molecules. An example of a coupling reagent includes N,N'-dicyclohexylcarbodiimide.

The term "alkoxyfluoroalkyl" as used herein, refers to an alkoxy group, as defined herein, appended to the parent molecular moiety through a fluoroalkyl group, as defined herein.

The term "amide," as used herein, means —C(O)NR— or —NRC(O)—, wherein R may be hydrogen, alkyl, cycloalkyl, aryl, heteroaryl, heterocycle, alkenyl, or heteroalkyl.

The term "aryl" as used herein, refers to a phenyl group, or bicyclic aryl or tricyclic aryl fused ring systems. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl. The monocyclic, bicyclic, and tricyclic aryls are connected to the parent molecular moiety through any carbon atom contained within the rings, and can be unsubstituted or substituted.

The term "cycloalkenyl" as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "cycloalkoxy," as used herein, refers to a cycloalkyl group, as defined herein, appended to the parent molecular moiety through an oxygen atom.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl. "Cycloalkyl" also includes carbocyclic ring systems in which a cycloalkyl group is appended to the parent molecular moiety and is fused to an aryl group as defined herein, a heteroaryl group as defined herein, or a heterocycle as defined herein.

The term "deprotection reagent," as used herein, refers to a compound that liberates a compound that is chemically protected. An example of a deprotection reagent is a Dowex 50WX8-400 H+ ion-exchange resin.

The term "fluoroalkoxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "halogen" or "halo" as used herein, means Cl, Br, I, or F.

The term "haloalkoxy" as used herein, means at least one haloalkyl group, as defined herein, is appended to the parent molecular moiety through an oxygen atom.

The term "haloalkyl" as used herein, means an alkyl group, as defined herein, in which one, two, three, four, five, six, seven or eight hydrogen atoms are replaced by a halogen.

The term "heteroalkyl" as used herein, means an alkyl group, as defined herein, in which one or more of the carbon atoms has been replaced by a heteroatom selected from S, Si, O, P and N. The heteroatom may be oxidized. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups are exemplified by a monocyclic heteroaryl ring appended to the parent molecular moiety and fused to two of a monocyclic cycloalkyl group, as defined herein, a monocyclic aryl group, as defined herein, a monocyclic heteroaryl group, as defined herein, or a monocyclic heterocycle, as defined herein. Representative examples of monocyclic heteroaryl include, but are not limited to, pyridinyl (including pyridin-2-yl, pyridin-3-yl, pyridin-4-yl), pyrimidinyl, pyrazinyl, thienyl, furyl, thiazolyl, thiadiazolyl, isoxazolyl, pyrazolyl, and 2-oxo-1,2-dihydropyridinyl. Representative examples of bicyclic heteroaryl include, but are not limited to, chromenyl, benzothienyl, benzodioxolyl, benzotriazolyl, quinolinyl, thienopyrrolyl, thienothienyl, imidazothiazolyl, benzothiazolyl, benzofuranyl, indolyl, quinolinyl, imidazopyridine, benzooxadiazolyl, and benzopyrazolyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings, and can be unsubstituted or substituted.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,3-dimethylpyrimidine-2,4(1H,3H)-dione, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "hydroxyl" as used herein, means an —OH group.

The term "hydroxyalkyl" as used herein, means an alkyl group, as defined herein, in which one, two, three, four, five, six, seven or eight hydrogen atoms are replaced by a hydroxyl group.

The term "label," as used herein, refers to a molecule or compound that can be detected directly or after applying a stimulus. Examples of labels include luminescent labels which emit radiation on exposure to an external source of radiation or other stimulus, e.g. fluorescent materials or fluorophores (which emit light when exposed to light), chemiluminescent materials (which emit light during chemical reaction), electroluminescent materials (which emit light on application of an electric current), phosphorescent materials (in which emission of light continues after exposure to light stimulus has ended) and thermoluminescent materials (which emit light once a certain temperature is exceeded). Examples of fluorophores include fluoresceins, xanthenes, cyanines, naphthalenes, coumarins, oxadiazoles, pyrenes, oxazines, acridines, arylmethines, Alexa Fluors and tetrapyrroles. Further fluorophores include quantum dots, which emit highly specific wavelengths of electromagnetic radiation after stimulation, for example by electricity or light.

Other labels include radioactive labels, including positron emitting nuclei such as $^{18}$F, $^{64}$Cu or $^{124}$I which can be detected by imaging techniques such as positron emission topography (PET). Other radioactive labels such as $^{14}$C, $^3$H, or iodine isotopes such as $^{123}$I and $^{131}$I, which can be detected using autoradiographic analysis or scintillation detection for example, can also be used. In the case of gamma-emitting nuclei, imaging techniques such as single photon emission computed tomography (SPECT) can be used. Other labels include those that are NMR-active, which can be detected by magnetic resonance techniques, for example magnetic resonance imaging (MRI) or nuclear magnetic resonance (NMR) detectors, the labels typically comprising one or more NMR-active nuclei that are not generally found in concentrated form elsewhere in the organism, biological sample or *mycobacterium*, examples being $^{13}$C, $^2$H (deuterium) or $^{19}$F. Further labels include those comprising atoms with large nuclei, for example atoms with atomic number of 35 or more, preferably 40 or more and even more preferably 50 or more, for example iodine or barium, which are effective contrast agents for X-ray photographic techniques or computed tomography (CT) imaging techniques.

Other labels include those that can bind favorably and specifically to another reagent, for example use of a biotin label. Biotin binds very specifically to avidin and streptavidin, and hence the presence of a biotin label can be detected by addition of an avidin or streptavidin-modified molecule, for example avidin and streptavidin-modified fluorescent dyes.

The term "chemically protected," as used herein in the conventional chemical sense and pertains to one or more reactive functional groups of a compound being protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

The term "quencher," as used herein refers to a chemical substituent that can negate the emission of fluorescence from an excited fluorophore. For example, a photon from an energetically excited fluorophore, the "donor", raises the energy state of an electron in another molecule, the "acceptor", to higher vibrational levels of the excited singlet state. As a result, the energy level of the donor fluorophore returns to the ground state, without emitting fluorescence, thereby being quenched.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituted" refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

The term "therapeutic" refers to an agent capable of treating and/or ameliorating a condition or disease, or one or more symptoms thereof, in a subject. Examples include immune stimulants, photosensitizers, nanoparticles, lipophilic molecules, and agents that impair cell adhesion.

2. Trehalose Analogues

Disclosed herein are a class of trehalose analogues. The analogues can be used for the detection of bacteria and in particular mycobacteria (e.g., *Mycobacterium tuberculosis* (Mtb)). The analogues are designed to mimic naturally occurring biosynthetic substrates called trehalose monomycolate and trehalose dimycolate. In mycobacteria, a group of enzymes called the antigen 85 (Ag85) complex have the function of transferring lipids from trehalose monomycolate onto the cell wall, leading to covalent attachment of the lipid to the bacterium (in nature, this is an essential step for biosynthesis of the Mtb outer membrane). In addition, trehalose dimycolate is activated by a related enzyme called trehalose dimycolate hydrolase.

Instead of a natural, native lipid, the disclosed analogues have a non-native lipid that is (i) truncated relative to its native counterpart that can improve solubility; and (ii) can be modified with a chemical tag (e.g., to enable detection). Therefore, when bacteria are contacted with the analogues, the non-native lipid bearing a tag can be covalently bound to the cell wall. A schematic of the hypothesized strategy of the disclosed analogues is described in FIG. 31.

The disclosed trehalose analogues may be compounds of formula (I), (I-a), (I-b) or (II) as described below.

A. Compounds of Formula (I)

In one aspect, disclosed are compounds of formula (I):

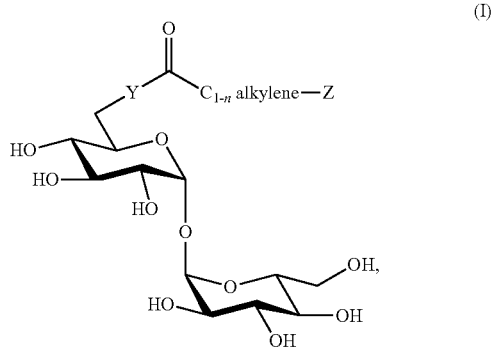

(I)

wherein Y is O or NH; Z is alkynyl, $—N_3$, a label or a therapeutic; and n is 0 to 50, wherein $C_{1-n}$ alkylene is optionally substituted.

In certain embodiments, the $C_{1-n}$ alkylene is optionally substituted with 0, 1, 2, 3, 4, or 5 substituents, each independently selected from the group consisting of halogen, hydroxy, $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ alkoxyalkyl, $C_1$-$C_6$ alkylC(O)$C_1$-$C_6$ alkyl, $C_1$-$C_6$ alkylC(O)OH, aryl, heteroaryl, cycloalkyl, cycloalkenyl, and heterocycle. In certain embodiments, the $C_{1-n}$ alkylene is optionally substituted with two substituents that can be taken together to form a ring. The two substituents may be on the same carbon atom. For example, one carbon atom of the alkylene may be substituted with a diazirine ring.

In certain embodiments, the $C_{1-n}$ alkylene is optionally substituted with 0, 1, 2, or 3 substituents, each independently selected from the group consisting of hydroxy, $C_1$-$C_6$ alkyl, $C_1$-$C_6$ alkoxyalkyl, $C_1$-$C_6$ alkylC(O)$C_1$-$C_6$ alkyl, and $C_1$-$C_6$ alkylC(O)OH.

In certain embodiments, the $C_{1-n}$ alkylene is branched. In certain embodiments, the $C_{1-n}$ alkylene may have a branch at the alpha position. For example, the $C_{1-n}$ alkylene may be:

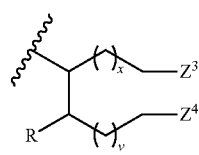

wherein $Z^3$ is $—CH_3$, alkynyl, $—N_3$, a label, or a therapeutic; $Z^4$ is $—CH_3$, alkynyl, $—N_3$, a label, or a therapeutic; x is 1 to 50; v is 1 to 50; and R is —OH or —H. In certain embodiments, the total of x and v combined is 20 to 100. In certain embodiments, x is 1 to 25 and v is 1 to 25. In addition, branched $C_{1-n}$ alkylene may also be optionally substituted as described above.

The compounds described herein may include functional groups that allow for bioorthogonal chemistry which enable selective in situ detection of the disclosed compounds in vitro and/or in vivo. For example, in certain embodiments, Z is alkynyl or $—N_3$. In these embodiments, the disclosed compounds may be incorporated into a bacterial cell wall and then detected through a bioorthogonal reaction with the Z substituent. For example, detection through site-specific click chemistry techniques. In addition, these embodiments may be incorporated into a bacterial cell wall and then reacted with a therapeutic that has a functional group reactive with alkynyl or $—N_3$.

The compounds described herein may include a label. The label may be detectable in in vitro and/or in vivo. In certain embodiments, Z is a label that is luminescent, radioactive, detectable by NMR, detectable by X-ray imaging or a combination thereof. In certain embodiments, Z is a label that is detectable by PET, MRI, CT, SPECT, fluorescence or a combination thereof. In other embodiments, Z is a label that comprises a fluorophore, one or more positron emitting nuclei selected from $^{18}F$, $^{64}Cu$ and $^{124}I$, one or more radioactive isotopes selected from $^{14}C$, $^{3}H$, $^{123}I$ and $^{131}I$, one or more NMR-detectable isotopes selected from $^{13}C$, $^{2}H$ or $^{19}F$, an X-ray detectable element with an atomic number of at least 35, or a combination thereof.

In certain embodiments, the label is a fluorophore selected from the group consisting of fluoresceins, xanthenes, cyanines, naphthalenes, coumarins, oxadiazoles, pyrenes, oxazines, acridines, arylmethines, Alexa Fluors, tetrapyrroles, quantum dots and a combination thereof.

The compounds described herein may include a therapeutic. The therapeutic may be able to kill bacteria, decrease the amount of bacteria, impair the ability of bacteria to function, etc. For example, where bacteria (e.g., mycobacteria) have been identified in a cell, tissue, or subject, said cell, tissue, or subject may be treated with disclosed compounds having a therapeutic. Examples of therapeutics include, but are not limited to, immune stimulants, photosensitizers, nanoparticles, lipophilic molecules, and agents that impair cell adhesion.

In certain embodiments, the therapeutic is an antibody-recruiting small molecule (ARM). In certain embodiments, the ARM is 2,4-dinitrophenyl.

In certain embodiments, Z is alkynyl, $—N_3$, or a label; and n is 2 to 10

In certain embodiments, Z is alkynyl or $—N_3$; and n is 4 to 9.

In certain embodiments, Z is a label; and n is 4 to 9.

In certain embodiments, Z is selected from the group consisting of:

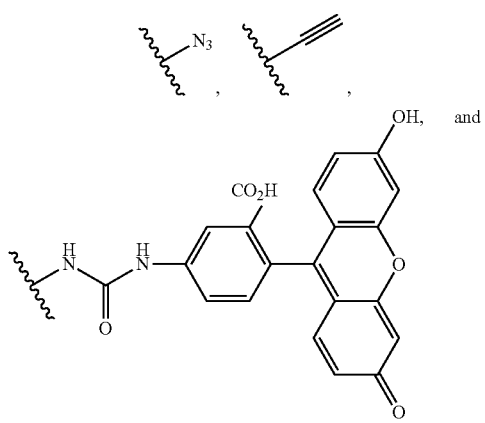

-continued
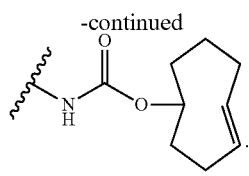
In certain embodiments, Y is NH or O. For example, the compound of formula (I) may be a compound of formula (I-a) or (I-b):
(I-a)
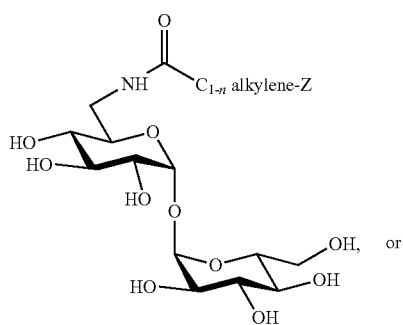
or
(I-b)
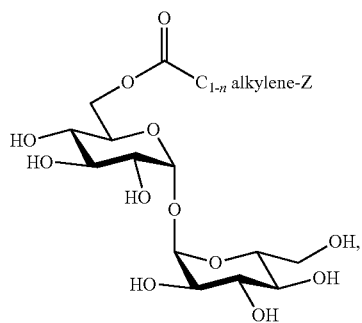
wherein Z is alkynyl, —N₃, a label, or a therapeutic; and n is 0 to 50, wherein $C_{1-n}$ alkylene is optionally substituted.
In certain embodiments, the compound of formula (I) is selected from the group consisting of:
(I-a-1)
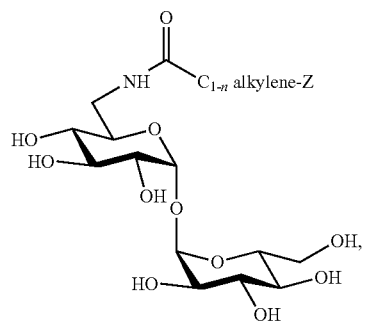
(I-a-2)
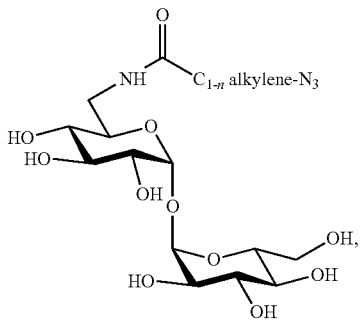
(I-a-3)
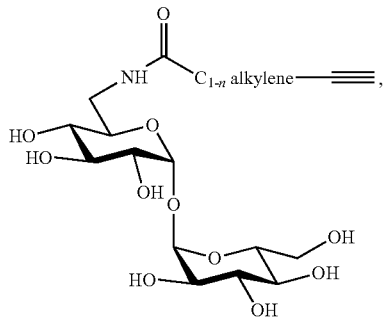
(I-a-4)
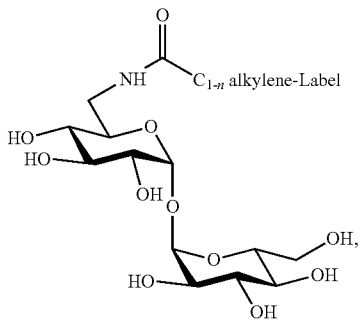
(I-a-5)
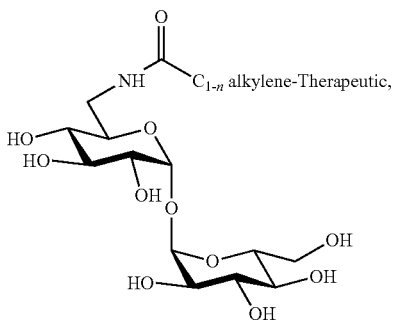
(I-a-6)
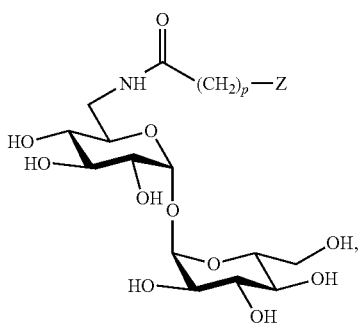

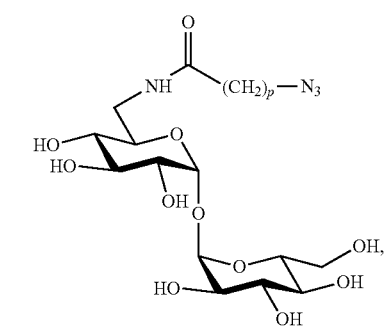
(I-a-7)
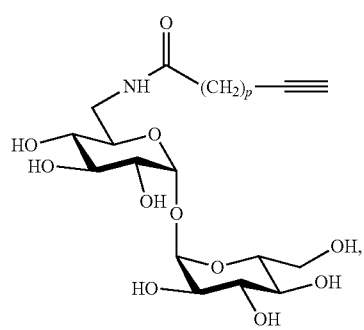
(I-a-8)
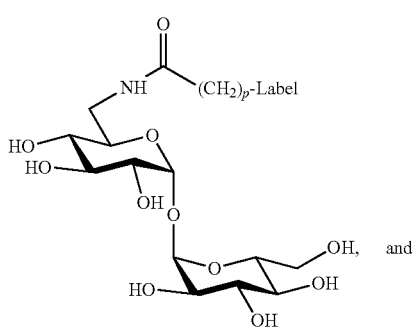
(I-a-9)
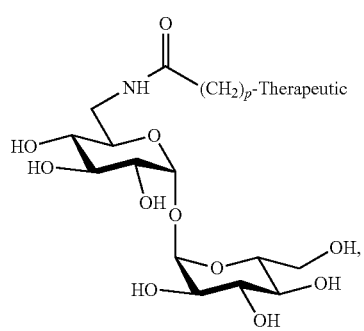
(I-a-10)
wherein p is 1, 2, 3, 4, 5, 6, 7, 8, 9, or 10. In certain embodiments, p is 1, 2, 4 or 9.
In certain embodiments, the compound of formula (I) is selected from the group consisting of:
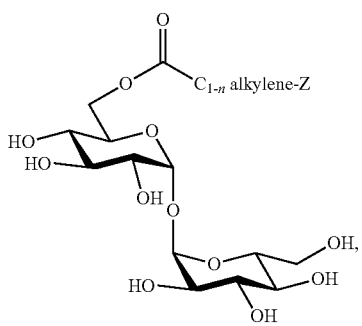
(I-b-1)
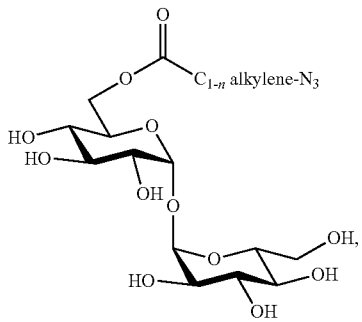
(I-b-2)
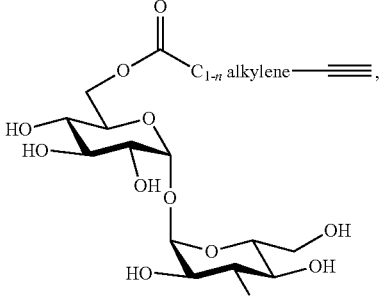
(I-b-3)
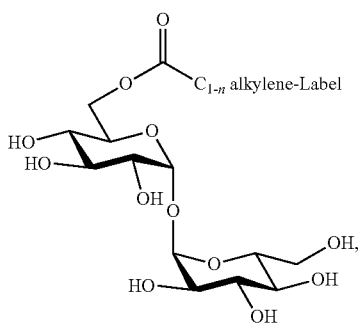
(I-b-4)
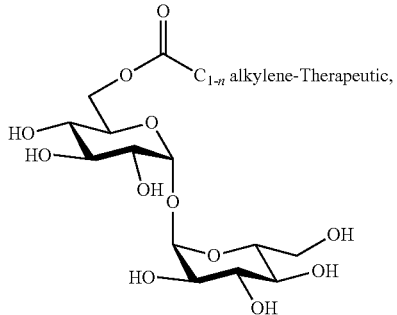
(I-b-5)

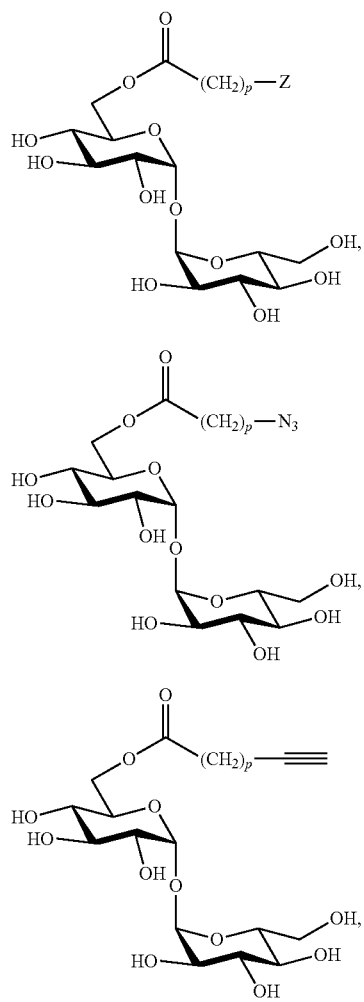
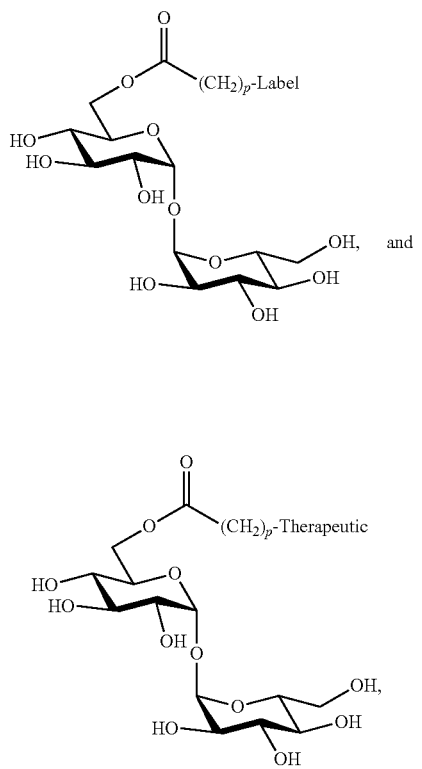
wherein p is 1, 2, 3, 4, 5, 6, 7, 8, 9, or 10. In certain embodiments, p is 1, 2, 4 or 9.
In certain embodiments, the compound of formula (I) is selected from the group consisting of:
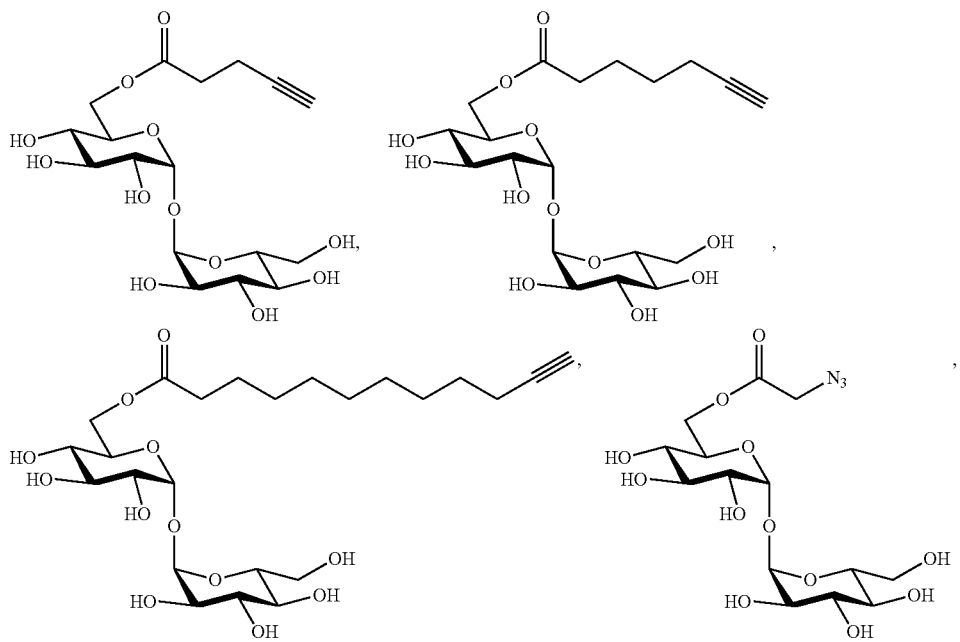

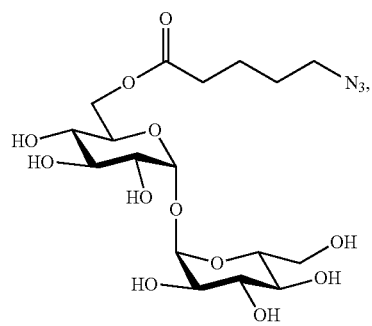
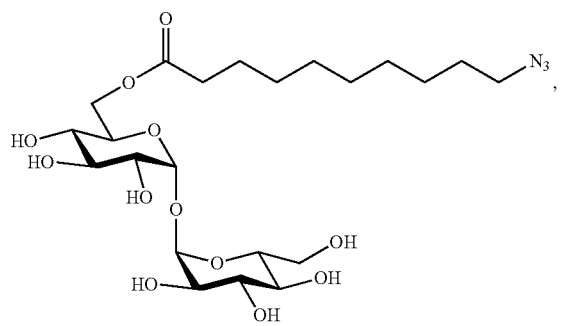
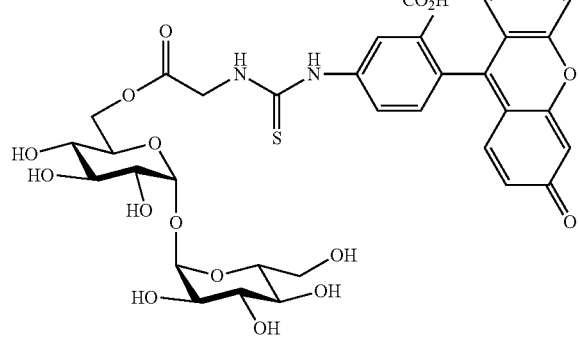
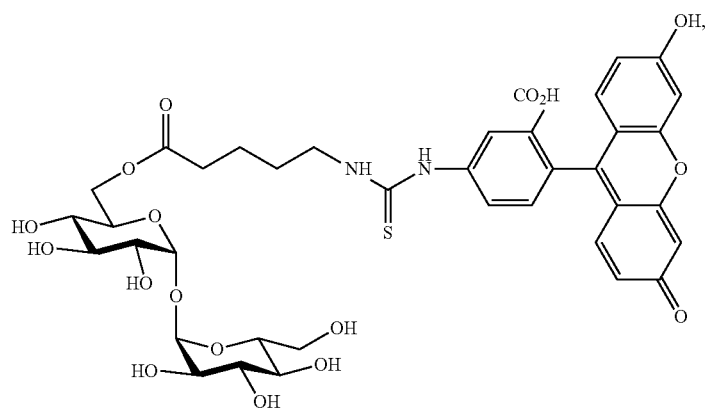
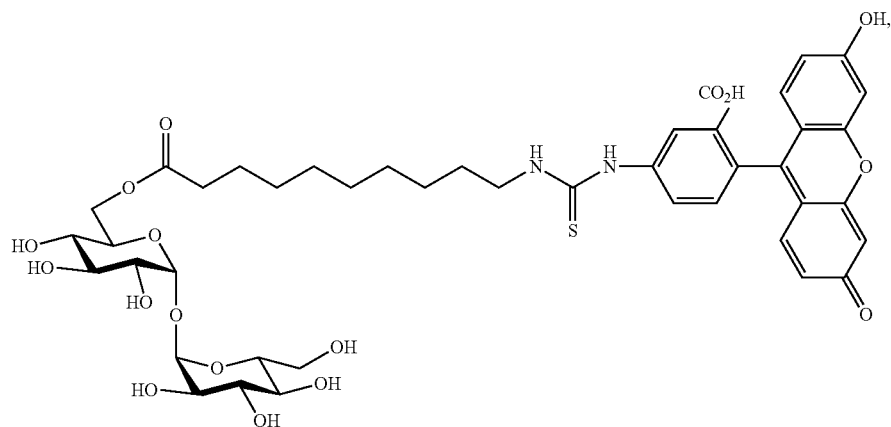

-continued

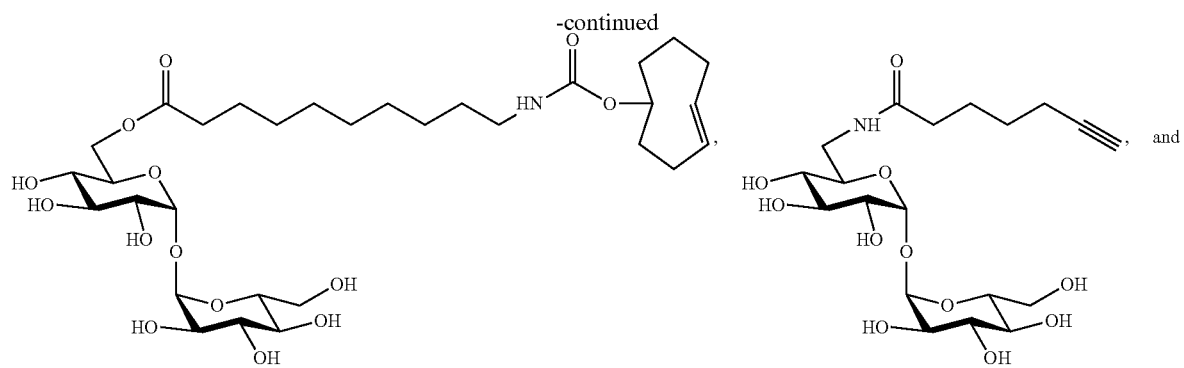

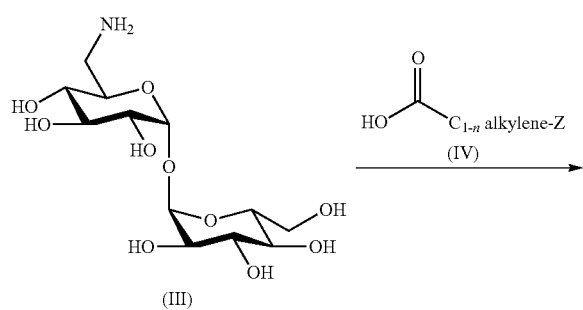

1. Synthesis of Compounds of Formula (I-a) & (I-b)

Compounds of formula (I-a) may be prepared by synthetic processes. Compounds of formula (I-a), wherein the meanings of n and Z are set forth above, may be synthesized as shown in Scheme 1.

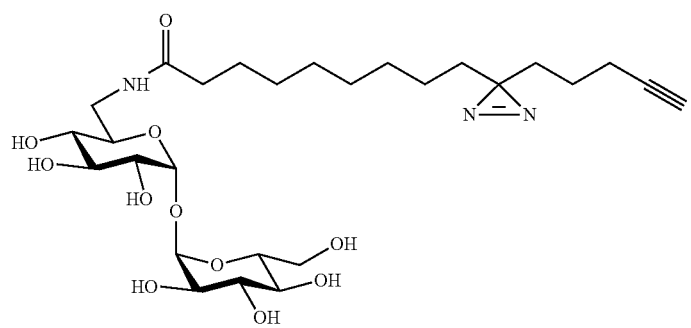

Scheme 1 illustrates that compounds of formula (I-a) can be prepared by reacting the compounds of formula (III) with compounds of formula (IV). For example, compounds of formula (I-a) may be prepared by coupling of the amine in the compound of formula (III) with a carboxylic acid of formula (IV).

In certain embodiments, reacting the compound of formula (III) with the compound of formula (IV) may include employing a solvent as a component of the reaction mixture. The solvent may be any solvent suitable to dissolve the starting materials and promote the reaction to proceed to the desired product (e.g. a compound of formula (I-a)).

In certain embodiments, reacting the compound of formula (III) with the compound of formula (IV) may be done at approximately room temperature.

Compounds of formula (I-b) may be prepared by synthetic processes. Compounds of formula (I-b), wherein the meanings of n and Z have been set forth above, may be synthesized as shown in Scheme 2.

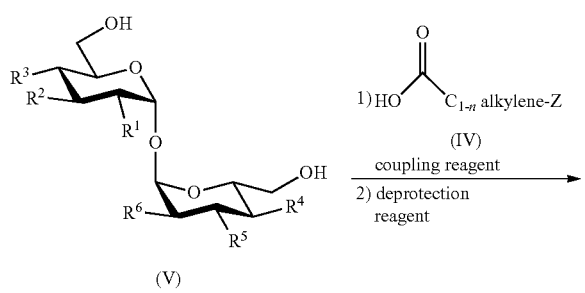

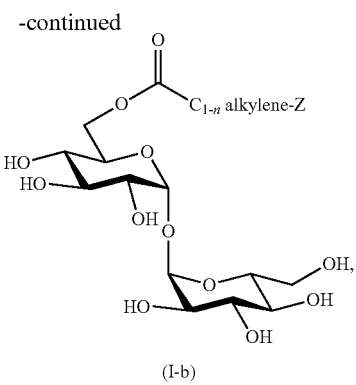

(I-b)

Scheme 2 illustrates that compounds of formula (I-b) can be prepared by coupling the compounds of formula (V) with compounds of formula (IV). The variables $R^1$, $R^2$, $R^3$, $R^4$, $R^5$, and $R^6$ are each —OH and optionally chemically protected. For example, compounds of formula (I-b) may be prepared by coupling the compound of formula (V) with a carboxylic acid of formula (IV), and then removing the protecting groups as necessary of $R^1$, $R^2$, $R^3$, $R^4$, $R^5$, and $R^6$.

In certain embodiments, reacting the compound of formula (V) with the compound of formula (IV) may include employing a solvent as a component of the reaction mixture. The solvent may be any solvent suitable to dissolve the starting materials and promote the reaction to proceed to the desired product (e.g. a compound of formula (I-b)). In certain embodiments, a solvent may be added to the reaction mixture to terminate the reaction.

In certain embodiments, reacting the compound of formula (V) with the compound of formula (IV) may be done at approximately room temperature.

In certain embodiments, $R^1$, $R^2$, $R^3$, $R^4$, $R^5$, and $R^6$ are not chemically protected and the compound of formula V is directly acylated to provide the compound of formula (I-b). Compounds of formula (I-b) prepared in this manner may optionally be purified via reverse-phase (C18) chromatography.

Compounds of formula (III) or (V) have substituents that may be chemically protected. A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxy group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(O)CH$_3$, —OAc).

The carboxylic acid of formula (IV) can be coupled with an amine function of the compounds through the use of (2-(1H-benzotriazol-1-yl)-1,1,3,3-tetramethyluronium hexafluorophosphate) ("HBTU"). The carboxylic acid of formula (IV) can be coupled with a hydroxyl-containing compound through use of N,N'-Dicyclohexylcarbodiimide ("DCC").

In certain embodiments, the protecting groups can be removed under acidic conditions. For example, a suitable deprotection reagent is Dowex 50WX8-400 H$^+$ ion-exchange resin.

In certain embodiments (of Scheme 1 and 2), the compound of formula (IV) is 6-heptynoic acid.

In certain embodiments, the amine-contained compounds of formula (III) can be derived from the corresponding azide. For example, the amine may be obtained through a Staudinger reduction of the azide with triphenylphosphine.

The compounds and intermediates of the above-mentioned synthetic schemes may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

B. Compounds of Formula (II)

In one aspect, disclosed are compounds of formula (II):

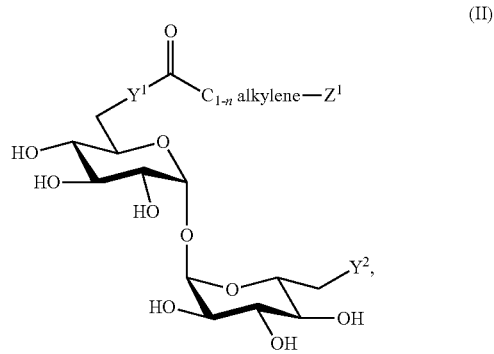

wherein $Y^1$ is O or NH; $Y^2$ is alkynyl, —N$_3$, OC(O)C$_{1-n}$ alkylene-Z$^2$, or NHC(O)C$_{1-n}$ alkylene-Z$^2$; Z$^1$ and Z$^2$ are each independently selected from the group consisting of alkynyl, —N$_3$, quencher, label, and therapeutic; and n is 0 to 50, wherein $C_{1-n}$ alkylene is optionally substituted. In addition, compounds of formula (II) may be optionally substituted as described above regarding compounds of formula (I).

In certain embodiments, $Z^1$ is a label and $Z^2$ is a quencher, or vice versa. In these embodiments, compounds of formula II may act as FRET probes, which are detectable after undergoing cellular metabolism.

In certain embodiments, $Y^1$ is O; $Y^2$ is $OC(O)C_1$-$C_n$ alkylene-$Z^2$; $Z^1$ is fluorophore; and $Z^2$ is quencher.

In certain embodiments, $Y^1$ is O; $Y^2$ is alkynyl or —$N_3$; and $Z^1$ is alkynyl or —$N_3$.

In certain embodiments, $Y^1$ is O; $Y^2$ is $NHC(O)C_{1-n}$ alkylene-$Z^2$; $Z^1$ is fluorophore; and $Z^2$ is quencher.

In certain embodiments, the compound of formula (II) is bioorthogonal tag, such as an alkyne or azide, the sample can be further contacted with a compound that is reactive with the bioorthogonal tag and includes a detectable label and then assessed for mycobacteria. In instances where a compound of formula (I) or (II) includes a label, the compound may be added to the sample and directly assessed for mycobacteria.

The assessment of mycobacteria detection can be performed in real-time (e.g., detection at time 0 relative to adding a compound of formula (I) or (II) to a sample). In addition, detecting labeled mycobacteria may be performed from about 1 minute to about 24 hours following addition of a compound of formula (I) or (II) to a sample. For example, detecting labeled mycobacteria may be performed about 1

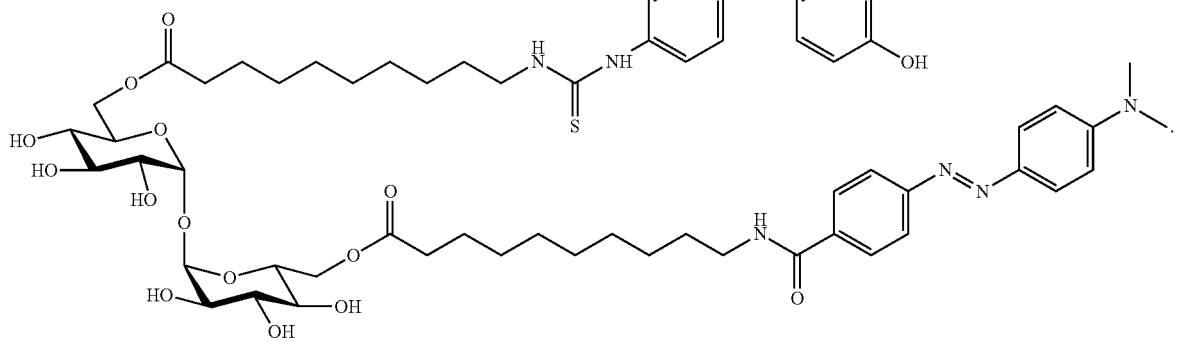

3. Use of Trehalose Analogues

The disclosed trehalose analogues may be advantageous for a number of different applications. For example, organisms that contain trehalose and/or metabolize trehalose may be targeted by compounds of formula (I) or (II) in applications such as diagnostics (e.g., molecular imaging) and therapy (e.g., targeted therapeutics). The disclosed trehalose analogues can have a broad flexibility that affords a broad range of cargo that may be targeted and/or localized to organisms that contain trehalose and/or metabolize trehalose, such as mycobacteria. Furthermore, the compounds of formula (I) or (II) may have a high specificity to mycobacteria by being able to covalently modify the bacterium. This high specificity may negate potential problems of shedding of the bacterium cell wall, which can result in off target effects and false-positive visualization of the probe.

A. Diagnostics

The present disclosure provides a simple and facile method for the synthesis and use of chemical probes to detect live mycobacteria, e.g., *Mycobacterium tuberculosis*. Compounds of formula (I) or (II) may be directly added to a sample and assessed for the presence of mycobacteria. In instances where a compound of formula (I) or (II) has a minute, about 5 minutes, about 10 minutes, about 20 minutes, about 30 minutes, about 40 minutes, about 50 minutes, about 1 hour, about 2 hours, about 3 hours, about 4 hours, about 5 hours, about 10 hours, about 12 hours, about 18 hours or about 24 hours following addition of a compound of formula (I) or (II) to a sample.

The disclosed methods may detect mycobacteria by various imaging techniques, including but not limited to, PET, MRI, CT, SPECT, fluorescence or a combination thereof. In certain embodiments, the detectable label may include a fluorophore, $^{18}F$, $^{64}Cu$, $^{124}I$, $^{14}C$, $^{3}H$, $^{123}I$, $^{131}I$, $^{13}C$, $^{2}H$, $^{19}F$, or a combination thereof.

The disclosed methods may detect *mycobacterium* in various different biological samples, including but not limited to, sputum, cerebrospinal fluid, pericardial fluid, synovial fluid, ascitic fluid, blood, bone marrow, urine, feces, or a cell. The methods of the present disclosure may be useful in cells grown in culture medium, (e.g., in vitro, or in cells within animals, e.g., in vivo).

In certain embodiments, a subject is administered the disclosed compounds and the subject is assessed for the presence of mycobacteria. The subject to be administered the disclosed compounds can be one that is in need of diagnosis (e.g., detection of mycobacteria). Accordingly, a variety of subjects may be amenable to diagnosis using the compounds disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

B. Therapeutics

The present disclosure also provides methods for treating diseases in a subject caused by *mycobacterium*, e.g., *Mycobacterium tuberculosis*. The disclosed trehalose analogues with truncations in the lipid chain (relative to their native counterpart) may be capable of remodeling the Mtb outer membrane to render it more permeable, potentially increasing access of antibiotics to the cell. In this instance, the disclosed compounds may be able to improve combination chemotherapy.

The disclosed trehalose analogues may be used to specifically deliver therapeutics, which can be coupled through a compound's bioorthogonal tag, into the bacterium and may also keep the therapeutic in close proximity to the bacterium by being incorporated into its cell wall. Examples of therapeutics include, but are not limited to, immune stimulants, photosensitizers, nanoparticles, lipophilic molecules, and agents that impair cell adhesion. In certain embodiments, the disclosed compounds may include antibody-recruiting small molecules (ARMs). The disclosed compounds can enable delivery of ARMs specifically to Mtb cells within a host, priming the host immune system to recognize Mtb and enhance its clearance.

By "treatment" it is meant that at least an amelioration of the symptoms associated with the condition afflicting the subject is achieved, where amelioration is used in a broad sense to refer to at least a reduction in the magnitude of a parameter, e.g., symptom, associated with the condition being treated. As such, treatment also includes situations where the pathological condition, or at least symptoms associated therewith, are completely inhibited, e.g., prevented from happening, or stopped, e.g., terminated, such that the subject no longer suffers from the condition, or at least the symptoms that characterize the condition. Thus, treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

The subject to be treated can be one that is in need of therapy, where the subject to be treated is one amenable to treatment using the disclosed compounds. Accordingly, a variety of subjects may be amenable to treatment using the compounds disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of compound administered to a subject (for diagnosis and/or treatment) can be initially determined based on guidance of a dose and/or dosage regimen of the parent drug. In general, the compounds can provide for targeted delivery, thus providing for at least one of reduced dose or reduced administrations in a dosage regimen.

The compounds of the present disclosure can be delivered by any suitable means (e.g., pharmaceutical formulation), including oral, parenteral and topical methods. For example, transdermal administration methods, by a topical route, can be formulated as applicator sticks, solutions, suspensions, emulsions, gels, creams, ointments, pastes, jellies, paints, powders, and aerosols.

The pharmaceutical formulation may be provided in unit dosage form. In such form the pharmaceutical formulation may be subdivided into unit doses containing appropriate quantities of the compounds of the present disclosure. The unit dosage form can be a packaged preparation, the package containing discrete quantities of the preparation, such as packeted tablets, capsules, and powders in pouches, vials or ampoules. Also, the unit dosage form can be a capsule, tablet, dragee, cachet, or lozenge, or it can be the appropriate number of any of these in packaged form.

Compounds of the present disclosure can be present in any suitable amount, and can depend on various factors including, but not limited to, weight and age of the subject, state of the disease, etc. Suitable dosage ranges for the compounds of the present disclosure include from 0.1 mg to 10,000 mg, or 1 mg to 1000 mg, or 10 mg to 750 mg, or 25 mg to 500 mg, or 50 mg to 250 mg. For instance, suitable dosages for the compounds of the present disclosure include 1 mg, 5 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg or 1000 mg.

In some embodiments, multiple doses of a compound are administered. The frequency of administration of a compound can vary depending on any of a variety of factors, e.g., severity of the symptoms, condition of the subject, etc. For example, in some embodiments, a compound is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The compounds of the present disclosure can be administered at any suitable frequency, interval and duration. For example, the compounds of the present disclosure can be administered once an hour, or two, three or more times an hour, once a day, or two, three, or more times per day, or once every 2 days, 3 days, 4 days, 5 days, 6 days, or 7 days, so as to provide the desired dosage level to the subject. When the compounds of the present disclosure are administered more than once a day, representative intervals include 5 min, 10 min, 15 min, 20 min, 30 min, 45 min and 60 minutes, as well as 1 hr, 2 hr, 4 hr, 6 hr, 8 hr, 10 hr, 12 hr, 16 hr, 20 hr, and 24 hours. The compounds of the present disclosure can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The compounds of the present disclosure can be co-administered with another active agent. Co-administration includes administering a compound of the present disclosure and active agent within 0.5 hr, 1 hr, 2 hr, 4 hr, 6 hr, 8 hr, 10 hr, 12 hr, 16 hr, 20 hr, or 24 hours of each other. Co-administration also includes administering a compound of the present disclosure and active agent simultaneously or approximately simultaneously (e.g., within about 1 min, 5 min, 10 min, 15 min, 20 min, or 30 minutes of each other), or sequentially in any order. In addition, a compound of the present disclosure and the other active agent can each be administered once a day, or two, three, or more times per day so as to provide the desired dosage level per day.

In some embodiments, co-administration can be accomplished by co-formulation, e.g., preparing a single pharmaceutical formulation including both a compound of the present disclosure and the active agent. In other embodiments, a compound of the present disclosure and the active agent can be formulated separately and co-administered to the subject.

The compounds of the present disclosure and the active agent can be present in a formulation in any suitable weight ratio, such as from 1:100 to 100:1 (w/w), or 1:50 to 50:1, or 1:25 to 25:1, or 1:10 to 10:1, or 1:5 to 5:1 (w/w). The compounds of the present disclosure and the other active agent can be present in any suitable weight ratio, such as 1:100 (w/w), 1:75, 1:50, 1:25, 1:10, 1:5, 1:4, 1:3, 1:2, 1:1, 2:1, 3:1, 4:1, 5:1, 10:1, 25:1, 50:1, 75:1, or 100:1 (w/w). Other dosages and dosage ratios of the compounds of the present disclosure and the active agent are suitable in the formulations and methods described herein.

4. Examples

The compounds and processes of the invention will be better understood by reference to the following examples, which are intended as an illustration of and not a limitation upon the scope of the invention.

Example 1

Synthesis & Characterization of O- and N-AlkTMMs

General Methods for Synthesis.

Materials and reagents were obtained from commercial sources without further purification unless otherwise noted. Anhydrous solvents were obtained either commercially or from an alumina column solvent purification system. All reactions were carried out in oven-dried glassware under inert gas unless otherwise noted. Analytical TLC was performed on glass-backed silica gel 60 Å plates (thickness 250 m) from Dynamic Adsorbents and detected by charring with 5% $H_2SO_4$ in EtOH. Column chromatography was performed using flash-grade silica gel 32-63 m (230-400 mesh) from Dynamic Adsorbents. $^1H$ NMR spectra were recorded at 300 MHz with chemical shifts in ppm (δ) referenced to solvent peaks. $^{13}C$ NMR spectra were recorded at 75 MHz. NMR spectra were obtained on a Varian Mercury 300 instrument. Coupling constants (J) are reported in hertz (Hz). High-resolution electrospray ionization (HR ESI) mass spectra were obtained using a Waters LCT Premier XE using either raffinose or reserpine as the lock mass.

Generally, to synthesize O-AlkTMM compounds, Kulkarni's approach was used to access unsymmetrical trehalose esters (Scheme 3A). First, trehalose was subjected to per-O-trimethylsilylation, then both 6-O-trimethylsilyl groups were selectively removed using K2CO3/CH3OH to give diol 7. This C2-symmetric intermediate was desymmetrized in the subsequent step, which entailed 6-O-monoesterification with an appropriate alkyne- or azide-modified carboxylic acid in the presence of N,N'-dicyclohexylcarbodiimide (DCC) and catalytic 4-(dimethylamino)pyridine (DMAP). The intermediate was then desilylated in the presence of Dowex H+ resin, delivering the desired products. The yields for compounds 1-4 over the two-step monoesterification-deprotection sequence ranged from 34-44%.

Regarding N-AlkTMM, it was accessed from 6-TreAz by Staudinger reduction followed by coupling with 6-heptynoic acid. The shortened lipid chain conferred excellent water solubility to both compounds, which facilitated their storage and use in labeling experiments. The synthesis is described in more detail below.

For acronyms used below: ADC=liquid medium supplement containing albumin, dextrose, catalayse; AG=arabinogalactan; AGM=arabinogalactan-linked mycolate; Ag85=antigen 85 complex; Alk488=alkyne-modified carboxyrhodamine 110; A.u.=arbitrary units; Az488=azide-modified carboxyrhodamine 110; BSA=bovine serum albumin; CuAAC=Cu-catalyzed azide-alkyne cycloaddition; DCC=N,N'-dicyclohexylcarbodiimide; DBCO=dibenzocyclooctyne; DIEA=Diisopropylethylamine; DMAP=4-dimethylaminopyridine; DMF=N,N-dimethylformamide; DMSO=dimethylsulfoxide; HBTU=N,N,N',N'-tetramethyl-O-(1H-benzotriazol-1-yl)uronium hexafluorophosphate; HR ESI MS=high-resolution electrospray ionization mass spectrometry; FITC=fluorescein isothiocyanate; LB=lysogeny broth; MDR=multi-drug-resistant; MFI=mean fluorescence intensity; MM=mycomembrane; Msmeg=*Mycobacterium smegmatis* mc2155 S4; Mtb=*M. tuberculosis*; OD600=optical density measured by absorbance at a wavelength of 600 nm; PBS=phosphate-buffered saline; PBSB=PBS 1× with 0.5% bovine serum albumin; PG=peptidoglycan; PM=plasma membrane; S/N=signal-to-noise ratio; TB=tuberculosis; TBTA=tris[(1-benzyl-1H-1,2,3-triazol-4-yl)methyl]amine; TDM=trehalose dimycolate; THF=tetrahydrofuran; TLC=thin layer chromatography; TMM=trehalose monomycolate; TMS=trimethylsilyl; TreAz=azide-modified trehalose; XDR=extensively-drug-resistant.

Table 1 describes some of the disclosed O-AlkTMMs and potential advantages of the compounds.

TABLE 1

Examples of O-AlkTMMs

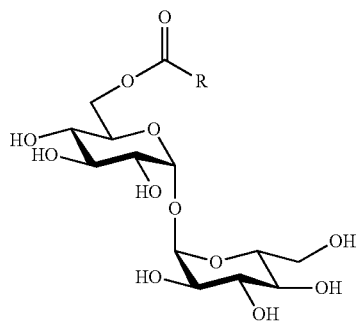

TMM-based reporters

| Compound | R group | Comments |
| --- | --- | --- |
| O-AlkTMM-C5 (1) | *pentynyl* | Alkyne enables CuAAC; Varied chain lengths allow evaluation of the effect of this substrate property on labeling efficiency |
| O-AlkTMM-C7 (2) | *heptynyl* | |
| O-AlkTMM-C11 (3) | *undecynyl* | |
| O-AzTMM-C10 (4) | *azidodecyl* ($N_3$) | Azide enables CuAAC and SPAAC for live cell labeling; Versatile synthetic intermediate |
| O-TCO-TMM (5) | *alkyl-($)_r$-NHC(O)O-trans-cyclooctene* | Trans-cyclooctene enables tetrazine ligation for rapid labeling of live cells |
| O-FITC-TMM (6) | *alkyl-($)_7$-NH-C(S)-NH-fluorescein* | Fluorophore enables one-step labeling of live cells |

Scheme 3:

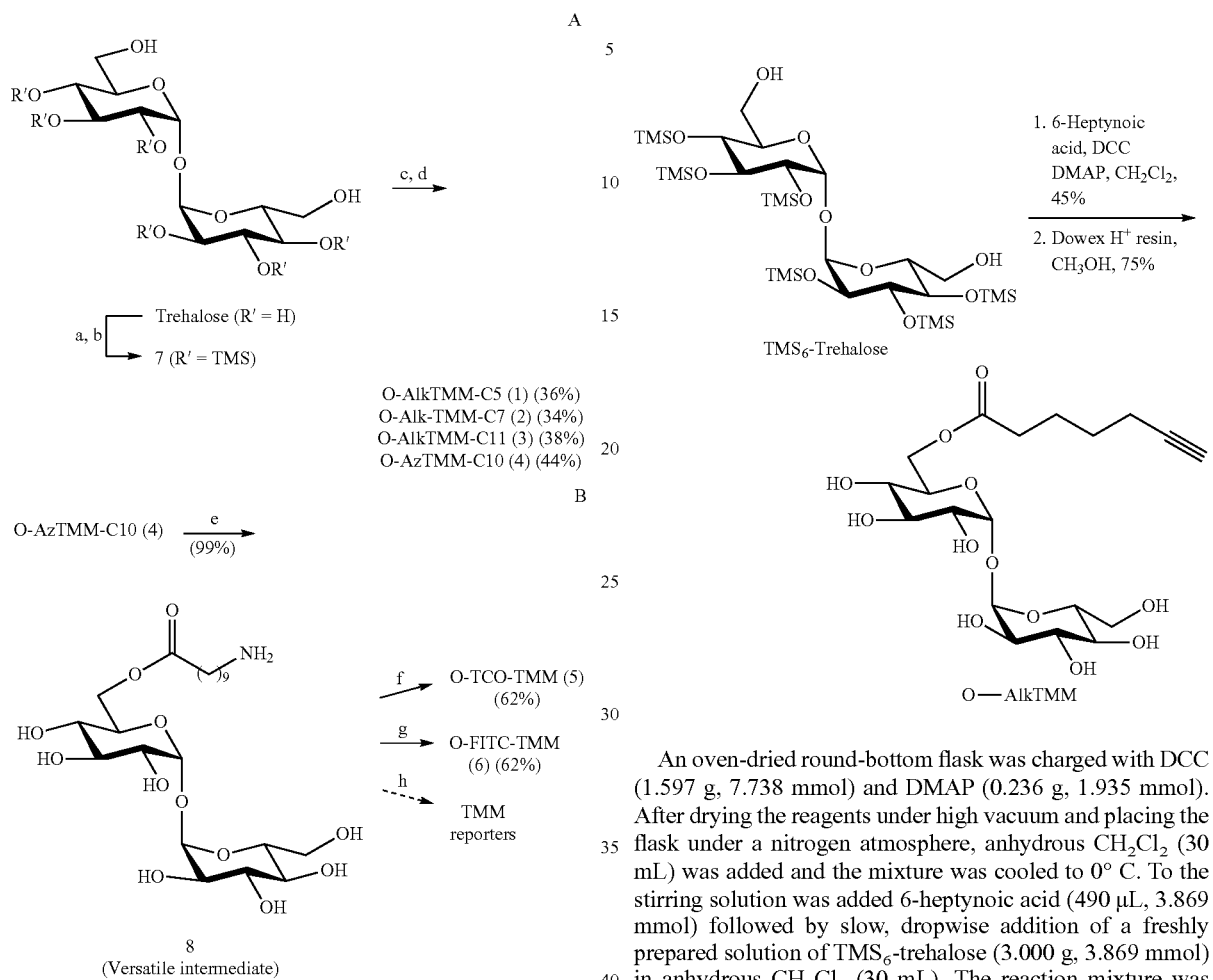

(A) Syntheses of alkyne- and azide-modified TMM reporters 1-4. a) TMSCl, Et₃N; b) K₂CO₃, CH₃OH (92% over two steps, ref. 31); c) carboxylic acid, DCC, DMAP, CH₂Cl₂; d) Dowex H⁺ resin, CH₃OH (yields over two steps are given). (B) Syntheses of TCO- and fluorescein-modified TMM reporters 5 and 6. e) Pd/C, H2, CH₃OH; f) NHS-TCO, Et₃N, N,N'-dimethylformamide (DMF); g) FITC, Et₃N, DMF; h) reaction of 8 with any commercially available amine-reactive reagent will provide access to custom TMM reporters.

To access trans-cyclooctene- and fluorescein-modified TMM analogues 5 and 6 (Scheme 3B). Therefore, O-Az-TMM-C10 (4) was converted into the corresponding amine 8 by Pd-catalyzed hydrogenation, which proceeded in nearly quantitative yield (99%). Intermediate 8 allows modification of the TMM scaffold with virtually any type of chemical cargo, which can provide easy access to TMM reporters tailored to specific applications. Amine 8 was reacted with either the N-hydroxysuccinimidyl carbonate of trans-cyclooctene (NHS-TCO) to generate O-TCO-TMM (5) or fluorescein isothiocyanate (FITC) to generate O-FITC-TMM (6). Purification by C18 reverse-phase chromatography yielded 5 and 6 in 62% and 85% yield, respectively. Further details on these compounds are laid out below.

6-O-(6-heptynoyl)-α,α-D-trehalose (O-AlkTMM or O-AlkTMM-CT)

An oven-dried round-bottom flask was charged with DCC (1.597 g, 7.738 mmol) and DMAP (0.236 g, 1.935 mmol). After drying the reagents under high vacuum and placing the flask under a nitrogen atmosphere, anhydrous CH₂Cl₂ (30 mL) was added and the mixture was cooled to 0° C. To the stirring solution was added 6-heptynoic acid (490 µL, 3.869 mmol) followed by slow, dropwise addition of a freshly prepared solution of TMS₆-trehalose (3.000 g, 3.869 mmol) in anhydrous CH₂Cl₂ (30 mL). The reaction mixture was stirred and gradually allowed to warm to room temperature. After 5 h, TLC (hexanes/ethyl acetate 4:1) showed generation of the presumed monoester product (Rf=0.49) and diester product (Rf=0.67). The reaction was quenched by addition of excess CH₃OH and concentrated by rotary evaporation. After resuspension of the crude product in CH₂Cl₂, the insoluble byproduct DCU was removed by filtration. The filtrate containing crude product was concentrated by rotary evaporation and purified by silica gel chromatography (hexanes/ethyl acetate 8:1 containing 1% Et₃N) to give the pure monoester intermediate (1.546 g, 45%) as a pale yellow syrup. The intermediate was dissolved in anhydrous CH₃OH (500 mL) and placed under a nitrogen atmosphere. Dowex 50WX8-400 H⁺ ion-exchange resin (8.7 g) was added and the reaction was stirred for 30 min at room temperature, after which TLC (CH₂Cl₂/CH₃OH 2:1) indicated that the reaction was complete (Rf=0.24). After the ion-exchange resin was filtered off, the filtrate was concentrated by rotary evaporation, purified by silica gel chromatography (CH₂Cl₂/CH₃OH 2:1), and filtered to give O-Alk-TMM (0.636 g, 75%) as a white solid.

O-AlkTMM may also be prepared by direct acylation of trehalose, such that compounds can be formed in one step. This direct acylation of trehalose can be combined with reverse-phase (C18) purification to achieve desired purity.

$^1$H NMR (300 MHz, D₂O): δ 5.18 (d, J=4.2 Hz, 1H), 5.16 (d, J=3.6 Hz, 1H), 4.45 (dd, J=1.5, 12.3 Hz, 1H), 4.30 (dd,

J=4.8, 12.3 Hz, 1H), 4.03 (m, 1H), 3.90-3.63 (m, 7H), 3.50 (t, J=9.9 Hz, 1H), 3.44 (t, J=9.3 Hz, 1H), 2.48 (t, J=6.9 Hz, 2H), 2.37 (dd, J=1.8, 3.0 Hz, 1H), 2.28-2.22 (m, 2H), 1.74 (pent, J=6.9 Hz, 2H), 1.56 (pent, J=6.9 Hz, 2H). $^{13}$C NMR (75 MHz, D$_2$O): δ 176.19, 93.40, 93.23, 85.64, 72.54, 72.31, 72.17, 70.93, 70.87, 69.90, 69.65, 69.59, 69.36, 63.00, 60.46, 33.21, 27.00, 23.43, 17.20. HR ESI MS negative mode: calcd. for C$_{19}$H$_{29}$O$_{12}$ [M–H]$^-$ m/z, 449.1659; found, 449.1555. (FIG. 17-21).

N-(6-heptynoyl)-6-amino-6-deoxy-α,α-D-trehalose (N-AlkTMM)

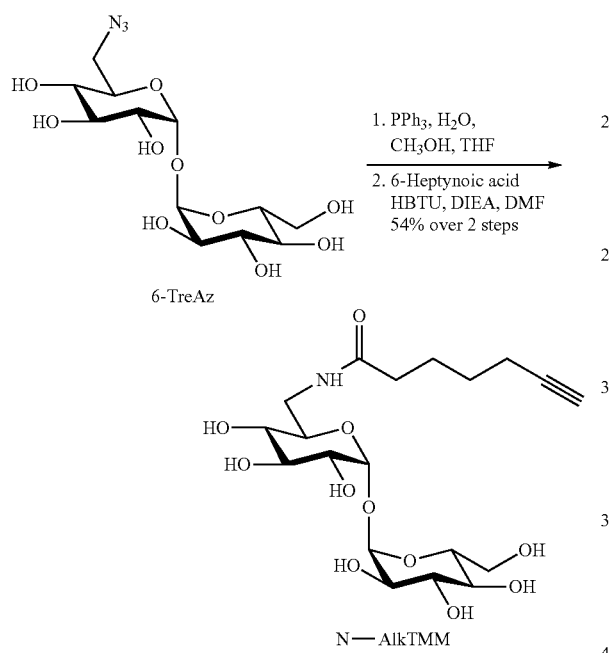

Triphenylphosphine (0.145 g, 0.553 mmol) was added to a stirring solution of 6-TreAz (0.197 g, 0.537 mmol) in anhydrous THF/CH$_3$OH (3:1). After stirring for 1 h at room temperature, H$_2$O (300 µL) was added and the reaction was stirred overnight. TLC analysis showed an incomplete reaction, so additional triphenylphosphine (0.5 equivalents) and water (400 µL) were added until TLC showed consumption of all starting material. The reaction mixture was concentrated by rotary evaporation, resuspended in H$_2$O, and washed three times with CHCl$_3$ to remove the triphenylphosphine oxide byproduct. The aqueous layer was concentrated by rotary evaporation and dried under high vacuum to give the intermediate amine. Half of the obtained intermediate amine was taken forward to the next step. To a 10 mL round-bottom flask containing anhydrous DMF (5 mL) was added 6-heptynoic acid (39.0 µL, 0.273 mmol), HBTU (0.138 g, 0.364 mmol), and DIEA (79.6 µL, 0.457 mmol). This mixture was stirred for 30 min at room temperature, after which it was added dropwise to a solution of the intermediate amine (0.0943 g, 0.273 mmol theoretical) in anhydrous DMF (5 mL). After stirring at room temperature for 2 h, TLC (CH$_2$Cl$_2$/CH$_3$OH 2:1) indicated the reaction was complete, forming a single less polar product (Rf=0.24). The crude product was concentrated by rotary evaporation, purified by silica gel chromatography using a gradient elution (CH$_2$Cl$_2$/CH$_3$OH 10:1→CH$_2$Cl$_2$/CH$_3$OH 2:1), and filtered to give N-AlkTMM (0.0662 g, 54% over two steps) as a white solid.

$^1$H NMR (300 MHz, D$_2$O): δ 5.17 (d, J=4.2 Hz, 1H), 5.13 (d, J=3.6 Hz, 1H), 3.86-3.70 (m, 6H), 3.66-3.61 (m, 2H), 3.60 (dd, J=2.7, 10.5 Hz, 1H), 3.44-3.37 (m, 2H), 3.30 (t, J=9.3 Hz, 1H), 2.37 (t, J=2.4 Hz, 1H), 2.29 (t, J=7.5 Hz, 2H), 2.23 (dt, J=2.4, 6.9 Hz, 2H), 1.70 (pent, J=6.9 Hz, 2H), 1.52 (pent, J=7.5 Hz, 2H). $^{13}$C NMR (75 MHz, D$_2$O): δ 176.99, 93.15, 93.05, 85.66, 72.61, 72.22, 72.14, 71.18, 70.98, 70.57, 69.61, 69.38, 60.48, 39.62, 35.21, 27.06, 24.63, 17.25. HR ESI MS negative mode: calcd. for C$_{19}$H$_{30}$NO$_{11}$ [M–H]$^-$ m/z, 448.1819; found, 448.1827. (FIG. 22-26).

Unlabeled Probes for Competition Experiments: 6-O-(6-heptanoyl)-α,α-D-trehalose and N-(6-heptanoyl)-6-amino-6-deoxy-α,α-D-trehalose

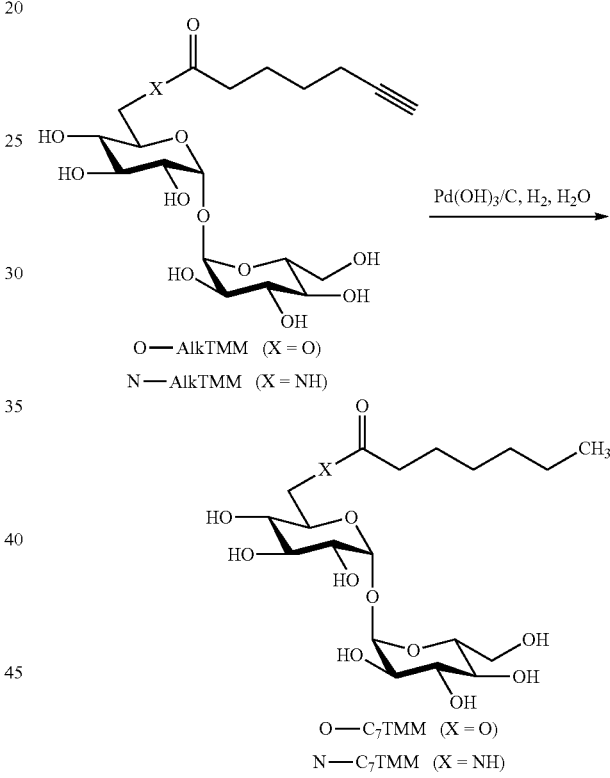

To a solution of AlkTMM (O-AlkTMM: 5.6 mg, 0.013 mmol; N-AlkTMM: 11.2 mg, 0.0249 mmol) in water under an argon atmosphere was added Pd(OH)$_2$ on carbon (1 mg). A hydrogen-filled balloon was connected to the reaction flask and the argon atmosphere was exchanged for hydrogen. After stirring under a hydrogen atmosphere at room temperature overnight, the reaction mixture was filtered through Celite and the filtrate was concentrated by rotary evaporation to give the reduced product (O—C$_7$TMM: 5.6 mg, 99%; N—C$_7$TMM: 11.2 mg, 99%).

Figure 27:
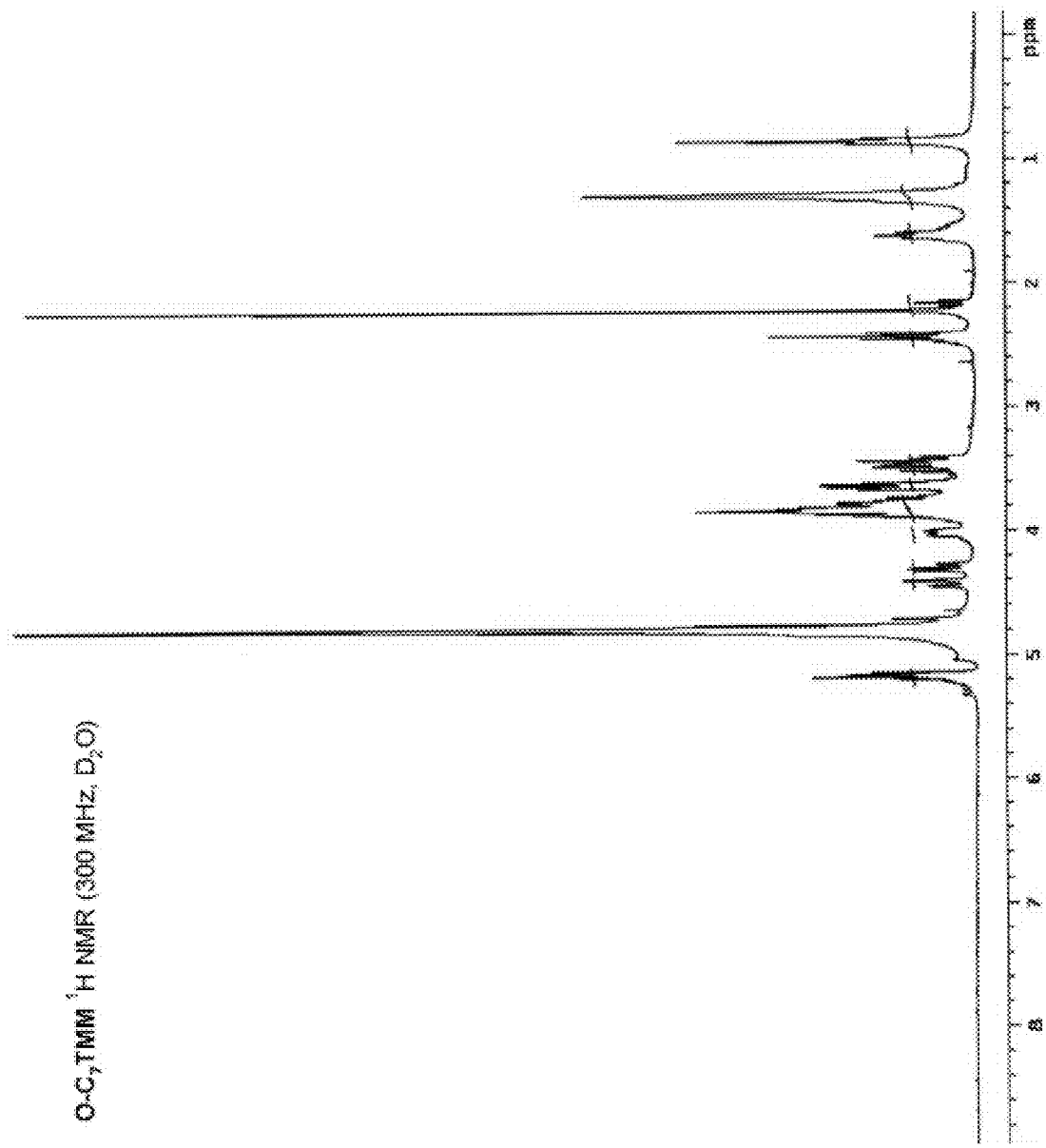
FIG. 27 shows a $^1H$ NMR spectrum of 6-O-(6-heptanoyl)-α,α-D-trehalose (O—$C_7$TMM).
Figure 28:
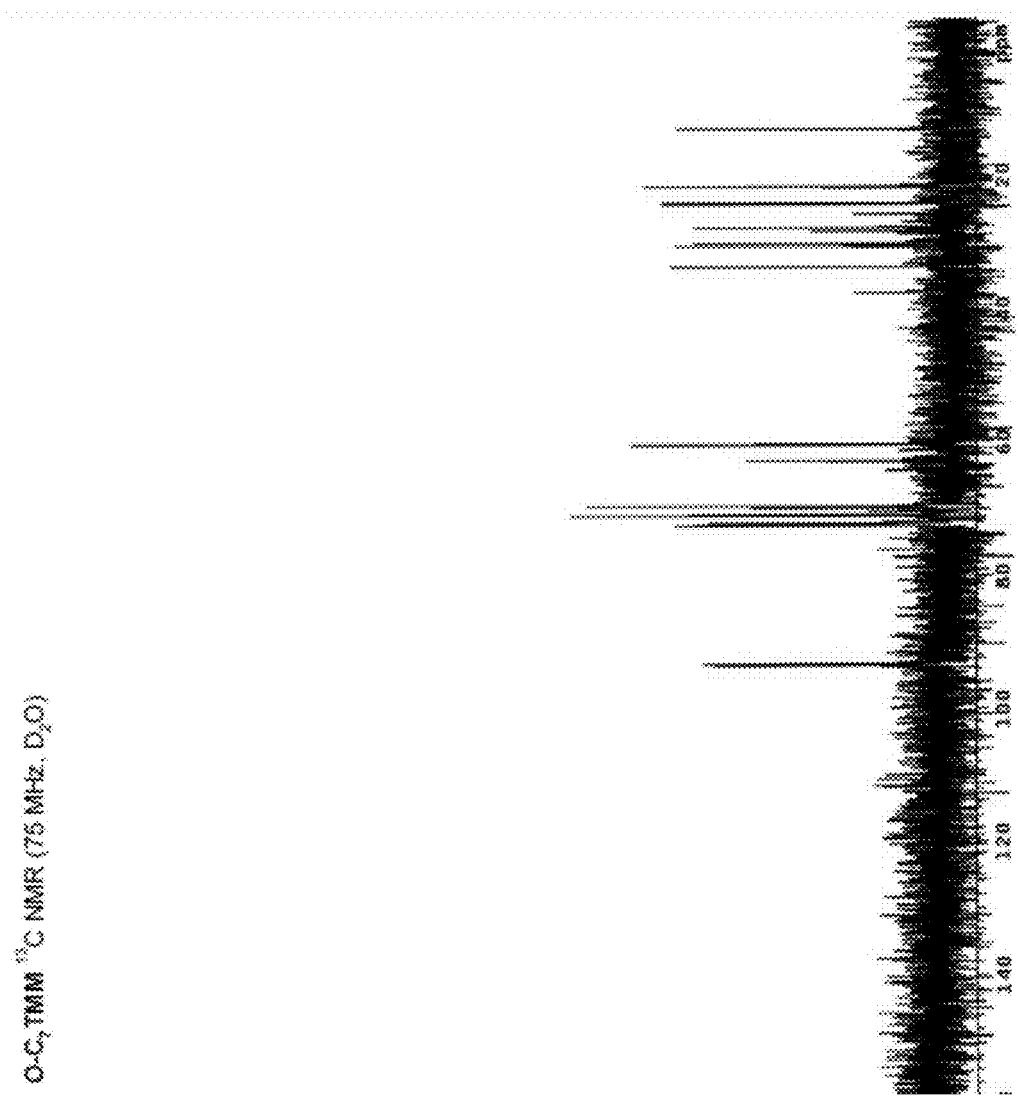
FIG. 28 shows a $^{13}C$ NMR spectrum of O—$C_7$TMM.

$^1$H NMR for O—C$_7$TMM (300 MHz, D$_2$O): δ 5.16 (d, J=3.9 Hz, 1H), 5.14 (d, J=3.6 Hz, 1H), 4.43 (dd, J=2.4, 12.3 Hz, 1H), 4.29 (dd, J=4.8, 12.3 Hz, 1H), 4.03-3.98 (m, 1H), 3.89-3.60 (m, 7H), 3.48 (t, J=9.6 Hz, 1H), 3.43 (t, J=9.6 Hz, 1H) 2.42 (t, J=7.5 Hz, 2H), 1.61 (pent, J=6.9 Hz, 2H), 1.38-1.24 (m, 6H), 0.86 (t, J=6.6 Hz, 3H). $^{13}$C NMR for 0-C$_7$TMM (75 MHz, D$_2$O): δ 176.81, 93.37, 93.20, 72.49, 72.41, 72.28, 72.15, 70.93, 70.87, 69.91, 69.58, 62.86, 60.42, 33.73, 28.33, 27.84, 24.24, 21.75, 13.23. HR ESI MS positive mode for 0-C$_7$TMM: calcd. for C$_{19}$H$_{34}$O$_{12}$Na [M+Na]$^+$ m/z, 477.1948; found, 477.1966. (FIGS. 27 and 28).

Figure 29:
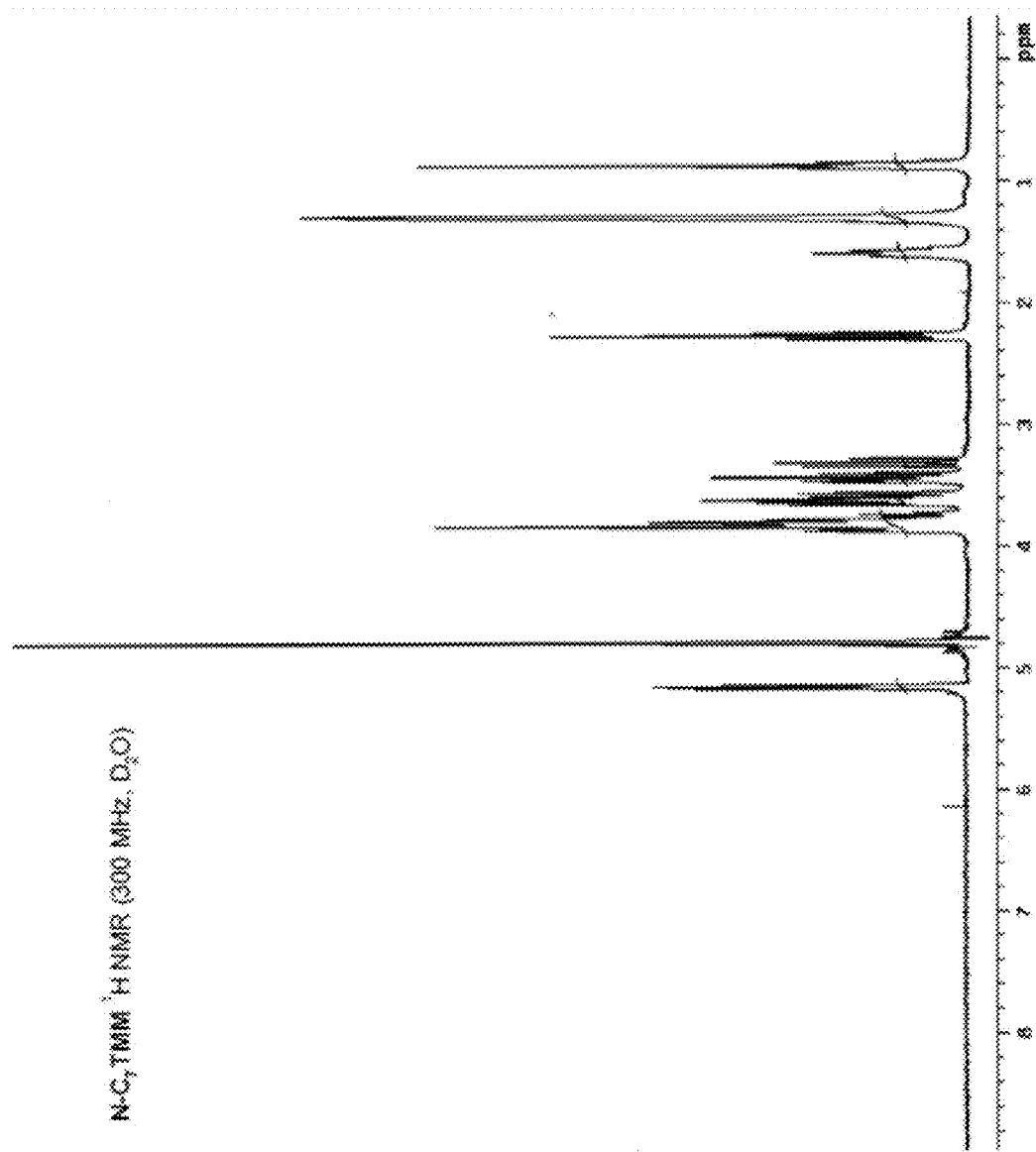
FIG. 29 shows a $^1H$ NMR spectrum of N-(6-heptanoyl)-6-amino-6-deoxy-α,α-D-trehalose (N—$C_7$TMM).
Figure 30:
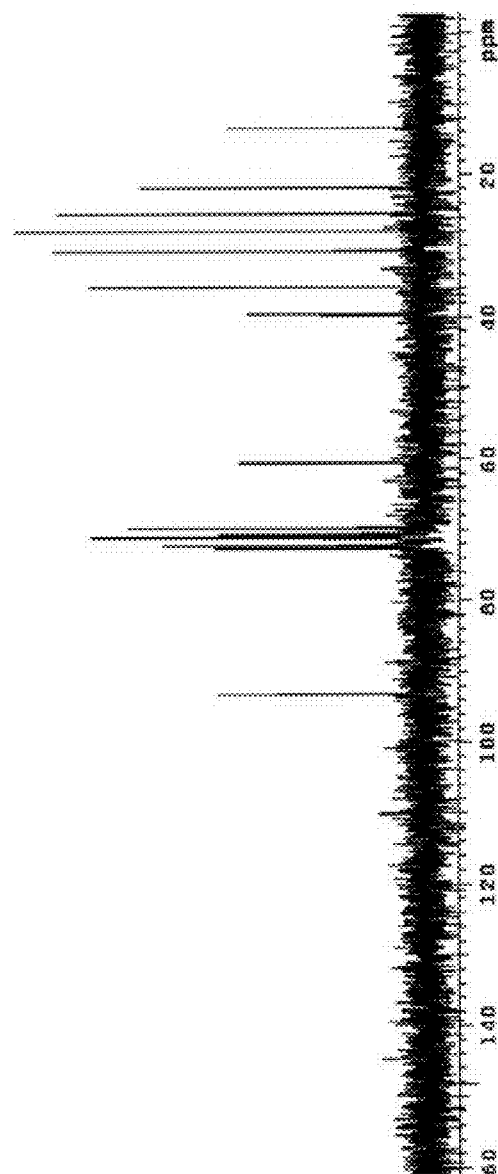
FIG. 30 shows a $^{13}C$ NMR spectrum of N—$C_7$TMM.

$^1$H NMR for N—C$_7$TMM (300 MHz, D$_2$O): δ 5.16 (d, J=4.2 Hz, 1H), 5.14 (d, J=3.3 Hz, 1H), 3.88-3.72 (m, 6H), 3.65-3.55 (m, 3H), 3.47-3.40 (m, 2H), 3.31 (t, J=9.3 Hz, 1H), 2.27 (t, J=6.9 Hz, 2H), 1.59 (pent, J=6.9 Hz, 2H), 1.33-1.64 (m, 6H), 0.87 (t, J=6.6 Hz, 3H). $^{13}$C NMR for N—C$_7$TMM (75 MHz, D$_2$O): δ 177.65, 93.12, 93.03, 72.58, 72.20, 72.14, 71.15, 71.01, 70.57, 69.62, 60.48, 39.56, 35.73, 30.63, 27.84, 25.40, 21.75, 13.26. HR ESI MS negative mode for N—C$_7$TMM: calcd. for C$_{19}$H$_{34}$NO$_{11}$ [M–H]$^-$ m/z, 452.2132; found, 452.2001. (FIGS. 29 and 30).

6-O-(4-pentynoyl)-α,α-D-trehalose (O-AlkTMM-C5)

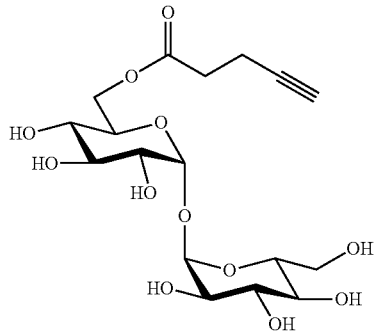

6-O-(4-pentynoyl)-α,α-D-trehalose was synthesized by similar methods as described above for O-AlkTMM and Scheme 3.

Figure 32:
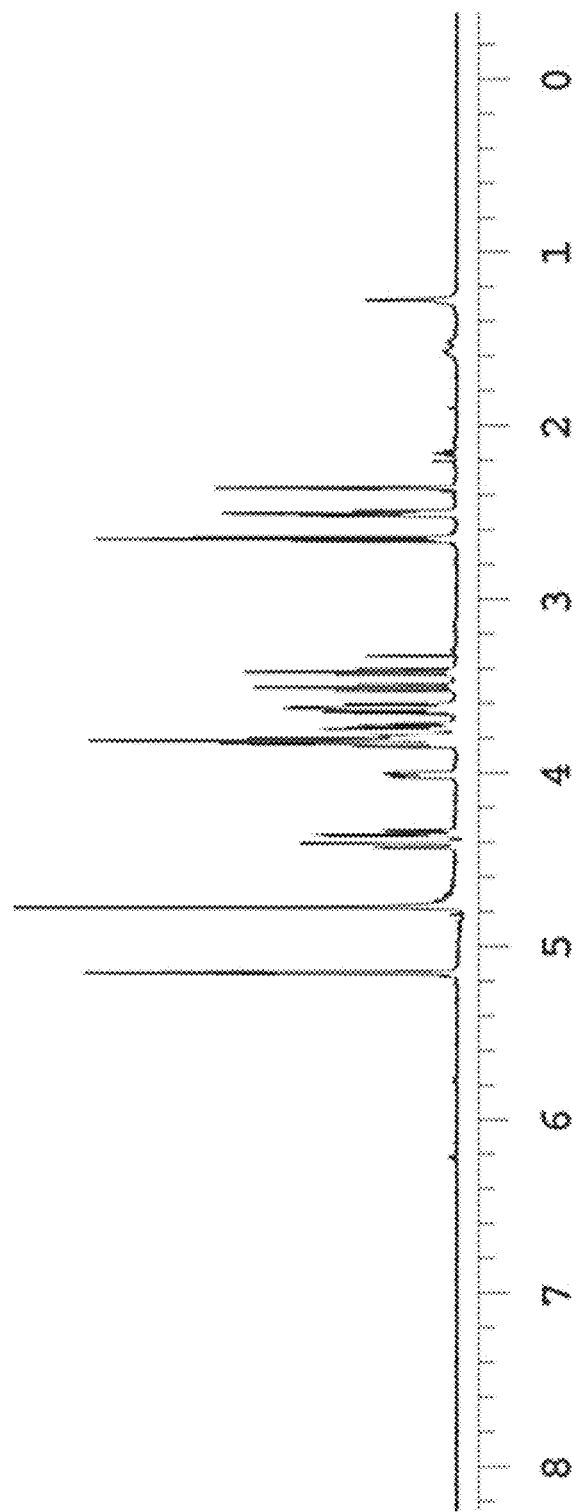
FIG. 32 shows a $^1H$ NMR spectrum of 6-O-(4-pentynoyl)-α,α-D-trehalose (O-AlkTMM-C5).
Figure 33:
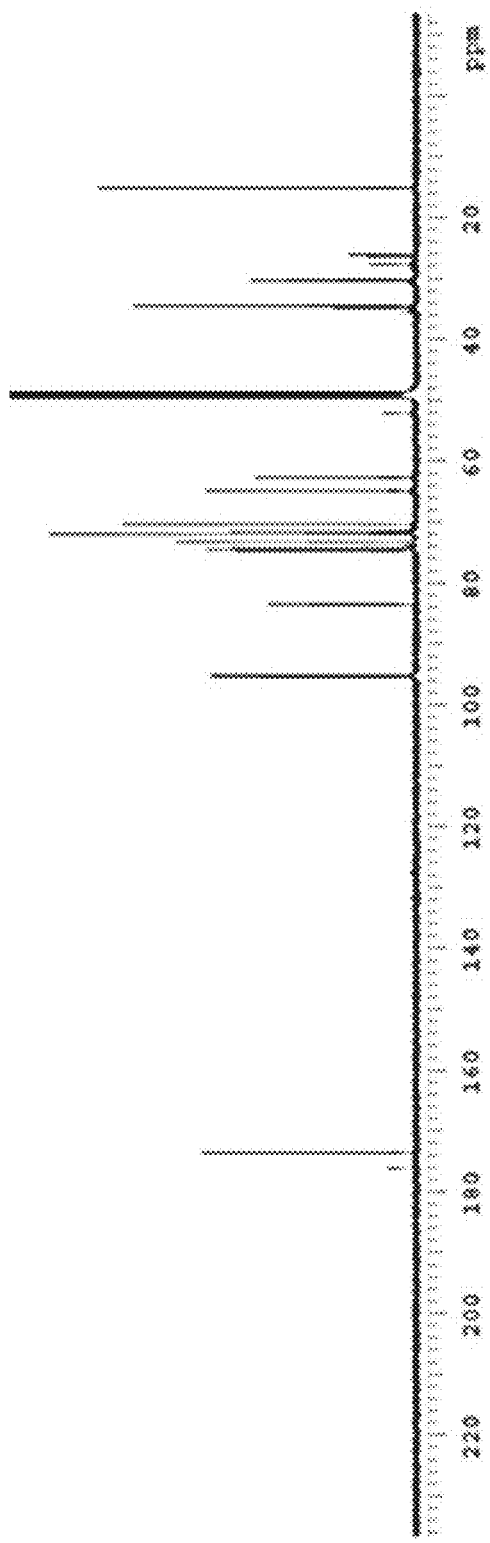
FIG. 33 shows a $^{13}C$ NMR spectrum of 6-O-(4-pentynoyl)-α,α-D-trehalose.

From 200 mg of compound 7, obtained 40 mg (36% over two steps). $^1$H NMR (500 MHz, D$_2$O): δ 5.16 (d, J=3.0 Hz, 1H, H-1'), 5.15 (d, J=3.5 Hz, 1H, H-1), 4.42 (dd, J=2.0, 12 Hz, 1H, H-6a' or 6b'), 4.35 (dd, J=5.0, 12 Hz, 1H, H-6a' or 6b'), 4.01 (ddd, J=2.0, 4.5, 10.5 Hz, 1H, H-5'), 3.85-3.78 (m, 4H, H-3, 3', 5, 6a or 6b), 3.73 (dd, J=5.0, 12 Hz, 1H, H-6a or 6b), 3.63 (t, J=11 Hz, 1H, H-2'), 3.62 (t, J=11.5 Hz, 1H, H-2), 3.51 (t, J=10 Hz, 1H, H-4'), 3.42 (t, J=9.0 Hz, 1H, H-4), 2.66 (t, J=7.0 Hz, 2H, α-CH$_2$), 2.51 (dt, J=2.5, 7.0 Hz, 2H, propargylic CH$_2$), 2.36 (t, J=2.5 Hz, 1H, terminal alkyne H). $^{13}$C NMR (125 MHz, CD$_3$OD): δ 173.6, 95.4, 95.2, 83.5, 74.7, 74.6, 74.0, 73.3, 73.2, 72.0, 71.5, 70.4, 64.9, 62.7, 34.5, 30.3, 15.1. (FIGS. 32 and 33) HR ESI MS negative mode: calcd. for C$_{17}$H$_{25}$O$_{12}$ [M–H]$^-$: 421.1346, found: 421.1356. (Compound numbering refers to Scheme 3).

6-O-(10-undecynoyl)-α,α-D-trehalose (O-AlkTMM-C11)

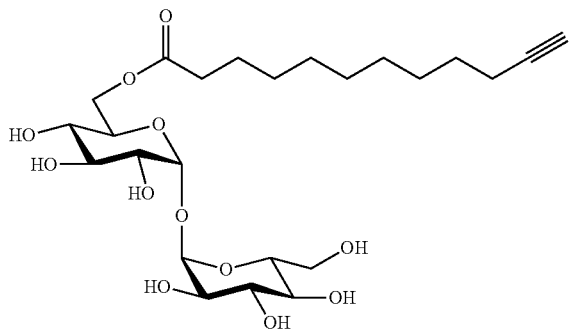

6-O-(10-undecynoyl)-α,α-D-trehalose was synthesized by similar methods as described above for O-AlkTMM and Scheme 3.

Figure 34:
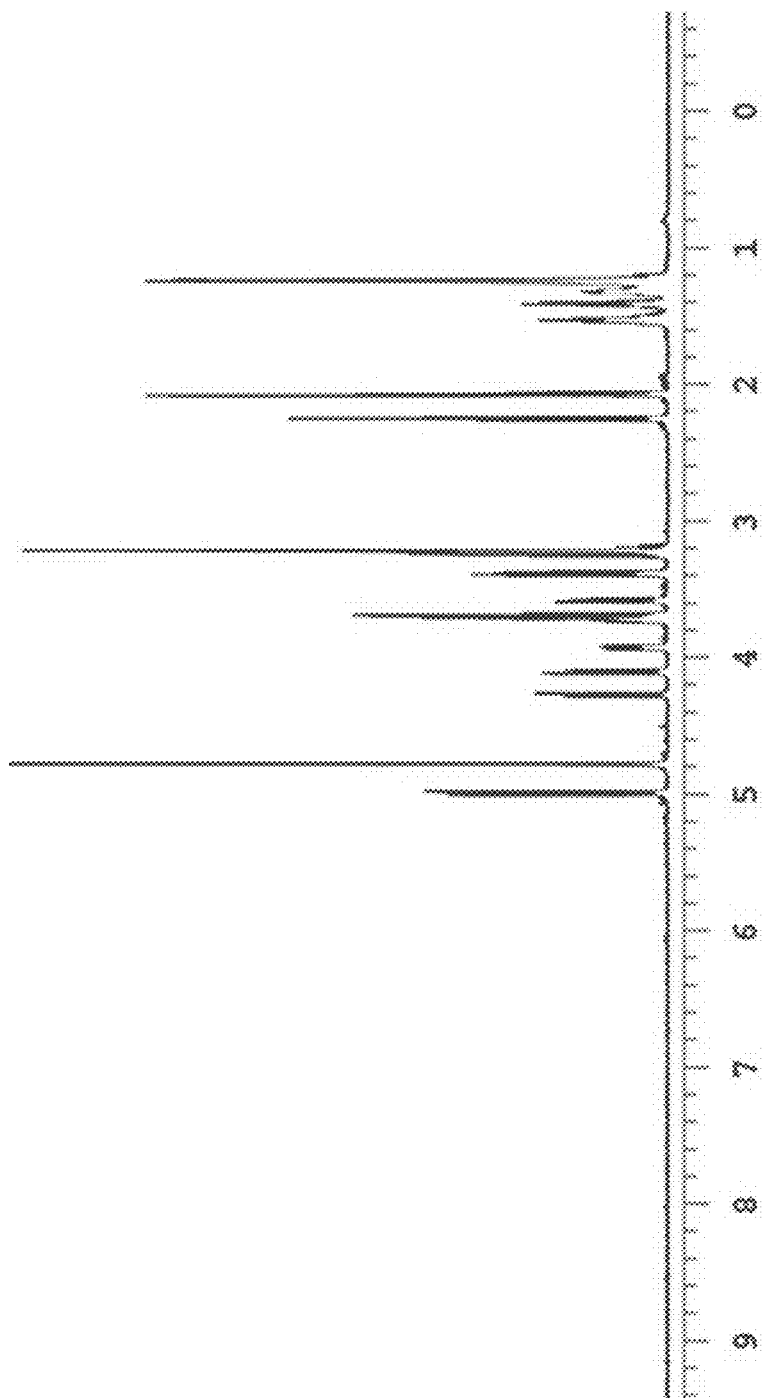
FIG. 34 shows a $^1H$ NMR spectrum of 6-O-(10-undecynoyl)-α,α-D-trehalose (O-AlkTMM-C11).
Figure 35:
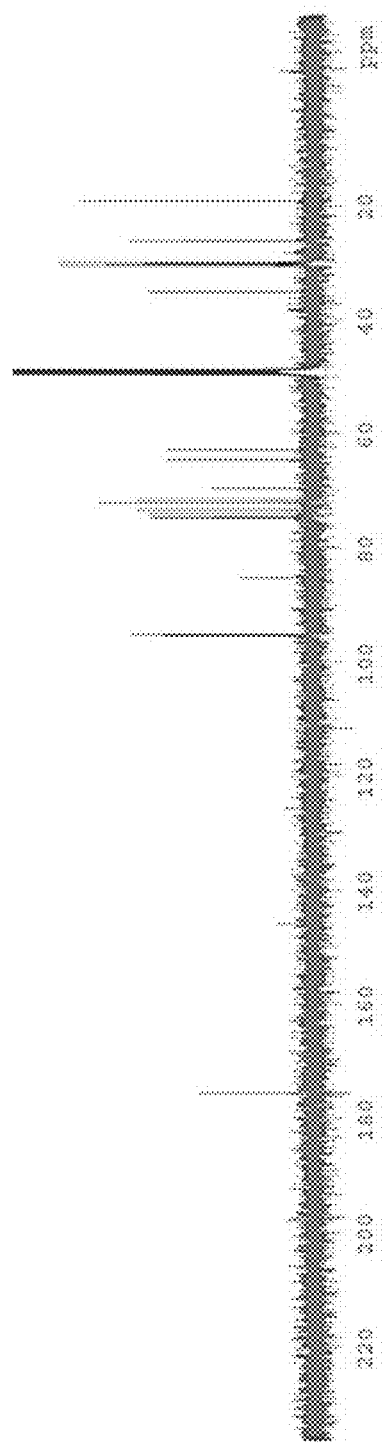
FIG. 35 shows a $^{13}C$ NMR spectrum of 6-O-(10-undecynoyl)-α,α-D-trehalose.

From 200 mg of compound 7, obtained 50 mg (38% over two steps). $^1$H NMR (500 MHz, CD$_3$OD) δ 5.01 (d, J=3.0 Hz, 1H, H-1'), 4.98 (d, J=4.0 Hz, 1H, H-1), 4.27 (dd, J=2.0, 12 Hz, 1H, H-6a' or 6b'), 4.11 (dd, J=5.0, 12 Hz, 1H, H-6a' or 6b'), 3.93 (ddd, J=2.0, 5.0, 10 Hz, 1H, H-5'), 3.75-3.66 (m, 4H, H-3, 3', 5, 6a or 6b), 3.58 (dd, J=5.5, 12 Hz, 1H, H-6a or 6b), 3.39 (t, J=5.0 Hz, 1H, H-2'), 3.37 (t, J=4.0 Hz, 1H, H-2), 3.25 (t, J=9.5 Hz, 1H, H-4'), 3.23-3.18 (m, 1H, H-4), 2.25 (t, J=7.0 Hz, 2H, α-CH$_2$), 2.09-2.05 (m, J=2 3, propargylic CH$_2$ and terminal alkyne H), 1.53 (pent, J=7.5 Hz, 2H, (3-CH$_2$), 1.41 (pent, J=7.0 Hz, 2H, homopropargylic CH$_2$), 1.33-1.23 (m, 10H, CH$_2$s). $^{13}$C NMR (125 MHz, CD$_3$OD): δ 175.6, 95.3, 95.2, 85.2, 74.7, 74.6, 74.0, 73.3, 73.2, 72.0, 72.0, 71.5, 69.5, 64.5, 62.7, 35.1, 30.4, 30.3, 30.2, 29.9, 29.8, 26.2, 19.1. (FIGS. 34 and 35) HR ESI MS negative mode: calcd. for C$_{23}$H$_{37}$O$_{12}$ [M–H]$^-$: 505.2285, found: 505.2292. (Compound numbering refers to Scheme 3).

6-O-(5-azidopentanoyl)-α,α-D-trehalose

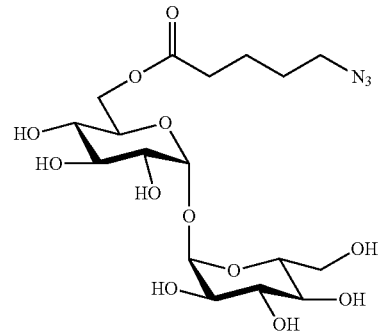

6-O-(5-azidopentanoyl)-α,α-D-trehalose was synthesized by similar methods as described above for O-AlkTMM and Scheme 3.

Figure 36:
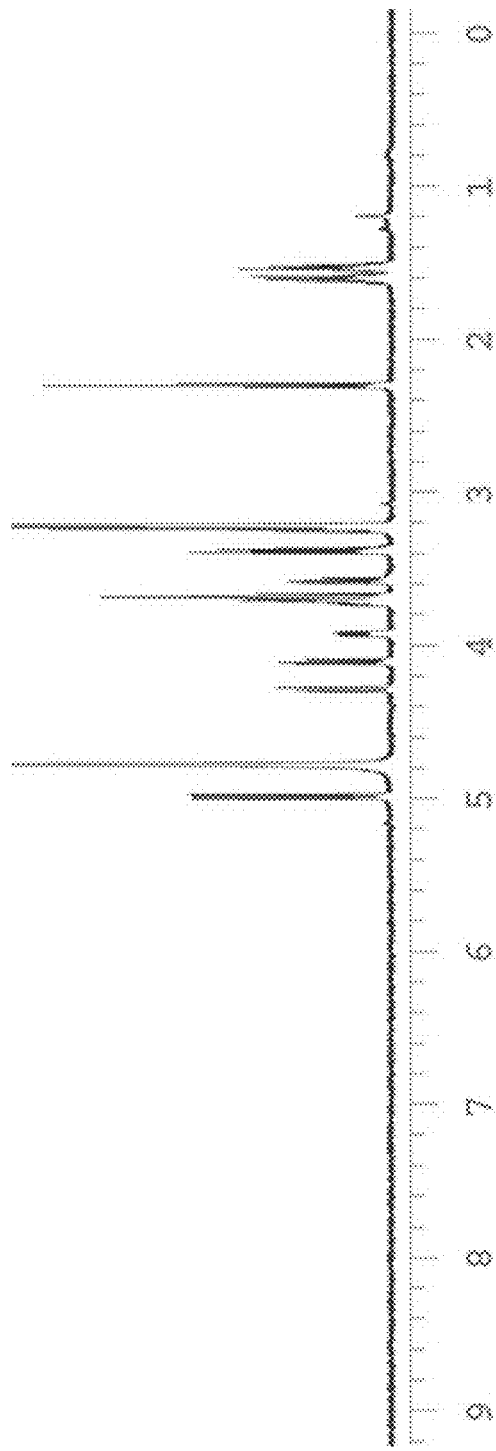
FIG. 36 shows a $^1H$ NMR spectrum of 6-O-(5-azidopentanoyl)-α,α-D-trehalose.
Figure 37:
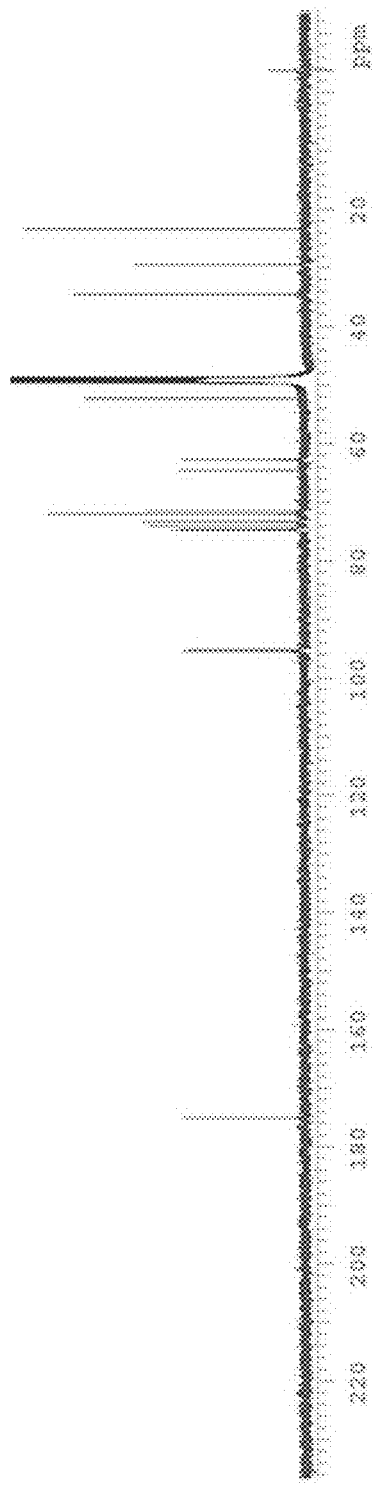
FIG. 37 shows a $^{13}C$ NMR spectrum of 6-O-(5-azidopentanoyl)-α,α-D-trehalose.

$^1$H NMR (500 MHz, CD$_3$OD): δ 5.00 (d, J=3.5 Hz, 1H, H-1'), 4.98 (d, J=3.5 Hz, 1H, H-1), 4.29 (dd, J=2.0, 12 Hz, 1H, H-6a' or 6b'), 4.11 (dd, J=5.0, 11.5 Hz, 1H, H-6a' or 6b'), 3.93 (ddd, J=2.0, 5.0, 10 Hz, 1H, H-5'), 3.76-3.66 (m, 4H, H-3, 3', 5, 6a or 6b), 3.63 (dd, J=5.0, 7.0 Hz, 1H, H-6a or 6b), 3.39 (t, J=4.5 Hz, 1H, H-2'), 3.37 (t, J=4.5 Hz, 1H, H-2), 3.26-3.20 (m, 4H, H-4, 4', CH$_2$—N$_3$), 2.30 (t, J=7.0 Hz, 2H, α-CH$_2$), 1.63-1.51 (m, 4H, CH$_2$s). $^{13}$C NMR (125 MHz, CD$_3$OD): δ 175.1, 95.4, 95.2, 74.8, 74.6, 74.0, 73.3, 73.3, 72.0, 71.5, 64.6, 62.8, 52.3, 34.5, 29.4, 23.4. (FIGS. 36 and 37).

6-O-(10-azidodecanoyl)-α,α-D-trehalose (O-Az-TMM-C10)

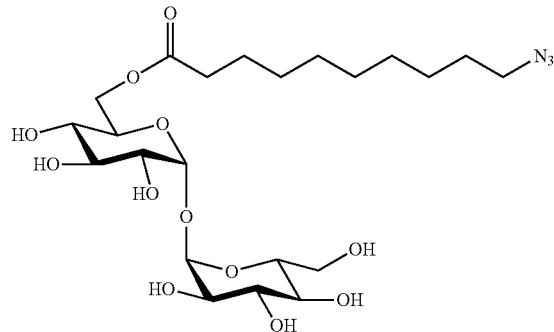

6-O-(10-azidodecanoyl)-α,α-D-trehalose was synthesized by similar methods as described above for O-AlkTMM and Scheme 3.

Figure 38:
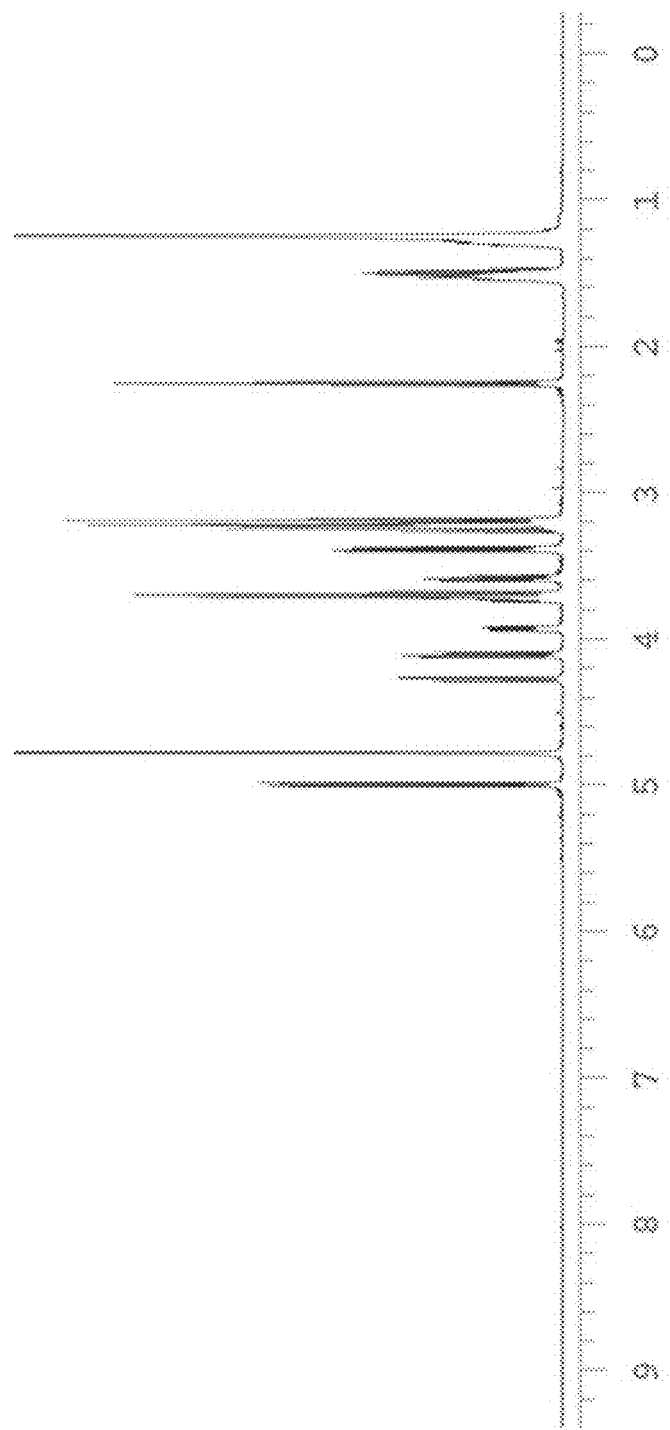
FIG. 38 shows a $^1H$ NMR spectrum of 6-O-(10-azidodecanoyl)-α,α-D-trehalose (O-AzTMM-C10).
Figure 39:
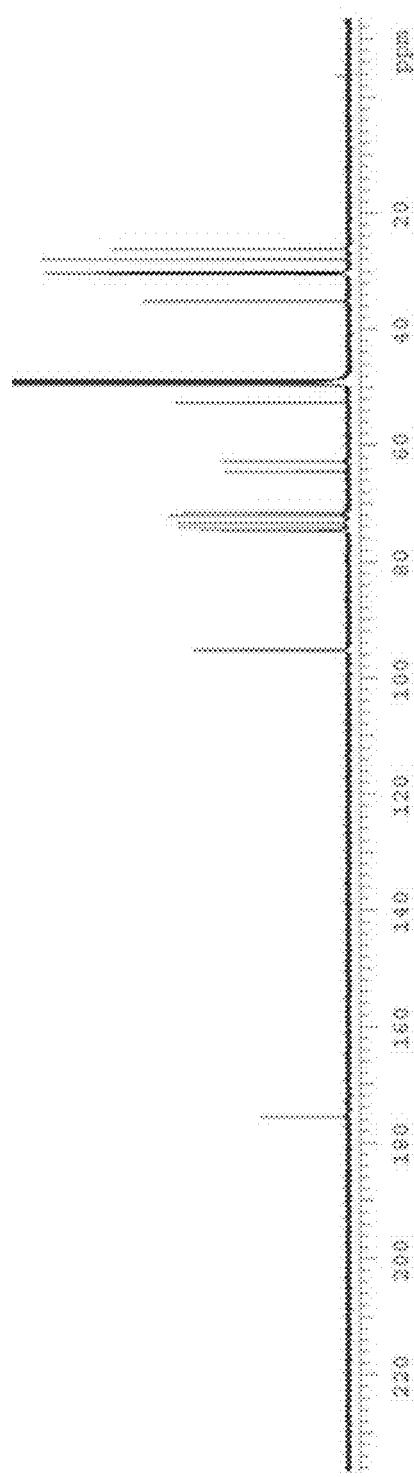
FIG. 39 shows a $^{13}C$ NMR spectrum of 6-O-(10-azidodecanoyl)-α,α-D-trehalose.

From 200 mg of compound 7, obtained 48 mg (44% over two steps). $^1$H NMR (500 MHz, CD$_3$OD): δ 5.01 (d, J=4.0 Hz, 1H, H-1'), 4.98 (d, J=4.0, 1 H, H-1), 4.29 (dd, J=2.5, 12 Hz, 1H, H-6a' or 6b'), 4.11 (dd, J=4.5, 11.5 Hz, 1H, H-6a' or 6b'), 3.93 (ddd, J=2.0, 5.0, 10.5 Hz, 1H, H-5'), 3.75-3.68 (m, 4H, H-3, 3', 5, 6a or 6b), 3.60 (dd, J=5.5, 12 Hz, 1H, H-6a or 6b), 3.40 (t, J=4.0 Hz, 1H, H-2'), 3.38 (t, J=4.5 Hz, 1H, H-2), 3.27-3.17 (m, 4H, H-4, 4', CH$_2$—N$_3$), 2.26 (t, J=7.5 Hz, 2H, α-CH$_2$), 1.55-1.47 (m, 4H, CH$_2$s), 1.31-1.25 (m, 10H, CH$_2$s). $^{13}$C NMR (125 MHz, CD$_3$OD): δ 175.6, 95.3, 95.2, 74.7, 74.6, 74.0, 73.3, 73.3, 72.0, 72.0, 71.5, 64.5, 62.7, 52.6, 35.1, 30.6, 30.4, 30.3, 30.2, 30.0, 27.9, 26.2. (FIGS. 38 and 39) HR ESI MS negative mode: calcd. for C$_{23}$H$_{40}$N$_3$O$_{14}$ [M+CHO$_2^-$]$^-$: 582.2510, found: 582.2529. (Compound numbering refers to Scheme 3).

6-O-(10-aminodecanoyl)-α,α-D-trehalose

Figure 55:
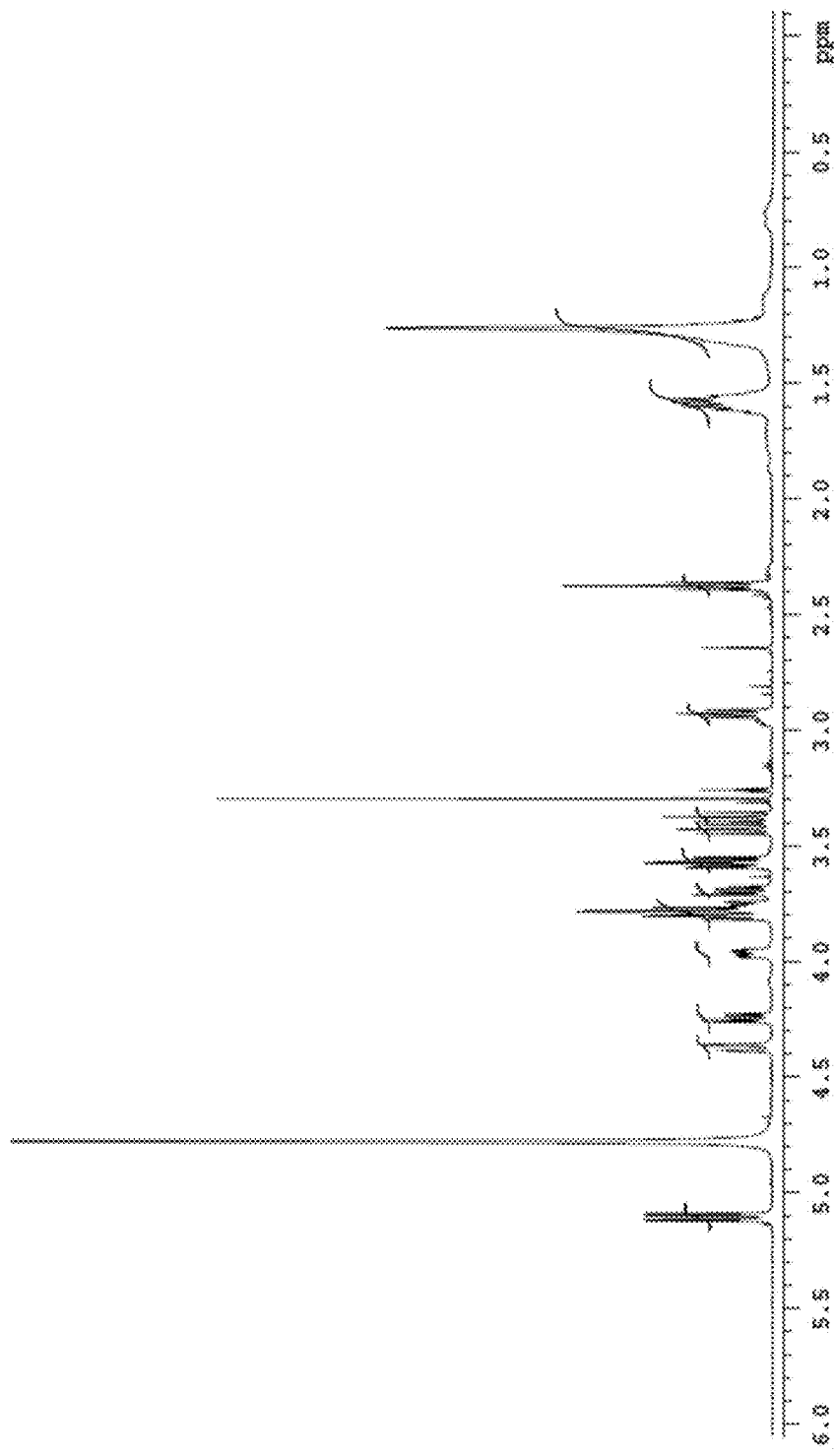
FIG. 55 shows a $^1H$ NMR spectrum of 6-O-(10-aminodecanoyl)-α,α-D-trehalose.
Figure 56:
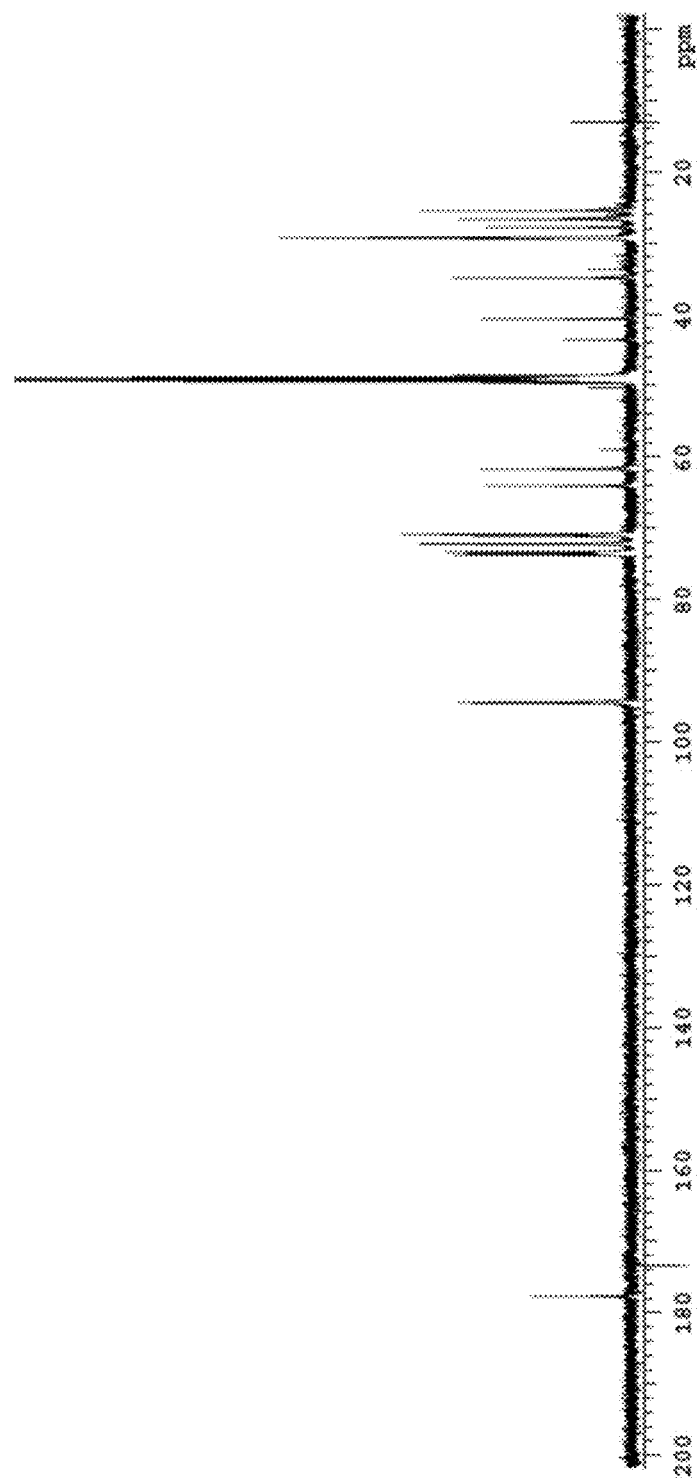
FIG. 56 shows a $^{13}$C NMR spectrum of 6-O-(10-aminodecanoyl)-α,α-D-trehalose.

To a solution of compound 4 (51 mg, 0.095 mmol) in CH$_3$OH under an argon atmosphere was added Pd/C (35 mg). A hydrogen-filled balloon was connected to the reaction flask and the argon atmosphere was exchanged for hydrogen. After stirring under a hydrogen atmosphere at room temperature overnight, the reaction mixture was filtered through Celite and the filtrate was concentrated by rotary evaporation to give the reduced product 8 (48 mg, 99%) as a white solid. $^1$H NMR (500 MHz): δ 5.16 (d, J=4.0 Hz, 1H, H-1'), δ 5.14 (d, J=4.0 Hz, 1H, H-1), 4.42 (dd, J=2.0, 12 Hz, 1H, H-6'a or b), δ 4.30 (dd, J=5.0, 12 Hz, 1H, H-6'a or b), 4.01 (ddd, J=2.0, 5.0, 10 Hz, 1H, H-5'), 3.86-3.78 (m, 4H, H-3', 3, 5, 6a or 6b), 3.74 (dd, J=5.0, 12 Hz, 1H, H6a or b), 3.63 (dd, J=4.0, 9.5 Hz, 1H, H-2'), 3.61 (dd, J=4.0, 10 Hz, 1H, H-2), 3.48 (t, J=10 Hz, 1H, H-4'), 3.42 (t, J=10 Hz, 1H, H-4), 2.97 (t, J=8.0 Hz, 2H, CH$_2$—NH$_2$), 2.42 (t, J=7.5 Hz, 2H, α-CH$_2$), 1.67-1.59 (m, 4H, CH$_2$s), 1.38-1.26 (m, 10H, CH$_2$s). $^{13}$C NMR (125 MHz, D$_2$O): 177.9, 94.7, 94.6, 73.9, 73.7, 73.5, 72.4, 72.3, 71.3, 71.1, 71.0, 64.3, 61.9, 40.8, 35.1, 29.7, 29.6, 29.5, 29.4, 28.0, 26.9, 25.6. (FIGS. 55 and 56) HR ESI MS positive mode: calcd. for C$_{22}$H$_{42}$NO$_{12}$ [M+H]$^+$: 512.2707, found: 512.2699. (Compound numbering refers to Scheme 3).

6-O-{10-{N-[(E)-cylcooct-4-enlyloxy]carbonyl}aminodecanoyl)-α,α-D-trehalose (O-TCO-TMM)

Figure 57:
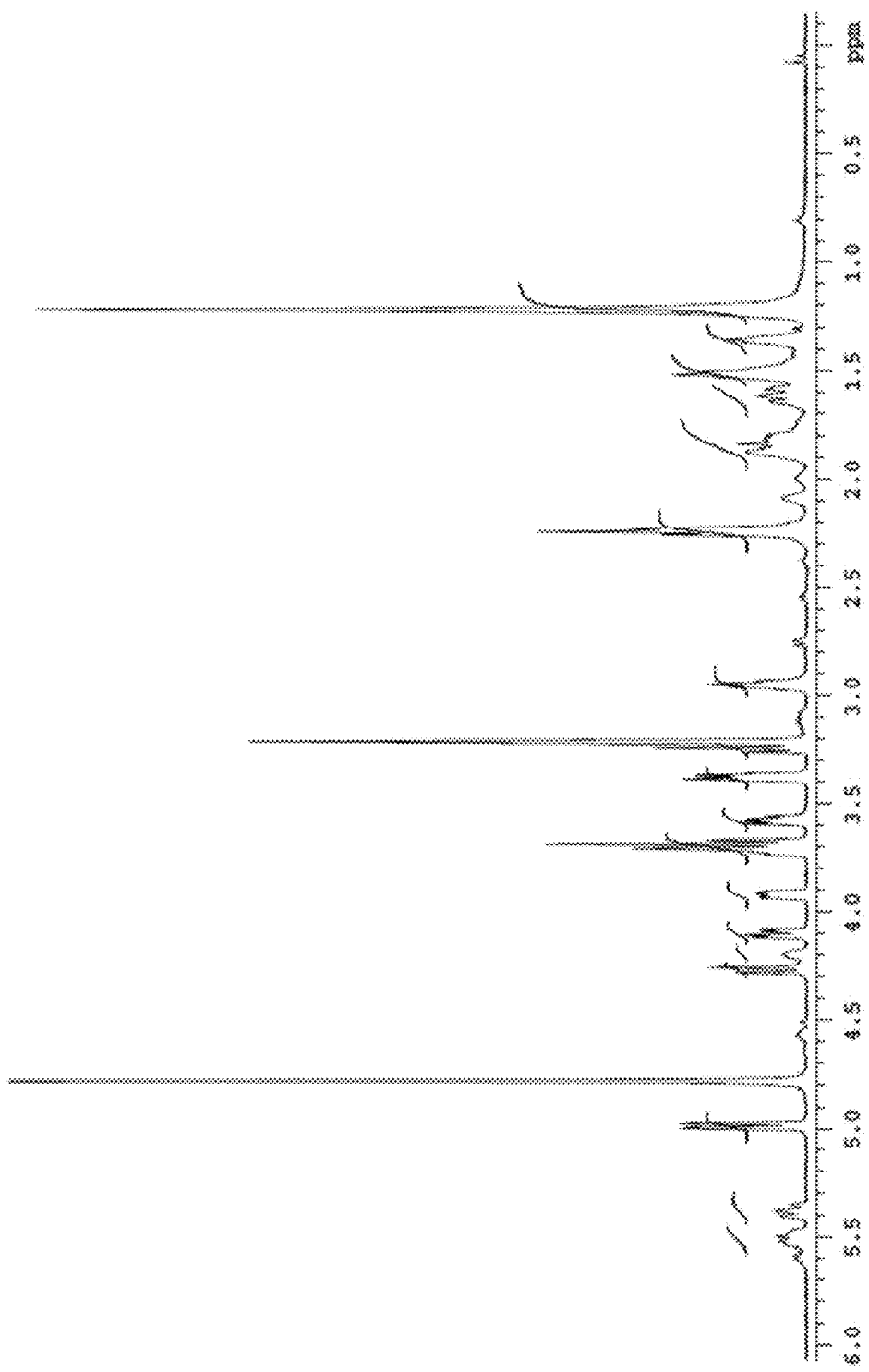
FIG. 57 shows a $^1$H NMR spectrum of 6-O-(10-{N-[(E)-cylcooct-4-enlyloxy]carbonyl}aminodecanoyl)-α,α-D-trehalose (O-TCO-TMM).
Figure 58:
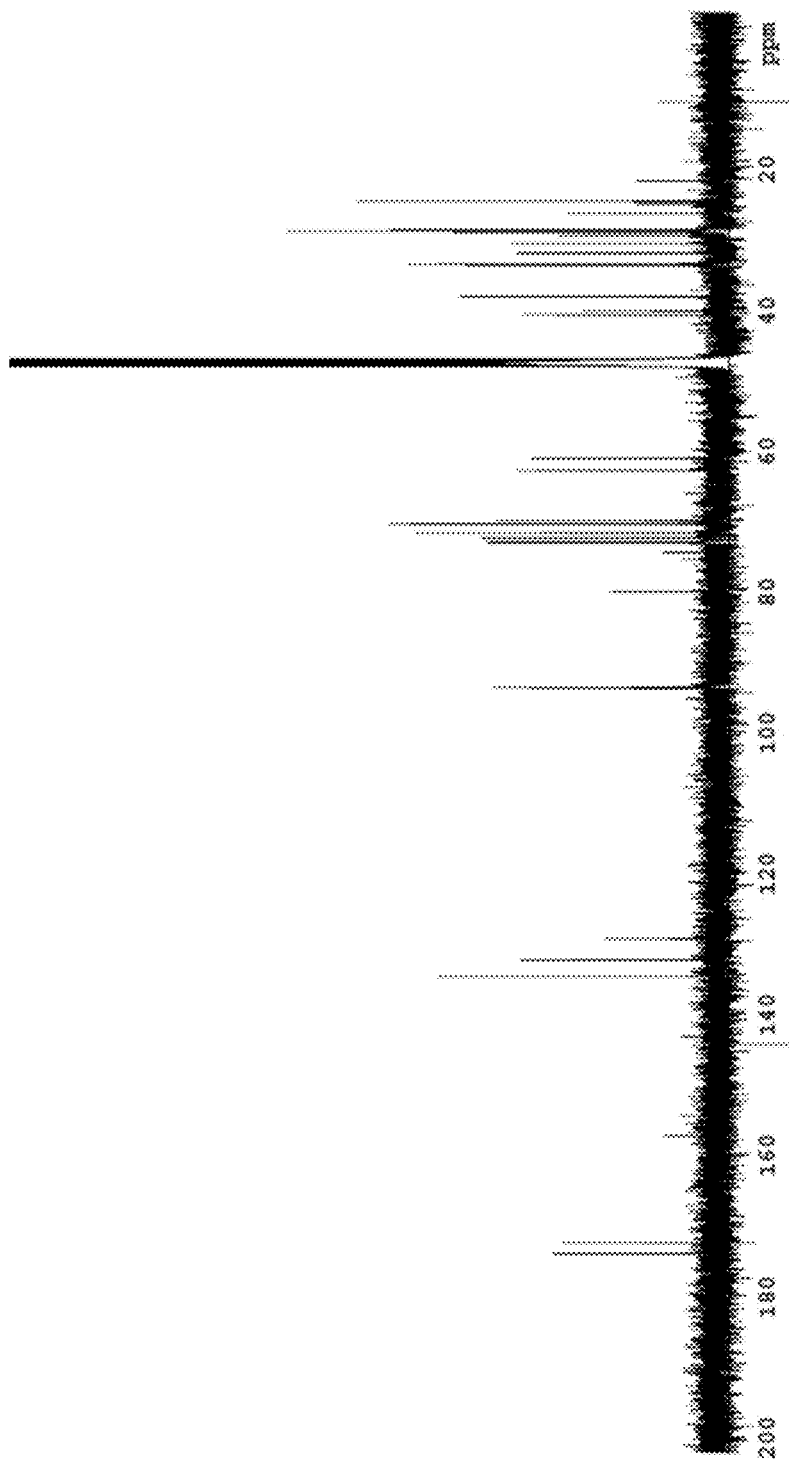
FIG. 58 shows a $^{13}$C NMR spectrum of 6-O-(10-{N-[(E)-cylcooct-4-en1lyloxy]carbonyl}aminodecanoyl)-α,α-D-trehalose.

To a 20 mL glass scintillation vial containing compound 8 (23 mg, 0.045 mmol) stirring in CH$_3$OH (1.0 mL) was added a solution of (E)-cyclooct-4-enyl 2,5-dioxo-1-pyrrolidinyl carbonate (TCO-NHS, 11.5 mg, 0.0435 mmol) and Et$_3$N (7 µL, 0.05 mmol) dissolved in N,N-dimethylformamide (DMF) (2.5 mL). After stirring for 20 h, the reaction mixture was concentrated by rotary evaporation and purified using a Biotage Isolera One automated flash chromatography system (10 g C18 column; 20% CH$_3$CN in H$_2$O→100% CH$_3$CN) to give product 5 (18.5 mg, 62%). $^1$H NMR (500 MHz, CD$_3$OD) δ 5.57-5.35 (m, 2H, TCO vinyl-CH), 5.00 (d, J=3.5 Hz, 1H, H-1'), 4.98 (d, J=3.0 Hz, 1H, H-1), 4.27 (dd, J=2.0, 12 Hz, 1H, H-6a' or 6b'), 4.22-4.16 (m, 2H, TCO CH), 4.10 (dd, J=5.0, 12 Hz, 1H, H-6a' or 6b'), 3.95-3.89 (m, 1H, H-5'), 3.74-3.66 (m, 4H, H-3, 3', 5, 6a or 6b), 3.58 (dd, J=5.5, 11 Hz, 1H, H-6a or 6b), 3.40-3.35 (m, 2H, H-2, 2'), 3.27-3.20 (m, 2H, H-4, 4'), 2.96 (t, J=5.5 Hz, 2H, CH$_2$—N), 2.27-2.19 (m, 4H, α-CH$_2$, TCO allylic CH$_2$), 1.92-1.77 (m, 4H, TCO CH$_2$s), 1.61 (pent, J=12.5 Hz, 2H, TCO CH$_2$), 1.56-1.46 (m, 4H, (3-CH$_2$, TCO CH$_2$), 1.37-1.35 (m, 2H, CH$_2$), 1.26-1.16 (m, 10H, CH$_2$s). $^{13}$C NMR (125 MHz, CD$_3$OD): δ 174.0, 172.5, 134.6, 132.3, 93.7, 93.6, 80.1, 73.2, 73.0, 72.5, 71.8, 71.7, 70.5, 70.4, 70.0, 62.9, 61.2, 40.8, 40.2, 38.2, 33.8, 33.6, 32.1, 30.7, 29.6, 29.1, 29.0, 28.9, 28.7, 26.4, 24.6. (FIGS. 57 and 58) HR ESI MS positive mode: m/z calcd. for C$_{31}$H$_{54}$NO$_{14}$ [M+H]+: 664.3544, found: 664.3521. (Compound numbering refers to Scheme 3).

6-O-(10-[(fluorescein-5-yl)thioureido]decanoyl)-α,α-D-trehalose (O-FITC-TMM)

Figure 59:
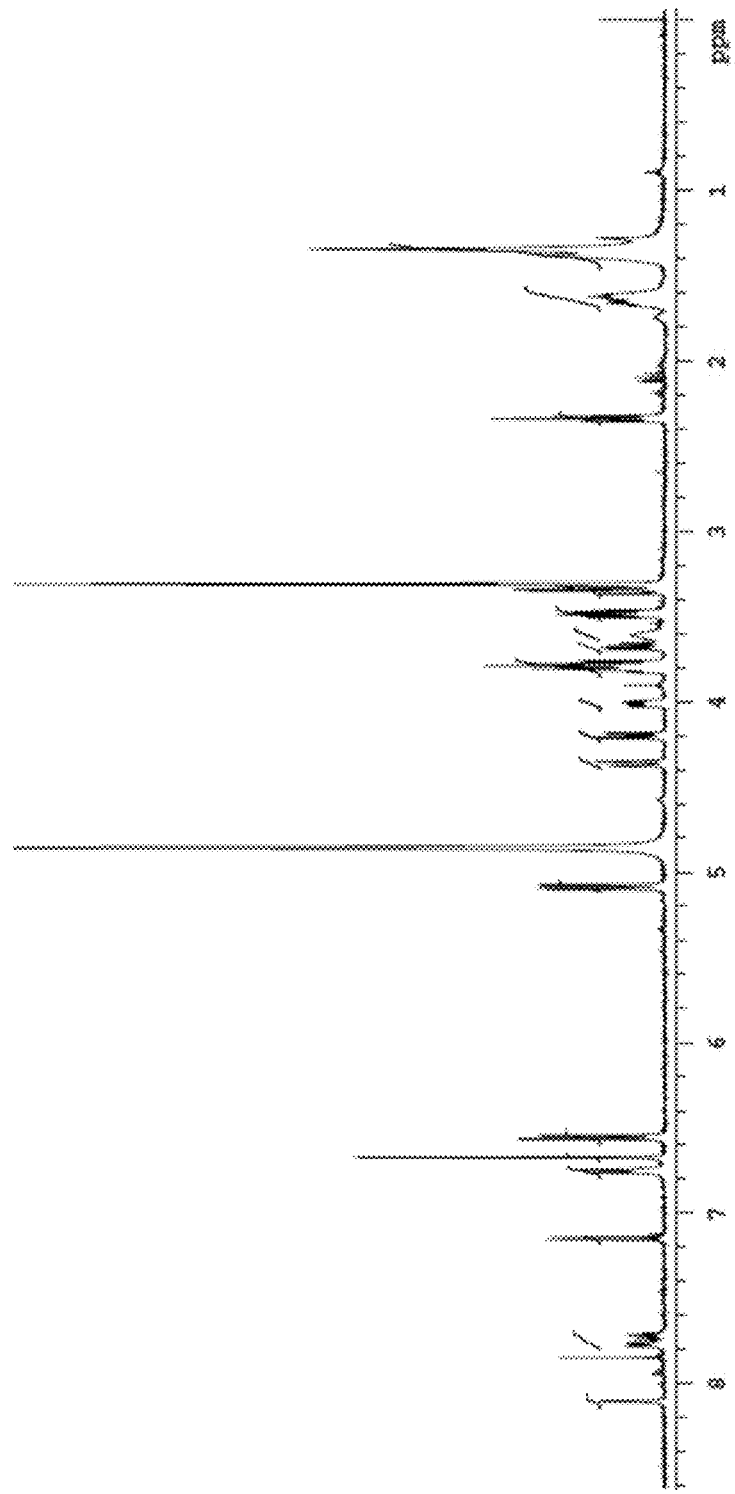
FIG. 59 shows a $^1$H NMR spectrum of 6-O-(10-[(fluorescein-5-yl)thioureido]decanoyl)-α,α-D-trehalose (O-FITC-TMM).
Figure 60:
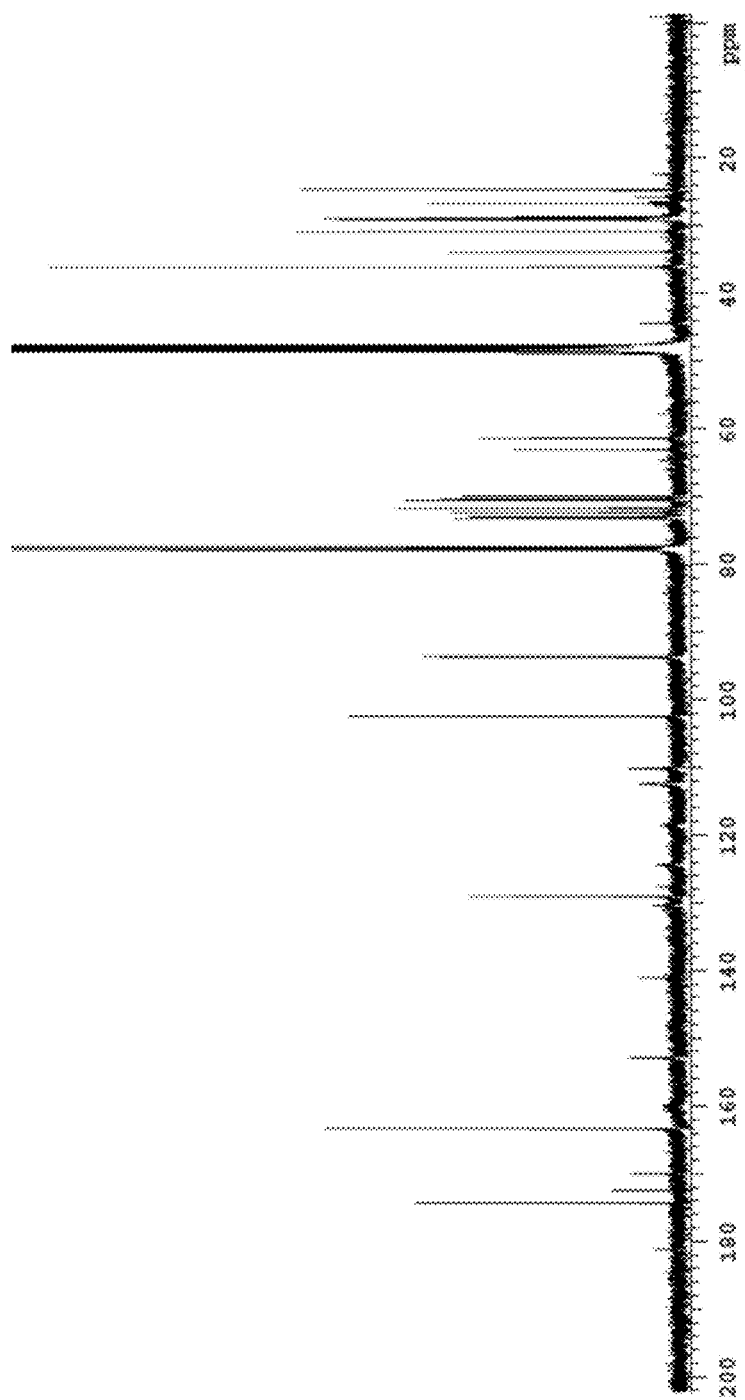
FIG. 60 shows a $^{13}$C NMR spectrum of 6-O-(10-[(fluorescein-5-yl)thioureido]decanoyl)-α,α-D-trehalose.

To a 20 mL glass scintillation vial containing compound 8 (15.7 mg, 0.0306 mmol) stirring in CH$_3$OH (0.5 mL) was added a solution of fluorescein isothiocyanate (FITC, 12.4 mg, 0.316 mmol) and Et$_3$N (7 µL, 0.05 mmol) dissolved in N,N-dimethylformamide (DMF) (1.5 mL). After stirring for 20 h, the reaction mixture was concentrated by rotary evaporation and purified using a Biotage Isolera One automated flash chromatography system (10 g C18 column; 30% CH$_3$CN in H$_2$O→70% CH$_3$CN in H$_2$O) to give product 6 (23.4 mg, 85%) as a yellow solid. $^1$H NMR (500 MHz, 10% CDCl$_3$ in CD$_3$OD) δ 8.18 (s, broad, 1H, FITC Ar—CH), 7.86 (dd, J=2.0, 8.5 Hz, 1H, FITC Ar—CH), 7.16 (d, J=8.5 Hz, 1H, FITC Ar—CH), 6.71-6.69 (m, 4H, FITC Ar—CH), 6.56 (dd, J=2.5, 9.0 Hz, 2H, FITC Ar—CH), 5.14 (d, J=4.0 Hz, 1H, H-1'), 5.11 (d, J=3.5 Hz, 1H, H-1), 4.38 (dd, J=2.0, 12 Hz, 1H, H-6a' or 6b'), 4.26 (dd, J=5.5, 12.5 Hz, 1H, H-6a' or 6b'), 4.03 (ddd, J=2.0, 4.5, 10 Hz, 1H, H-5'), 3.85-3.78 (m, 4H, H-3, 3', 5, 6a or 6b), 3.71 (dd, J=6.0, 12 Hz, 1H, H-6a or 6b), 3.67-3.60 (m, 2H, CH$_2$—N), 3.55 (dd, J=3.5, 10 Hz, 1H, H-2'), 3.51 (dd, J=4.0, 10 Hz, 1H, H-2), 3.42-3.36 (m, 2H, H-4, 4'), 2.37 (t, J=7.5 Hz, 2H, α-CH$_2$), 1.70-1.63 (m, 4H, CH$_2$s), 1.44-1.30 (m, 10H, CH$_2$s). $^{13}$C NMR (125 MHz, CD$_3$OD): δ 181.2, 175.2, 173.4, 170.9, 153.8, 142.0, 130.0, 113.4, 111.1, 103.3, 94.6, 94.5, 74.1, 73.9, 73.2, 72.6, 72.5, 71.4, 71.3, 70.8, 63.9, 62.3, 34.8, 30.2, 30.1, 30.0, 29.9, 29.6, 27.7, 25.7. (FIGS. 59 and 60) HR ESI MS positive mode: m/z calcd. for C$_{43}$H$_{53}$N$_2$O$_{17}$S [M+H]$^+$: 901.3065, found: 901.3084. (Compound numbering refers to Scheme 3).

Diazirine-Containing Compounds

The diazirine-containing compounds were prepared from the corresponding 6-trehalosamine and a bifunctional fatty acid bearing alkyne and diazirine groups using peptide coupling conditions as described for the alkyne-containing compound I-a. Similar methods are described in Haberkant et al., In vivo profiling and visualization of cellular protein-lipid interactions using bifunctional fatty acids. *Angew*

Example 2

Metabolic Labeling & Analysis of Bacteria—1

Methods

Bacterial Strains, Media, and Reagents.

The bacterial strains used herein included Msmeg mc$^2$155 wild type, Msmeg mc$^2$155 ΔsugC, *Corynebacterium glutamicum* 534, *Escherichia coli* K12 MG1655, and *Bacillus subtilis* 168.

Msmeg was cultured in Middlebrook 7H9 liquid medium supplemented with ADC (albumin, dextrose, and catalase), 0.5% glycerol, and 0.05% Tween-80. *C. glutamicum*, *E. coli*, and *B. subtilis* were cultured in LB liquid medium. All bacteria were cultured at 37° C., except *C. glutamicum*, which was cultured at 30° C.

Stock solutions of synthetic O- and N-AlkTMM (and their unlabeled versions) were prepared in ultrapure H$_2$O at concentrations of 25 mM, sterile-filtered (0.2 µm), and stored at −20° C. Prior to usage in labeling experiments, stock solutions of O- and N-AlkTMM (and their unlabeled versions) were diluted to the desired concentration with the appropriate culture medium and temporarily stored at 4° C. Other reagent stocks included: Az488 (Click Chemistry Tools, 1 mM in DMSO, stored at −20° C.); Alk488 (Click Chemistry Tools, 1 mM in DMSO, stored at −20° C.); sodium ascorbate (60 mM in H$_2$O, always freshly prepared); TBTA ligand for CuAAC reactions (Click Chemistry Tools, 6.4 mM in tert-BuOH/DMSO 4:1, stored at −20° C.); CuSO$_4$ (50 mM in H$_2$O, stored at −20° C.); DBCO-biotin (Click Chemistry Tools, 1 mM in DMSO, stored at −20° C.); avidin-Texas Red conjugate (Life Technologies, 1 mg/mL in PBS 1×, stored at −20° C.); ebselen (Cayman Chemical, 2 mg/mL in ethanol, stored at −20° C.).

General Procedures for Bacterial Labeling.

Starter cultures of bacteria were generated by inoculating a single colony from a freshly streaked LB agar plate into 3 mL liquid medium in a culture tube. Starter cultures were incubated at 37° C. (or 30° C. for *C. glutamicum*) with shaking until reaching mid-logarithmic phase and then diluted with liquid medium to the desired density for initiating experiments.

Labeling experiments were performed either in 96-well plate format or in aerated culture tubes. For experiments in 96-well plate format, bacteria were mixed with liquid medium and probe stock solution in sterile flat-bottom 96-well plates to achieve the desired cell density and probe concentration at a final volume of 200 µL. Plates were incubated at 37° C. (or 30° C. for *C. glutamicum*) with shaking in a Tecan plate reader (Infinite F200 PRO operated by Tecan iControl software) until the desired end-point (typical culture time 12-16 h, end-point OD600~1.0-1.4). For experiments in aerated culture tubes, bacteria were mixed with liquid medium and probe solution in sterile tubes to achieve the desired cell density, probe concentration, and final volume. Tubes were incubated at 37° C. (or 30° C. for *C. glutamicum*) with shaking until the desired end-point.

For secondary labeling of bacteria with a fluorophore by click chemistry, a suspension of alkyne- or azide-labeled cells (200 µL) was transferred to a v-bottom 96 well plate, centrifuged (3,600 rpm, 10 min, room temperature) and washed with PBS 1× containing 0.5% bovine serum albumin (PBSB) three times. Subsequently, cells were fixed with 4% paraformaldehyde in PBS 1× for 10 minutes and washed three times with PBSB as described above. Next, cells were reacted with the appropriate fluorophore via CuAAC. A typical CuAAC reaction was carried out by resuspension of cells in PBS 1× (138 µL) and sequential addition of stock solutions of 1 mM Az488 (3 µL), 60 mM sodium ascorbate (3 µL), 6.4 mM TBTA (3 µL), and 50 mM CuSO$_4$ (3 µL) to give a final reaction volume of 150 µL and the following final reagent concentrations: Az488, 20 M; sodium ascorbate, 1.2 mM; TBTA, 128 M; CuSO$_4$, 1 mM. After thorough mixing, reactions were incubated in the dark at room temperature for 30 min. Finally, cells were washed with PBS 1× three times and prepared for analysis by flow cytometry or fluorescence microscopy.

Flow Cytometry.

After fluorescent labeling of bacteria according to the above general procedure, bacteria were transferred to 5 mL polystyrene Falcon tubes (BD Biosciences) and analyzed by flow cytometry. Flow cytometry was performed on a BD Biosciences FACSAria II flow cytometer. Fluorescence data was collected for 50,000 cells at an event rate of 500-1,000 events/sec and processed using BD FACSDIVA 8.0.1. All flow cytometry experiments were performed with three replicate samples, and data shown were representative of at least two independent experiments. Scatter-gated fluorescence analysis was used to obtain mean fluorescence intensities with doublet discrimination.

Fluorescence Microscopy.

10 µL of bacterial sample in PBS 1× were spotted onto a microscope slide, lightly spread into a thin layer using the edge of a coverslip, and allowed to air dry in the dark. Fluoromount-G mounting medium (SouthernBiotech) was applied, then cover slips were placed over the sample and immobilized with adhesive. Microscopy was carried out using an EVOS FL (Life Technologies) inverted microscope equipped with a 100×1.4 numerical aperture Plan-Apochromat oil immersion lens. Fluorescence imaging was performed using GFP (maximum excitation/emission=470/510 nm) and Texas Red (maximum excitation/emission=585/624 nm) LED light cubes. Images were captured with a Sony ICX445 CCD camera and processed using the FIJI distribution of ImageJ. Image acquisition and processing were performed identically for all test and control samples being compared. Imaging data shown were representative of at least two independent experiments.

Competition of AlkTMM labeling in Msmeg.

Figure 5:
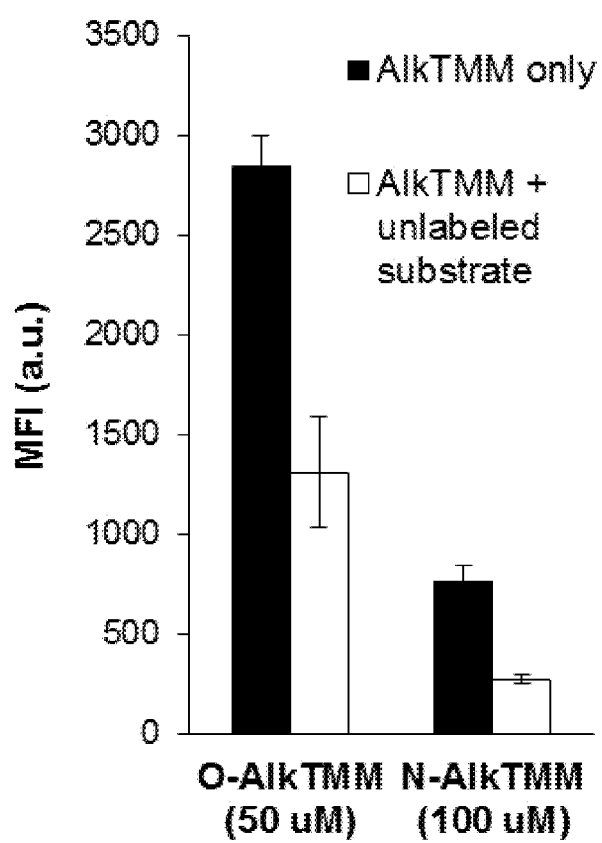
FIG. 5 shows a plot of Msmeg incubated with a disclosed compound alone or with 5 mM of competing unlabeled probes lacking alkynes.

For O-AkTMM competition experiments, Msmeg was cultured in 7H9 liquid medium in 96-well plates in the presence of O-AlkTMM (50 µM) and its unlabeled version, O—C$_7$TMM, at concentrations of 250, 1000, and 5000 µM (or without competitor) for 4 h. For N-AlkTMM competition experiments, Msmeg was cultured in 7H9 liquid medium in the presence of N-AlkTMM (100 µM) and its unlabeled version, N—C$_7$TMM, at concentrations of 250, 1000, and 5000 µM (or without competitor) for 4 h. Cells were subjected to CuAAC and analyzed by flow cytometry as described above. Dose-dependent competition of signal was observed for both O- and N-AlkTMM, and the results from the 5000 µM competition experiment are shown in FIG. 5.

Effect of Ebselen on Alk7TMM Labeling in Msmeg.

Msmeg was cultured in 7H9 liquid medium in 96-well plates in the presence of ebselen (50 µg/mL) for 8 hours, after which the chemical reporter (O-AlkTMM, 50 M; N-AlkTMM, 100 M; 6-TreAz, 25 µM) was added and the cells were incubated for another 4 hours. Cells were subjected to CuAAC and analyzed by flow cytometry as described above.

Cellular Fractionation and Analysis of Labeled Msmeg.

Figure 12:
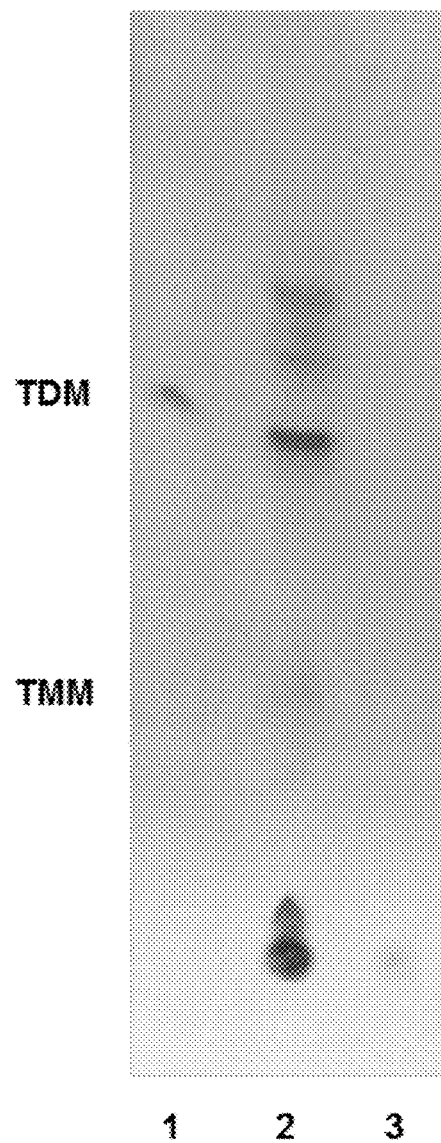
FIG. 12 shows TLC analysis of extractable lipids and PG-AGM fractions from Msmeg confirming separation of the trehalose glycolipids from AGM during $CHCl_3/CH_3OH$ extraction.
Figure 13:
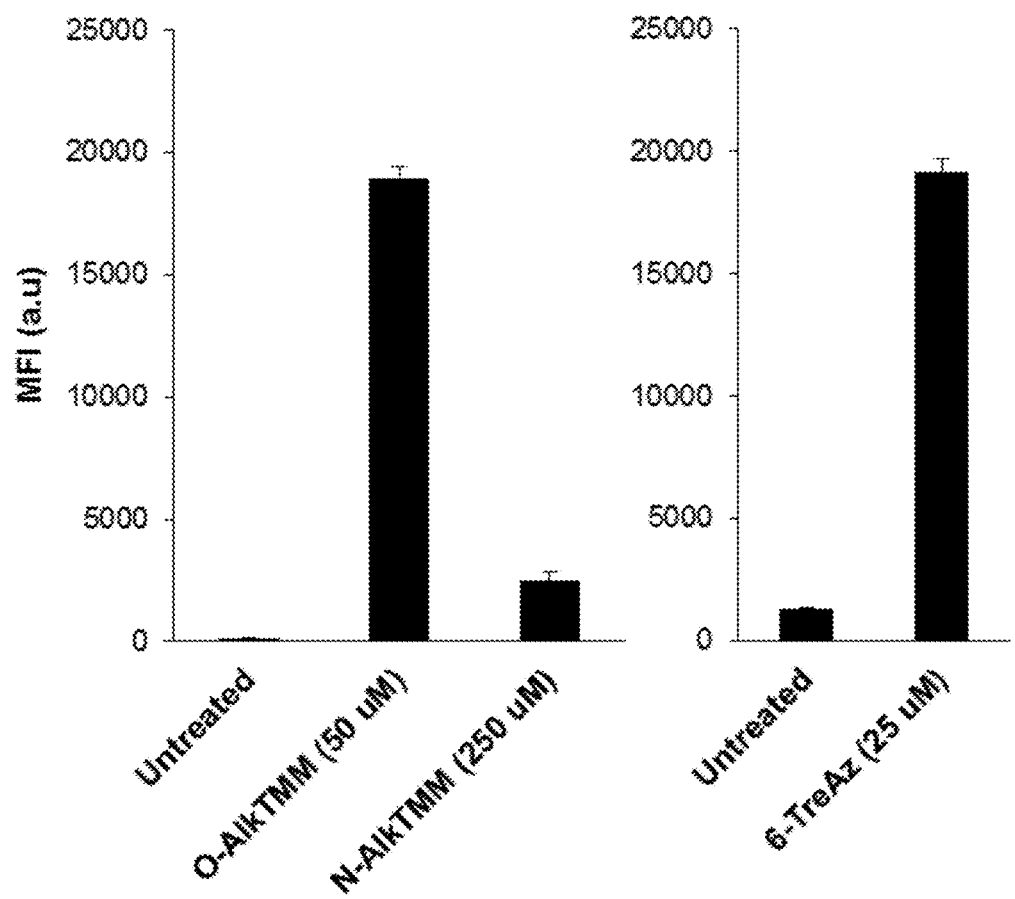
FIG. 13 shows flow cytometry analysis for intact cells prior to cellular fractionation.

10 mL Msmeg cultures were grown in 7H9 liquid medium in the presence of O-AlkTMM (50 µM), N-AlkTMM (250 µM), or left untreated in 15 mL conical tubes. A higher concentration of N-AlkTMM was used to maximize labeling efficiency. In parallel, cultures were grown in the presence of 6-TreAz (25 µM) or left S19 untreated. Cells were incubated with shaking for 4 h at 37° C. until reaching late-log phase, then pelleted by centrifugation and washed with PBSB three times as described above. For O- and N-AlkTMM-labeled cells and their untreated control, the above-described click chemistry procedure was carried out with Az488 at a reaction volume of 500 µL. For 6-TreAz-labeled cells and their untreated control, the above-described click chemistry procedure was carried out with Alk488 at a reaction volume of 500 µL. After the click reactions, cells were pelleted by centrifugation and washed with PBSB three times as described above. Aliquots were removed and resuspended in PBS 1× for measurement of OD600 (for normalization of fluorescence values) and analysis by flow cytometry as shown in FIG. 13. The remainder of the cells were resuspended in 1 mL HPLC grade $CH_3OH$ and transferred to a glass screw-cap culture tube containing 2 mL $CHCl_3$ and equipped with a stir bar. The $CHCl_3/CH_3OH$ (2:1) cell suspension was stirred overnight to accomplish separation of the soluble extractable lipids from the insoluble PG-AGM material. The insoluble material was pelleted by centrifugation (3,600 rpm, 10 minutes, room temperature) and washed two times with $CHCl_3/CH_3OH$ (2:1). The $CHCl_3/CH_3OH$ (2:1) supernatants containing soluble extractable lipids were combined in a 20 mL glass scintillation vial and dried by rotary evaporation. Both fractions were subjected to TLC analysis as described in FIG. 12 to confirm separation of the extractable lipids from the PG-AGM material. Both fractions were then resuspended in 1 mL 5% aqueous tetrabutylammonium hydroxide (TBAH) in glass screw-cap culture tubes, sealed and then stirred overnight at 100° C. to saponify and solubilize the samples. Next, the samples were cooled to room temperature and 200 µL aliquots were transferred to a black flat-bottom 96-well plate. Fluorescence analysis of samples versus a 5% aqueous TBAH blank control was carried out using a Tecan plate reader (Infinite F200 PRO operated by Tecan iControl software) using a GFP filter (excitation/emission 485/535) using the optimal gain setting.

Two-Color Fluorescence Imaging of Dual-Labeled Msmeg.

Msmeg was cultured in the presence of O-AlkTMM (50 µM) and 6-TreAz (25 M) (or controls treated with no probe, O-AlkTMM alone, or 6-TreAz alone) in 7H9 in culture tubes at 37° C. with shaking for 4 h. Cells were fixed and washed three times with PBSB as described above. Cells were then treated with DBCO-biotin (50 µM) for 1.5 h at room temperature in the dark, followed by washing three times with PBSB. Next, cells were incubated with avidin-Texas Red conjugate (200:1 dilution of a 1 mg/mL stock solution in PBS 1×) for 15 minutes at room temperature in the dark, followed by washing three times with PBSB. Finally, the cells were subjected to CuAAC with Az488 as described above, washed three times with PBS 1×, and prepared for fluorescence microscopy as described above.

Results

Figure 2:
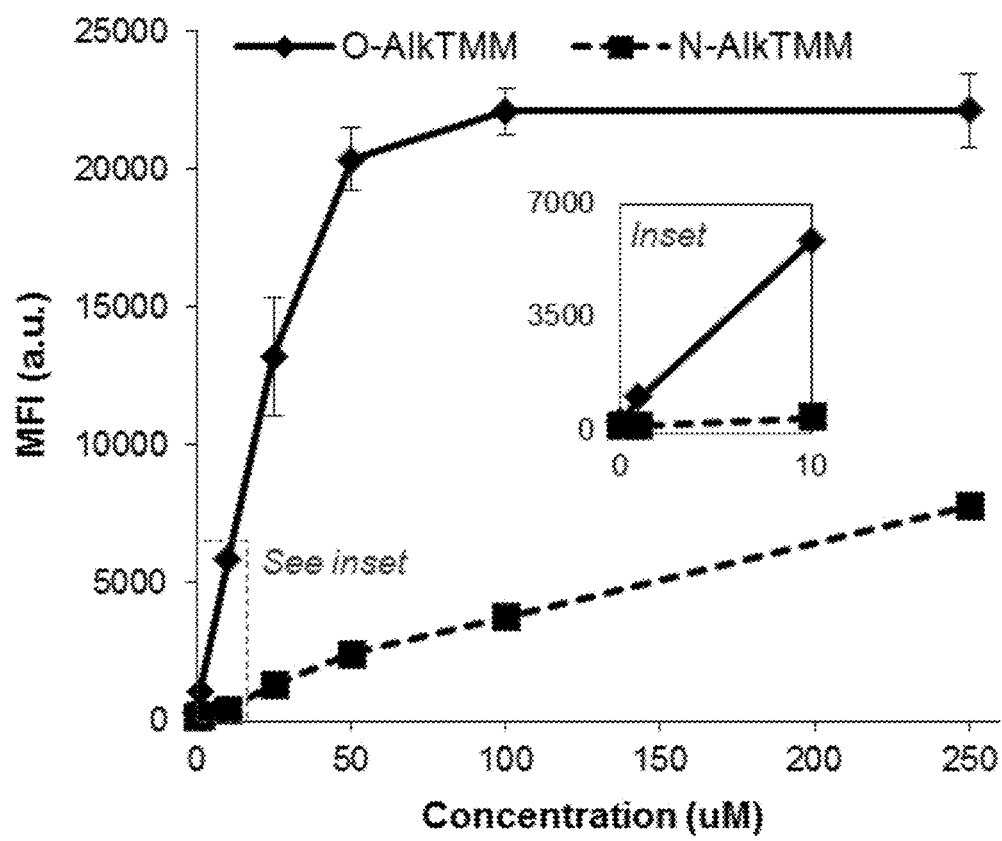
FIG. 2 shows a plot of metabolic incorporation for disclosed compounds into live Msmeg cells where Msmeg was incubated with compounds as a function of concentration.
Figure 10:
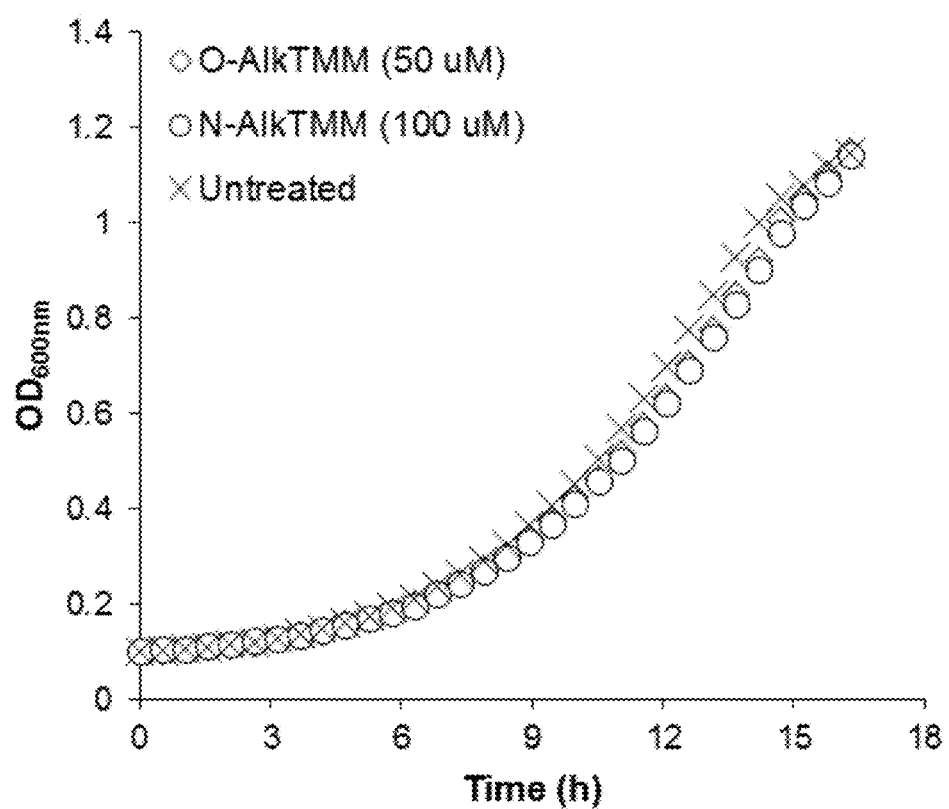
FIG. 10 shows a plot of how disclosed compounds affect the growth of Msmeg.

O- and N-AlkTMM were first evaluated for metabolic labeling in *M. smegmatis* mc2155 (Msmeg), which possesses MM biosynthetic pathways and architecture that are representative of other species in the Corynebacterineae. Wild-type Msmeg was cultured in the presence of varying concentrations (1-250 m) of O- or N-AlkTMM until late-log phase (14 h) and then reacted with an azido fluorophore (Az488) under Cu-catalyzed azide-alkyne cycloaddition (CuAAC) conditions. Flow cytometry analysis showed successful labeling for both probes, although different labeling efficiencies were observed (FIG. 2). O-AlkTMM exhibited strong labeling even at very low concentrations; a signal-to-noise ratio (S/N) of >20 was observed at concentrations as low as 1 mm. O-AlkTMM labeling was saturable at 50 mm concentration and a S/N of >250. By comparison, N-AlkTMM labeling was less efficient, giving approximately 10-fold lower signal at the same concentrations, yet the S/N still reached >150 under the conditions tested. The high S/N at relatively low doses and the absence of growth defects during treatment (FIG. 10) make both O- and N-Alk-TMM appealing as chemical reporters. Additionally, no growth impairment was observed for either compound up to 250 M.

Figure 3:
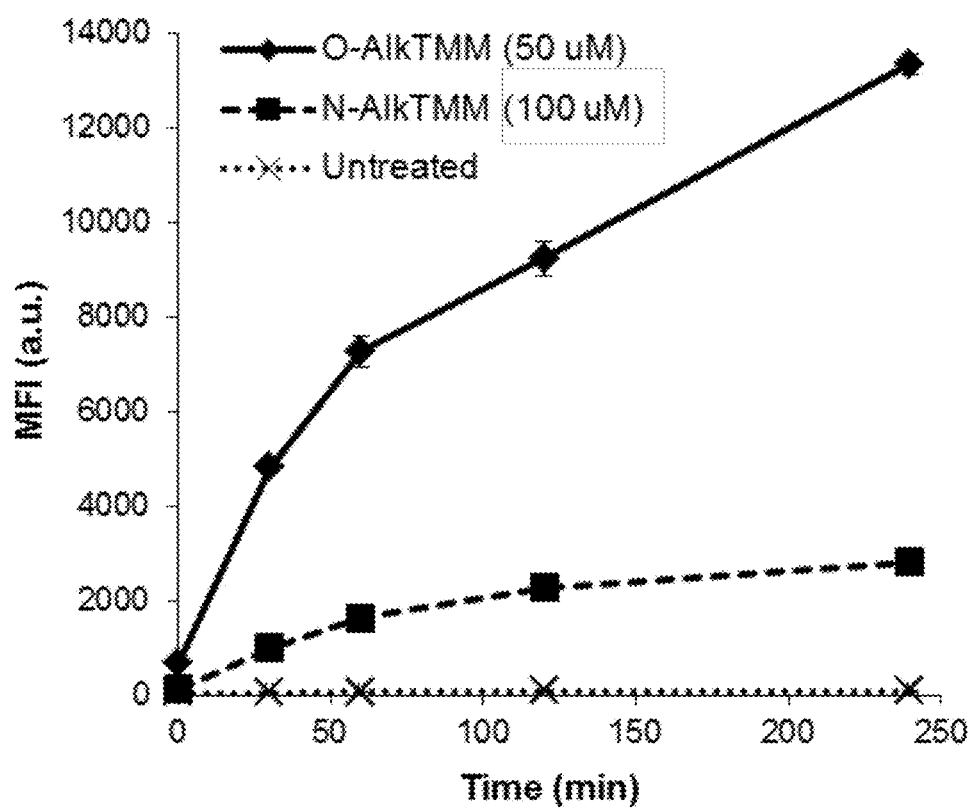
FIG. 3 shows a plot of metabolic incorporation of disclosed compounds into live Msmeg cells where Msmeg was incubated with compounds as a function of time.
Figure 4:
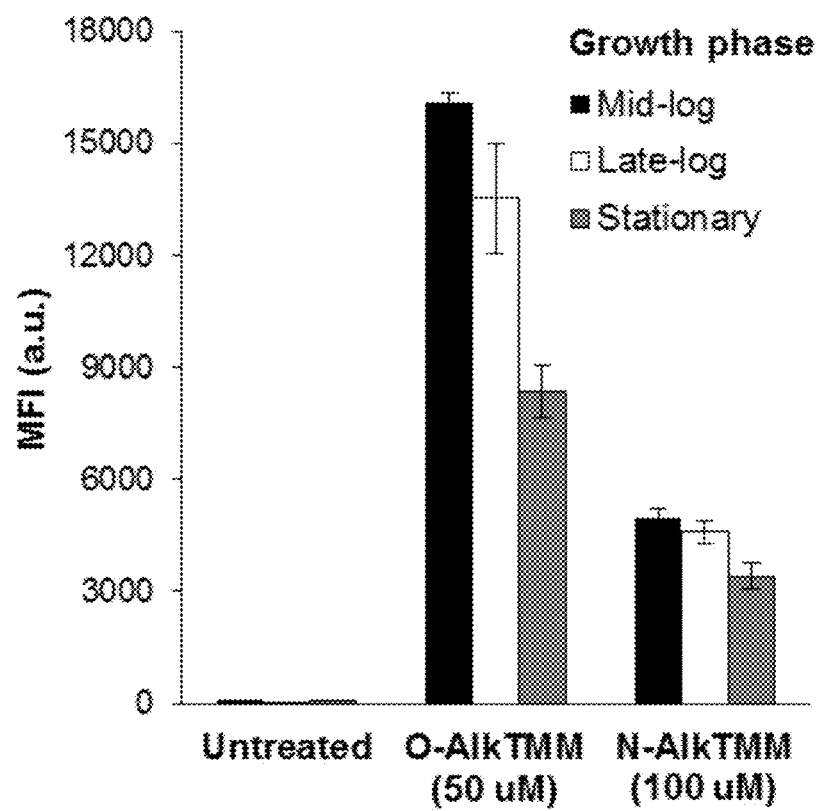
FIG. 4 shows a plot of growth phase dependence for disclosed compounds labeling in live Msmeg cells.

The observed dose-dependent labeling suggested that active metabolic incorporation of the disclosed AlkTMM probes was occurring, which was further supported by experiments evaluating the time- and growth phase-dependence of labeling, as well as competition experiments (FIG. 3-5). Both O- and N-AlkTMM exhibited time-dependent increases in labeling until signal saturation occurred between 2-4 h, which is the approximate doubling time for Msmeg. Of note, significant labeling could be detected for O- and N-AlkTMM after only a few seconds of culture time, suggesting that they may be useful for probing mycolylation processes that occur on extremely short timescales. Growth phase dependence experiments showed a significant decrease in O- and N-AlkTMM labeling between log- and stationary-phase Msmeg. Labeling was also reduced by competition with unlabeled versions of the probes (synthesized by Pd-catalyzed alkyne reduction of O- and N-Alk-TMM), further confirming metabolic incorporation of the disclosed AlkTMM probes. Additionally, the specificity data, presented herein, strongly support the hypothesized labeling routes and molecular targets for O- and N-Alk-TMM.

Figure 6:
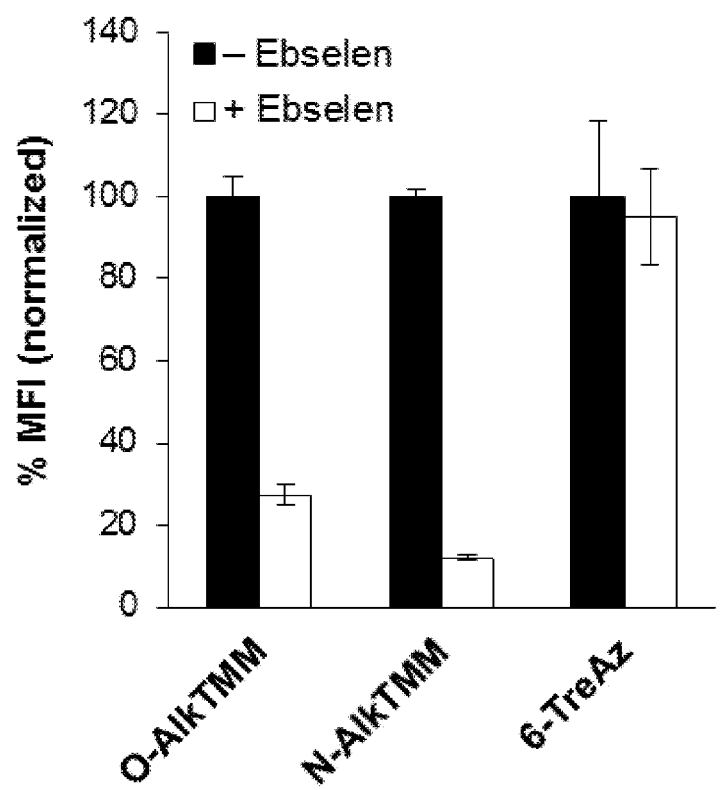
FIG. 6 shows a plot demonstrating Ag85-dependency of disclosed compounds.
Figure 11:
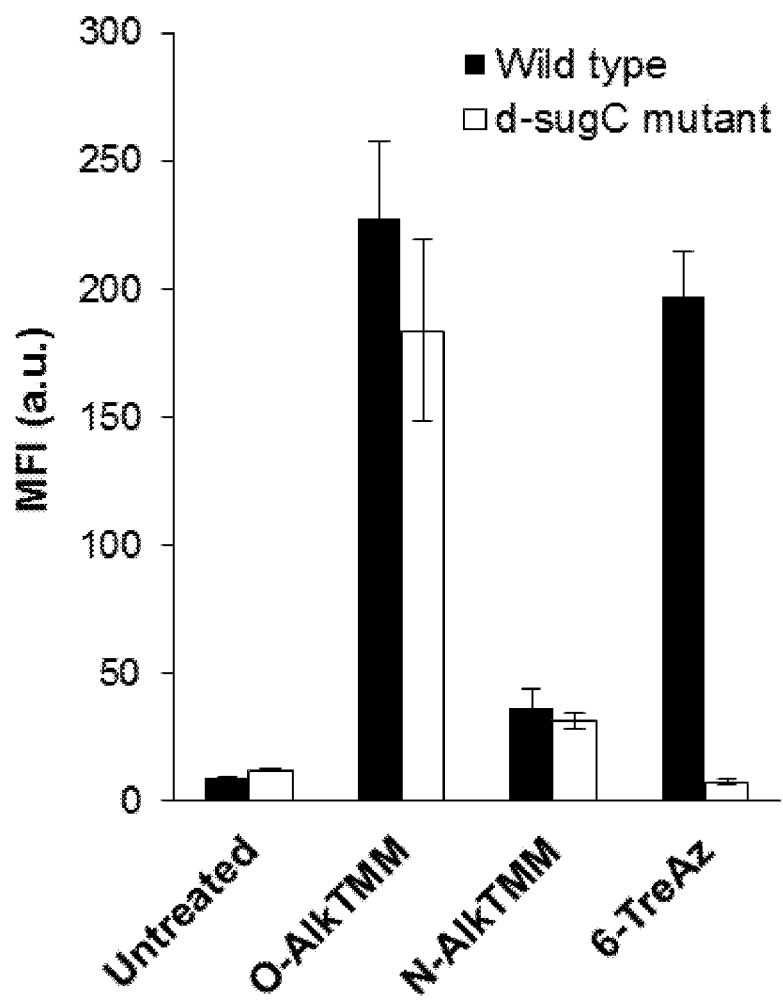
FIG. 11 shows a plot of the comparison of disclosed compounds labeling in Msmeg wild type and Msmeg ΔsugC, which is a mutant strain lacking a functional Sug-ABC-LpqY trehalose transporter.

To establish that O- and N-AlkTMM were incorporated into MM components through Ag85, labeling experiments were performed in the presence of ebselen, which was identified as a covalent inhibitor of all Ag85 isoforms in *M. tuberculosis*. Upon treatment of Msmeg with ebselen, O- and N-AlkTMM labeling decreased by approximately 70% and 85%, respectively, confirming their Ag85 specificity (FIG. 6). To rule out the possibility that the observed signal loss was due to a general reduction in cellular metabolism, it was confirmed that ebselen treatment did not reduce Msmeg labeling using 6-TreAz, which is known to be incorporated into cell wall TMM in an Ag85-independent manner; rather, it traverses an intracellular route consisting of SugABC-LpqY/Pks13/MmpL3. It was also verified that, in contrast to 6-TreAz, incorporation of O- and N-AlkTMM was not dependent on the trehalose transporter SugABC-LpqY (FIG. 11). Together, these data support the hypothesized periplasmic route of AlkTMM incorporation by Ag85 (FIG. 31).

Figure 7:
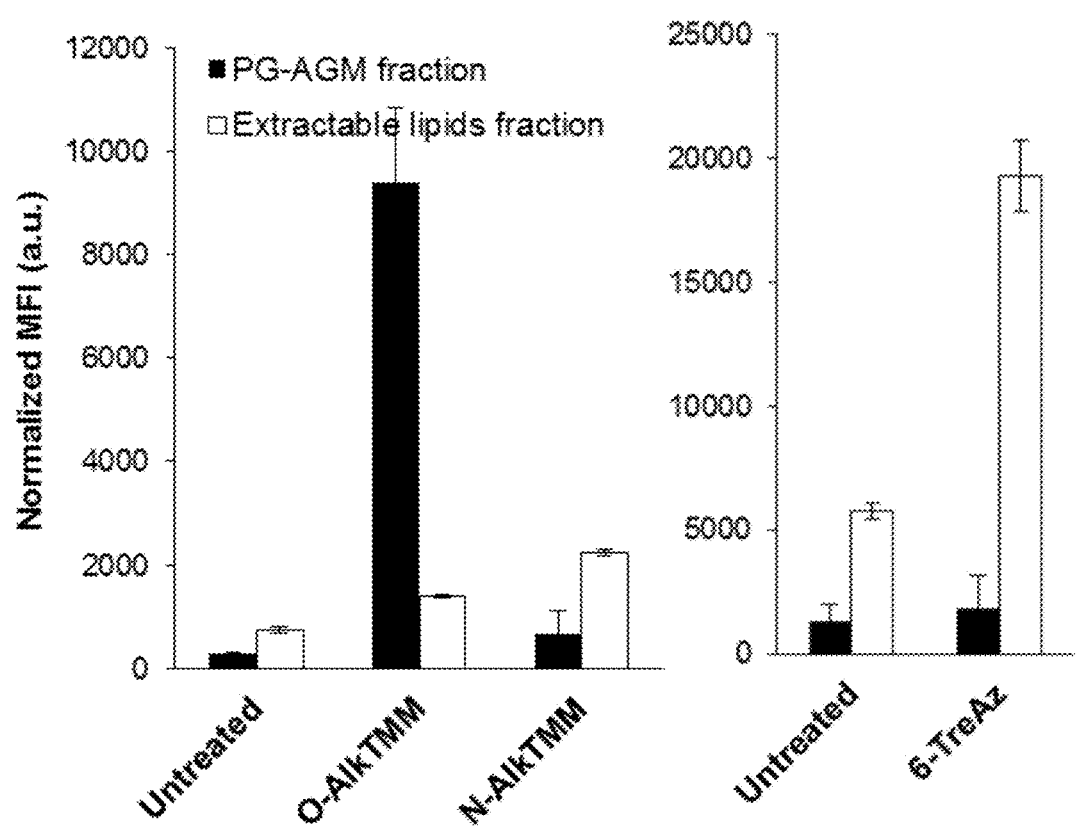
FIG. 7 shows a plot demonstrating that disclosed compounds can selectively label covalent AGM and extractable trehalose glycolipid fractions. Msmeg was treated with the indicated compound (or left untreated).

It was hypothesized that O- and N-AlkTMM would have distinct targets in the MM, with O-AlkTMM selectively reporting on AGM and N-AlkTMM reporting on trehalose glycolipids. Specifically, it was hypothesized that O-Alk-TMM would be able to access the cellular periplasm and serve as a substrate for Ag85, leading to transfer of the 6-heptynoyl group to terminal AG residues, and that N-Alk-TMM would be able to serve as a mycolylation acceptor and predominantly form a labeled version of TDM. To differentiate between these possibilities, Msmeg was treated with O- or N-AlkTMM, conjugated Az488 by CuAAC, and then Msmeg cells were fractionated into i) insoluble cell wall material, including the PG-AGM complex, and ii) soluble extractable lipids, including the trehalose glycolipids. TLC analysis confirmed separation of trehalose glycolipids from the PGAGM material (FIG. 12). Analysis of solubilized samples revealed that nearly all of the fluorescence from O-AlkTMM treated Msmeg was present in the PG-AGM fraction, while N-AlkTMM-treated Msmeg showed signal only in the extractable lipids fraction, supporting the hypothesized probe selectivity (FIG. 7). As a control, the same experiment was performed with 6-TreAz, which is known to label trehalose glycolipids with high efficiency but not AGM. The 6-TreAz-treated sample showed signal exclusively in the extractable lipids fraction, matching the results from N-AlkTMM. The nominal fluorescence observed in the extractable lipids fraction of the O-AlkTMM-treated sample likely corresponds to a small fraction of this probe reacting with TMM to form alkyne-labeled TDM (estimated at <10% based on FIG. 7).

Figure 8:
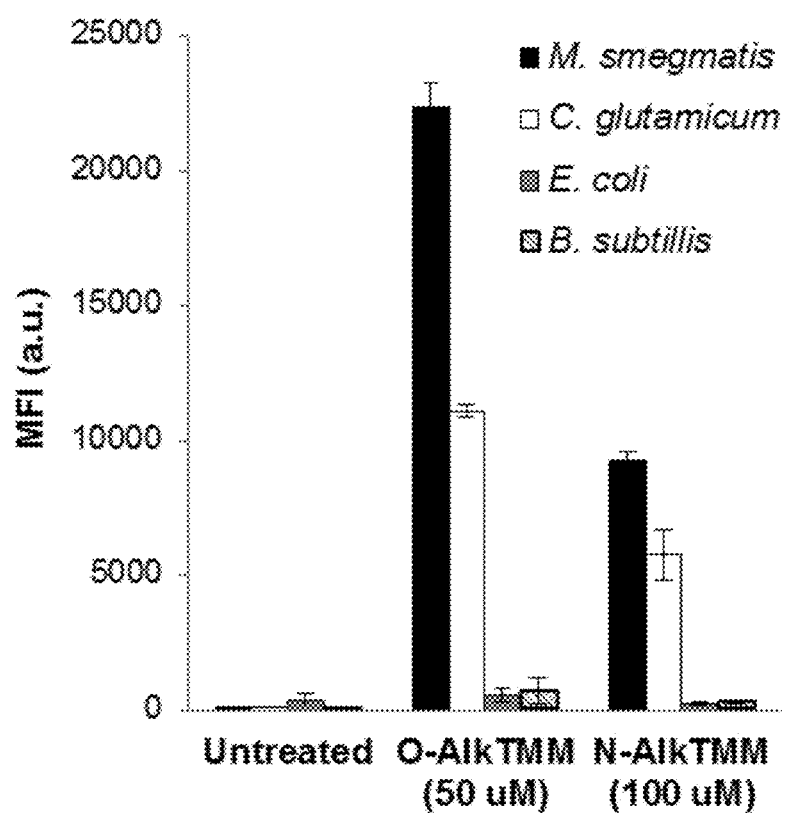
FIG. 8 shows a plot demonstrating specificity of disclosed compounds for MM-containing species of the Corynebacterineae suborder.

Next, the specificity of O- and N-AlkTMM was assessed for species in the Corynebacterineae suborder. While these species possess the conserved MM biosynthetic machinery (FIG. 1), canonical Gram-negative and -positive bacteria do not. Thus, O- and N-AlkTMM labeling in Msmeg and *C. glutamicum* was evaluated, both of which are members of the Corynebacterineae, as well as in *Escherichia coli* and *Bacillus subtilis*, which are representative Gram-negative and -positive species, respectively. Both Msmeg and *C. glutamicum* showed strong labeling of the cell surface by O- and N-AlkTMM, while *E. coli* and *B. subtilis* showed no labeling above background (FIGS. 8 and 9).

Figure 9:
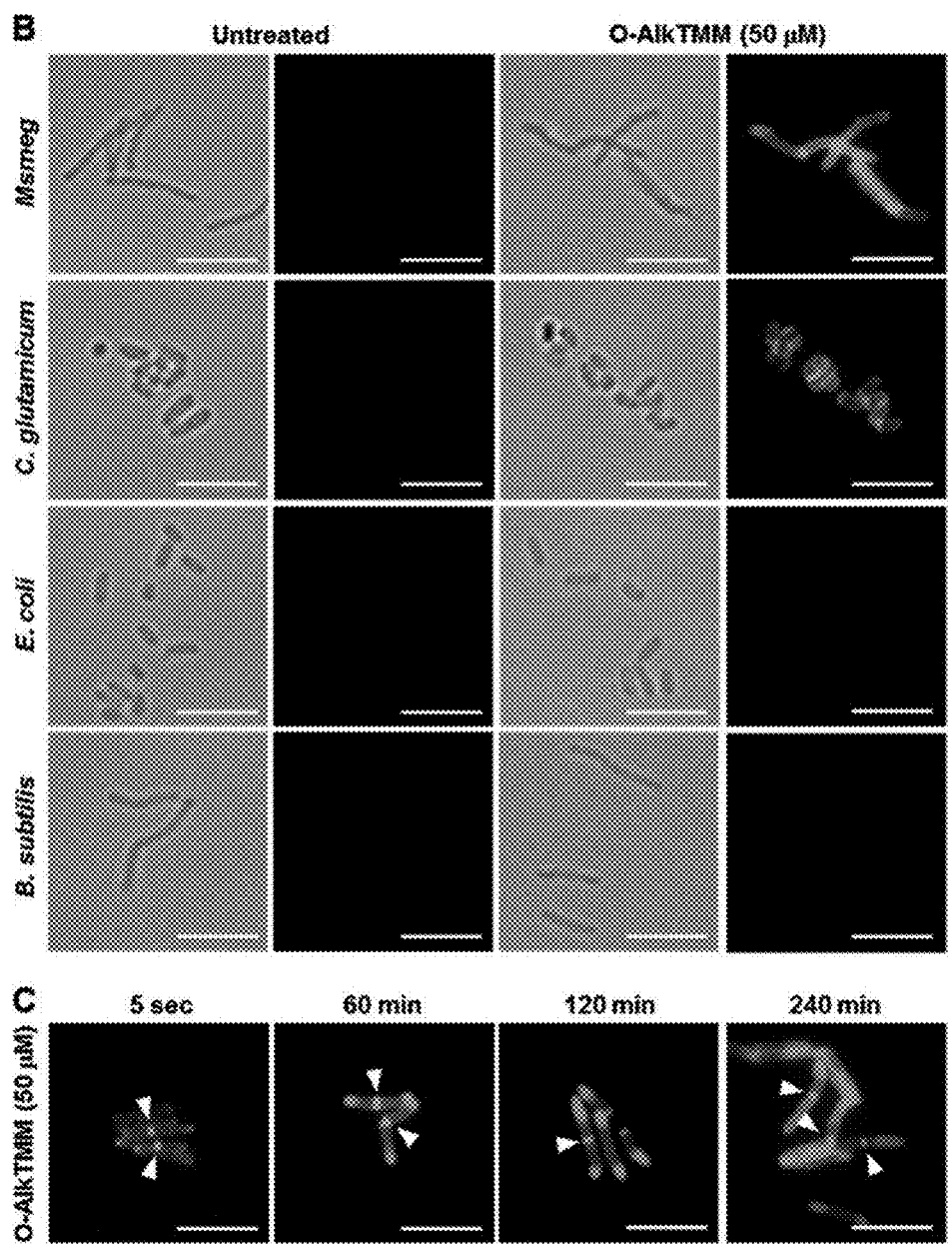
FIG. 9, upper panel shows fluorescence images (and phase contrast images) demonstrating specificity of disclosed compounds for MM-containing species of the Corynebacterineae suborder. The lower panel shows time-course fluorescence microscopy of a disclosed compound labeling in Msmeg.
Figure 14:
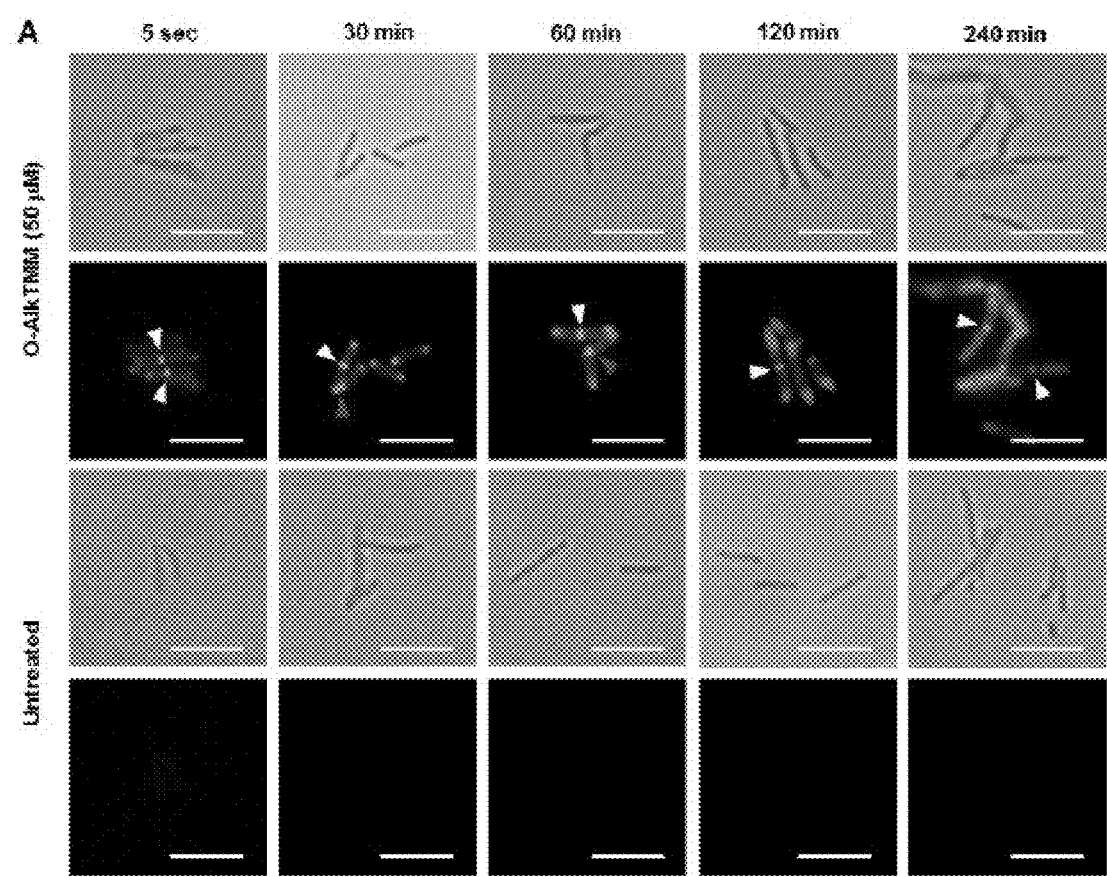
FIG. 14 shows time-course fluorescence microscopy analysis of a disclosed compound-labeling of Msmeg. White triangles mark the septa of dividing cells. Red triangles mark the maturing septa of dividing cells undergoing V-snapping. Scale bars, 5 μm.
Figure 15:
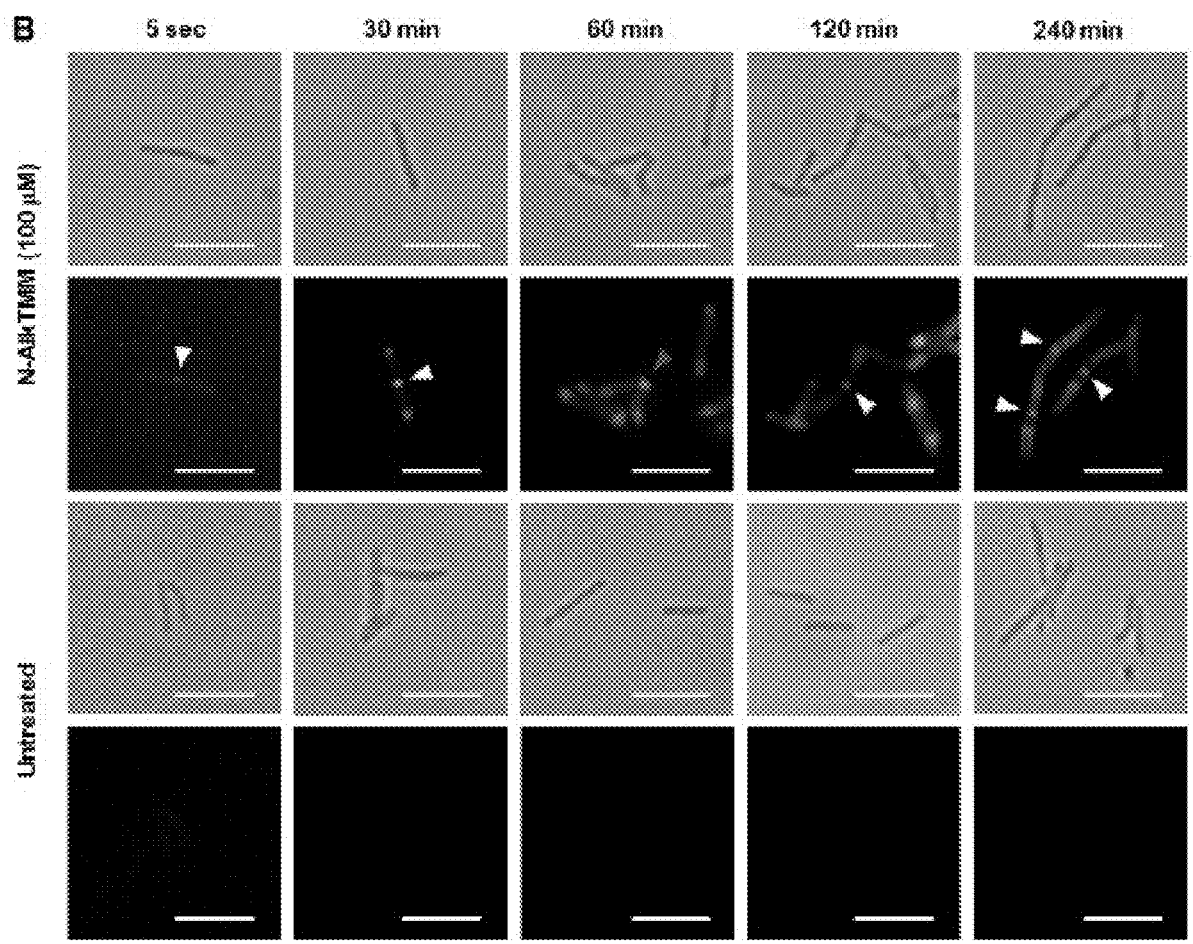
FIG. 15 shows time-course fluorescence microscopy analysis of a disclosed compound-labeling of Msmeg. White triangles mark the septa of dividing cells. Red triangles mark the maturing septa of dividing cells undergoing V-snapping. Scale bars, 5 m.
Figure 16:
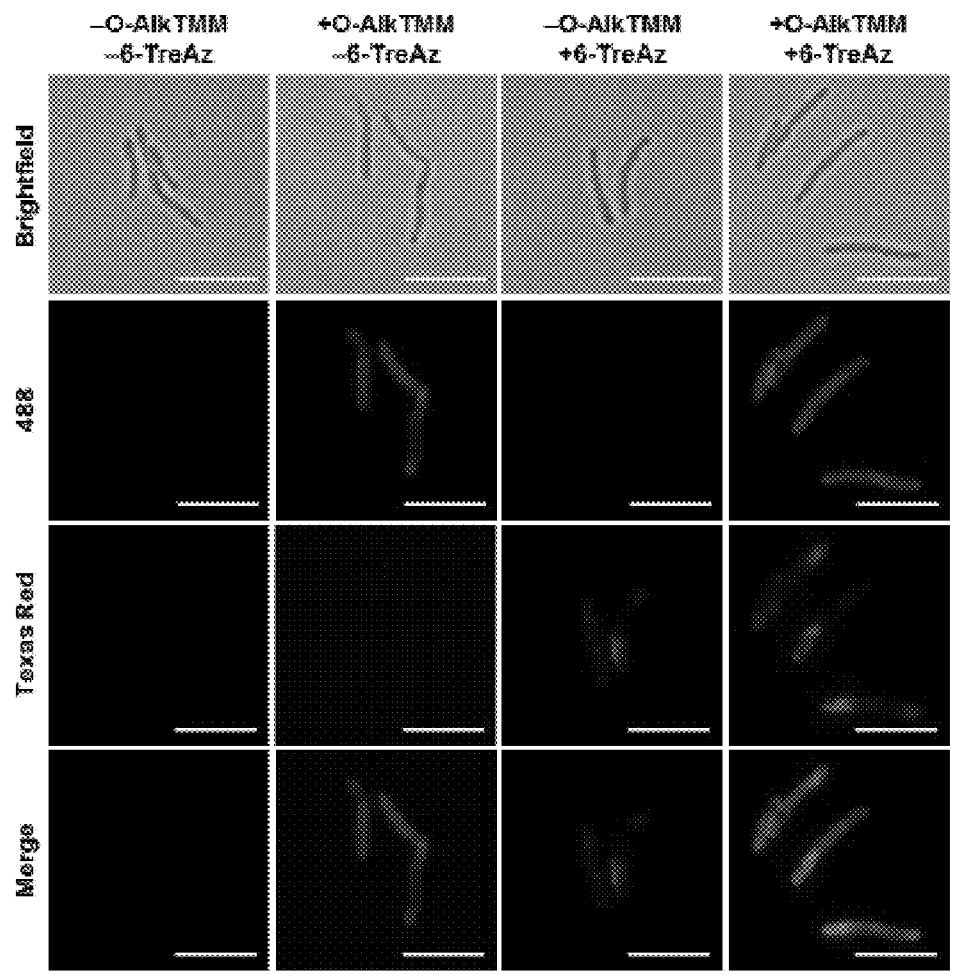
FIG. 16 shows two-color fluorescence microscopy analysis of Msmeg using a disclosed compound and 6-TreAz (6-azide-modified trehalose). Scale bars, 5 m.
Figure 17:
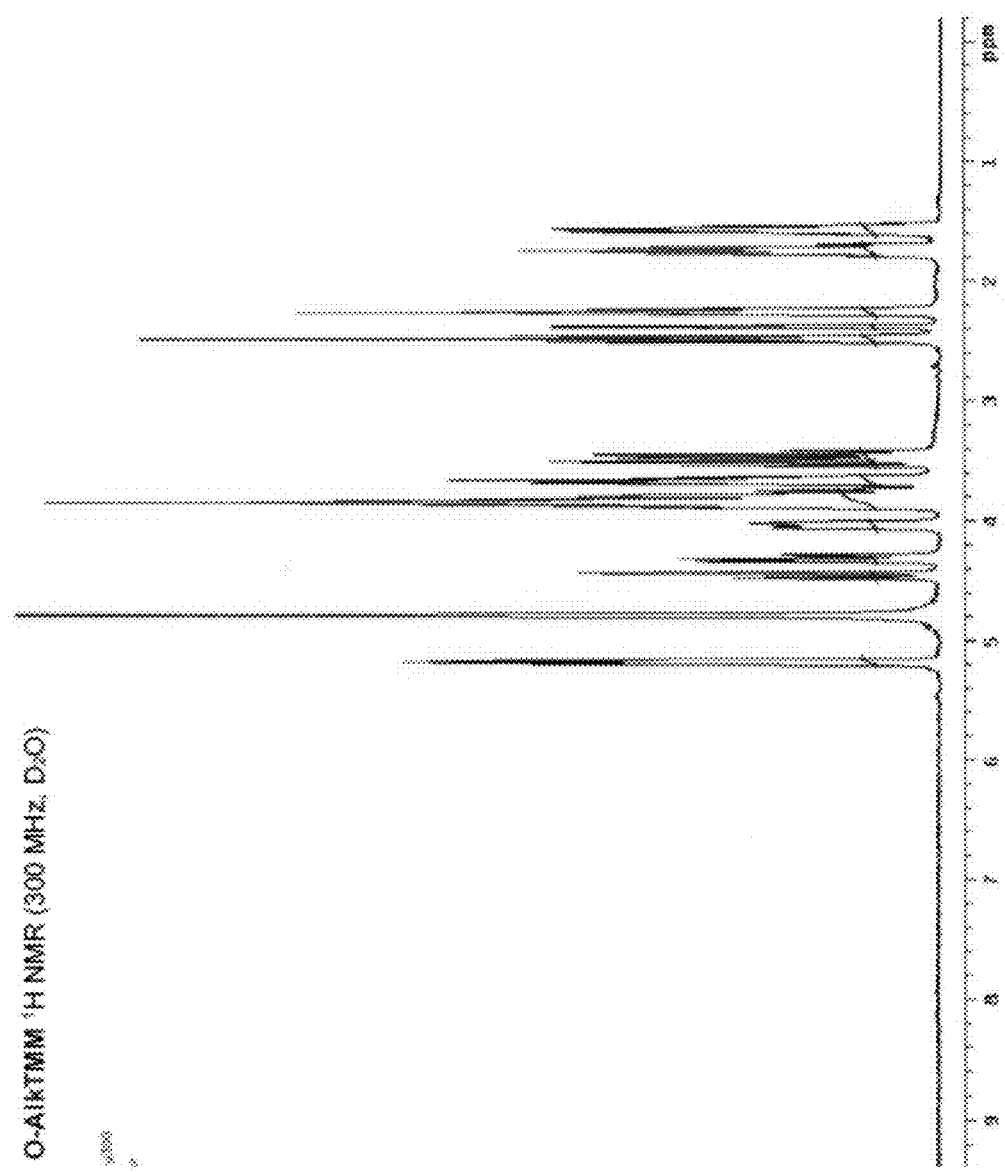
FIG. 17 shows a $^1H$ Nuclear Magnetic Resonance (NMR) spectrum of 6-O-(6-heptynoyl)-α,α-D-trehalose (O-AlkTMM, which is also referred to as O-AlkTMM-C7 herein).
Figure 18:
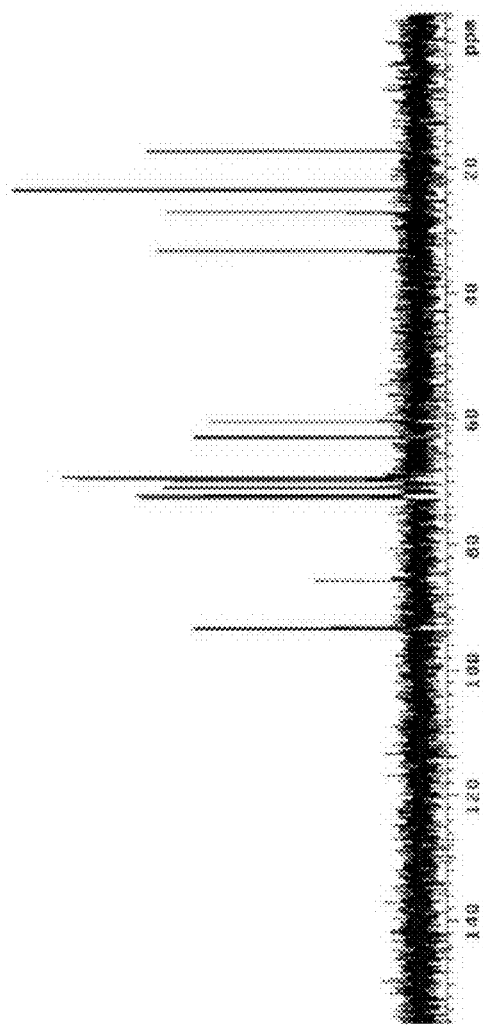
FIG. 18 shows a $^{13}C$ NMR spectrum of O-AlkTMM.
Figure 19:
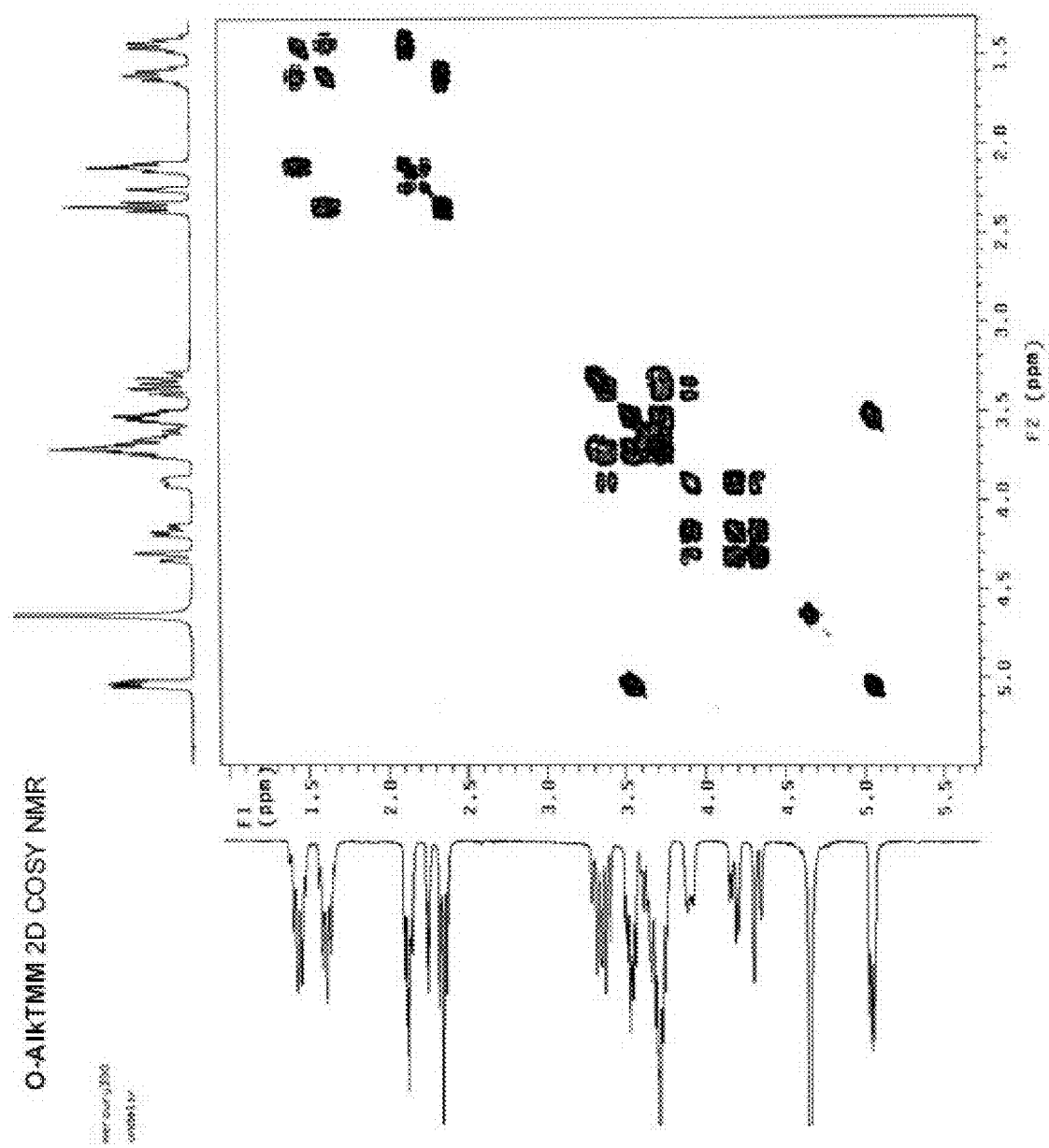
FIG. 19 shows a 2D COSY NMR spectrum of O-AlkTMM.
Figure 20:
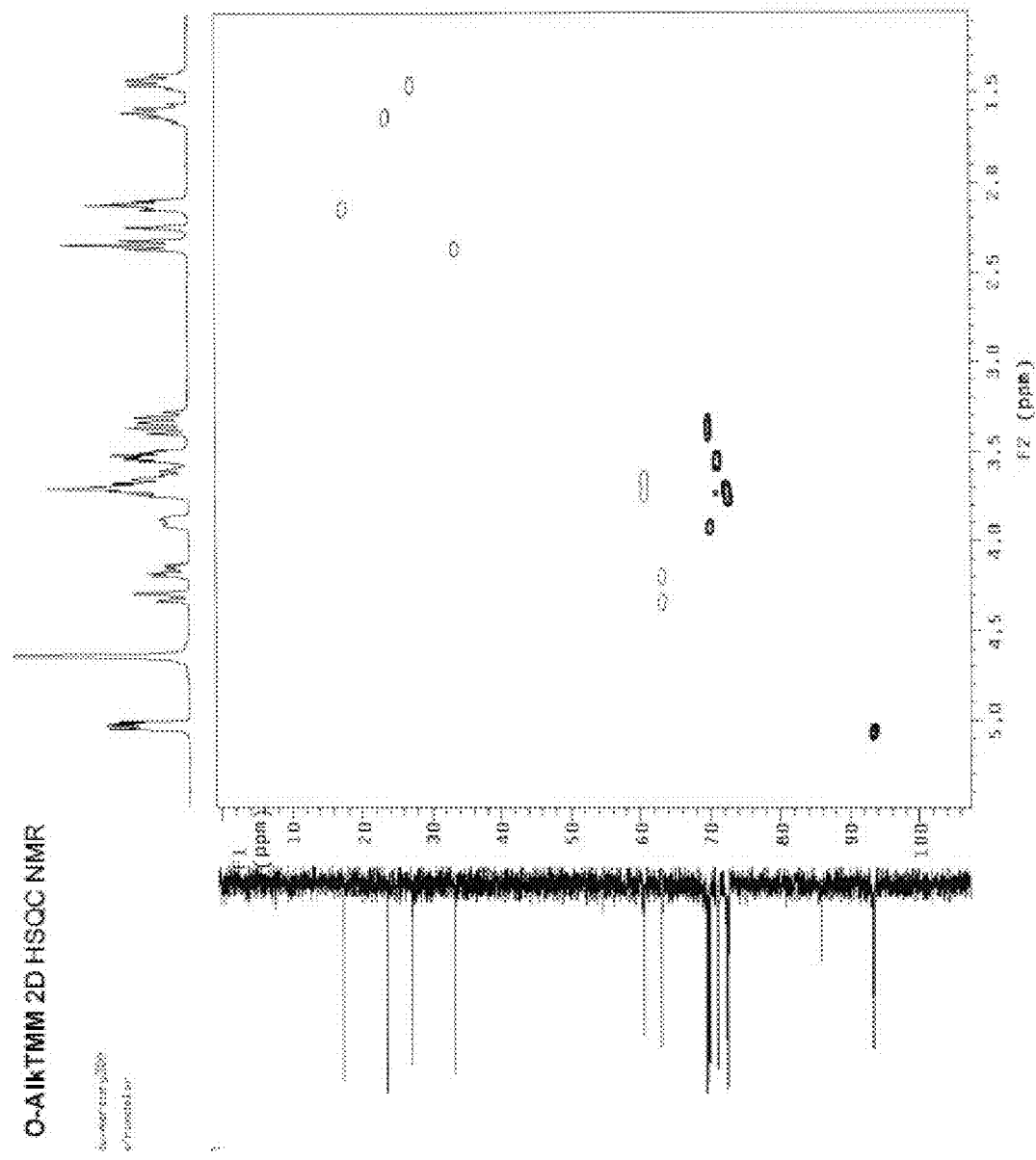
FIG. 20 shows a 2D HSQC NMR spectrum of O-AlkTMM.
Figure 21:
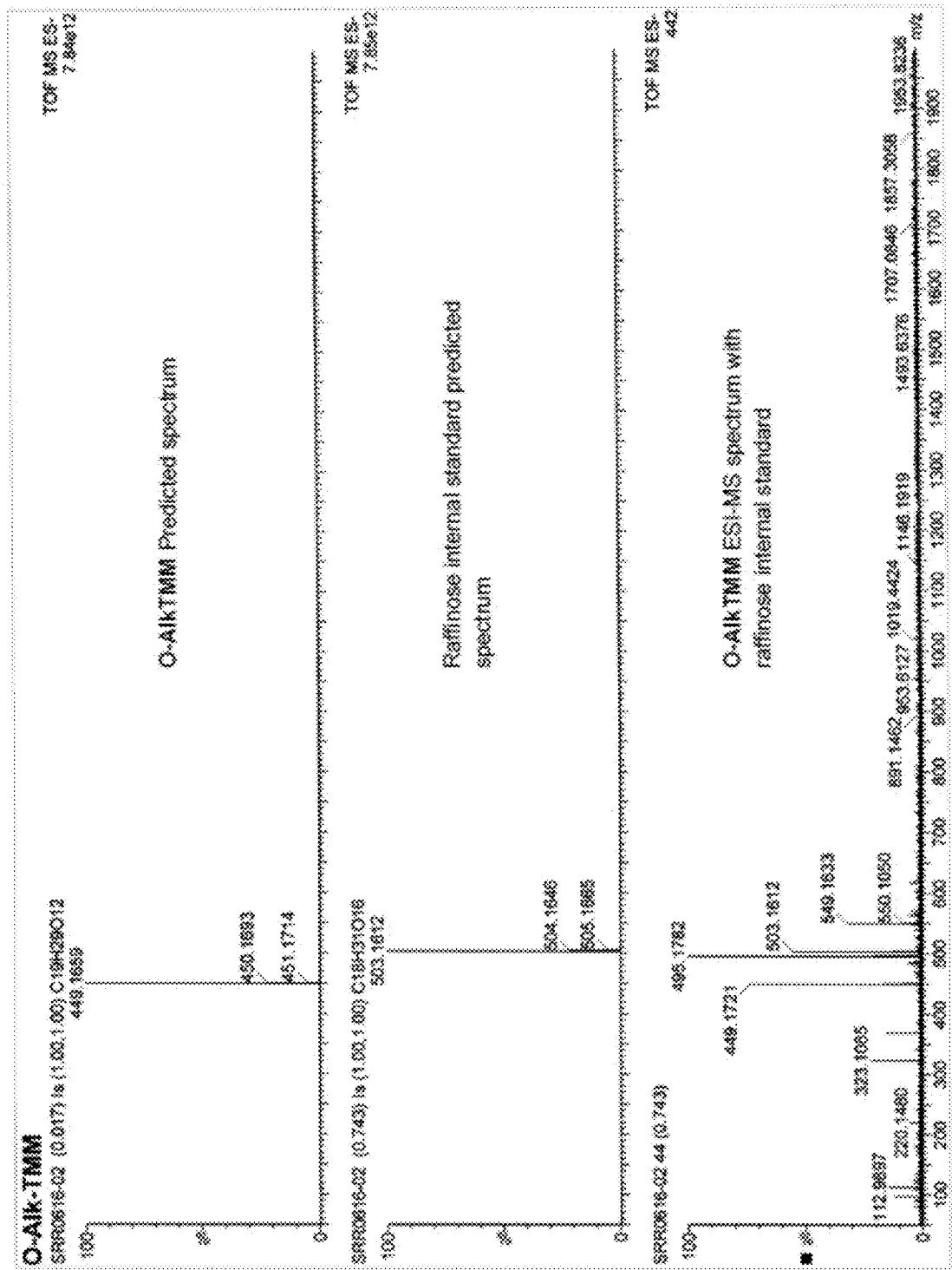
FIG. 21 shows a Time of Flight (TOF) mass spectrum of O-AlkTMM.
Figure 22:
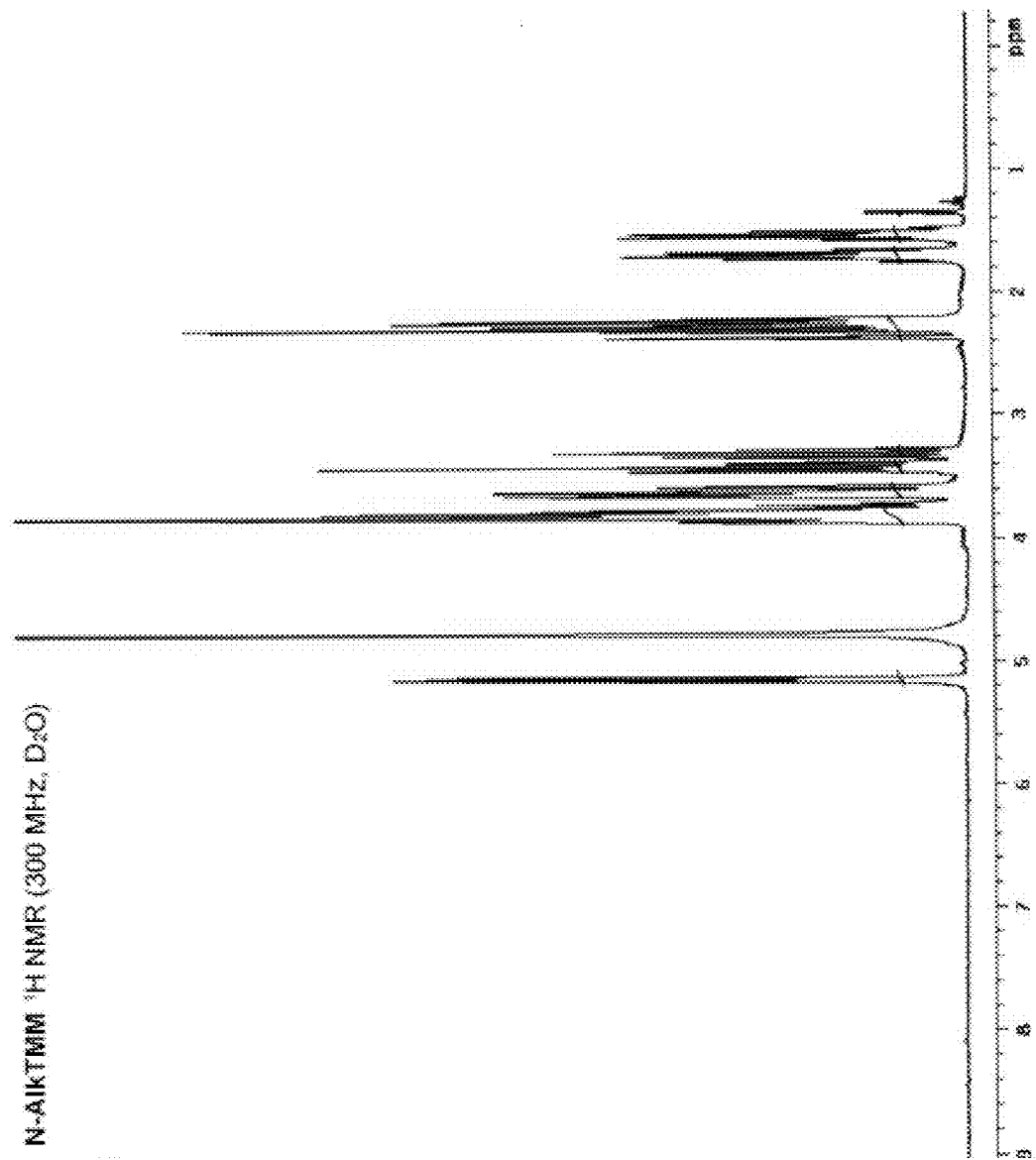
FIG. 22 shows a $^1H$ NMR spectrum of N-(6-heptynoyl)-6-amino-6-deoxy-α,α-D-trehalose (N-AlkTMM).
Figure 23:
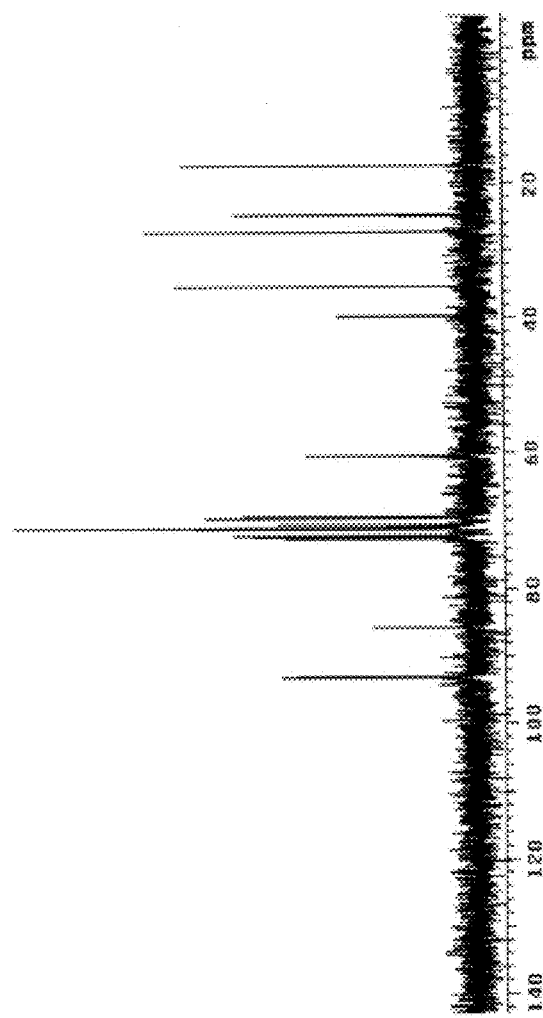
FIG. 23 shows a $^{13}C$ NMR spectrum of N-AlkTMM.
Figure 24:
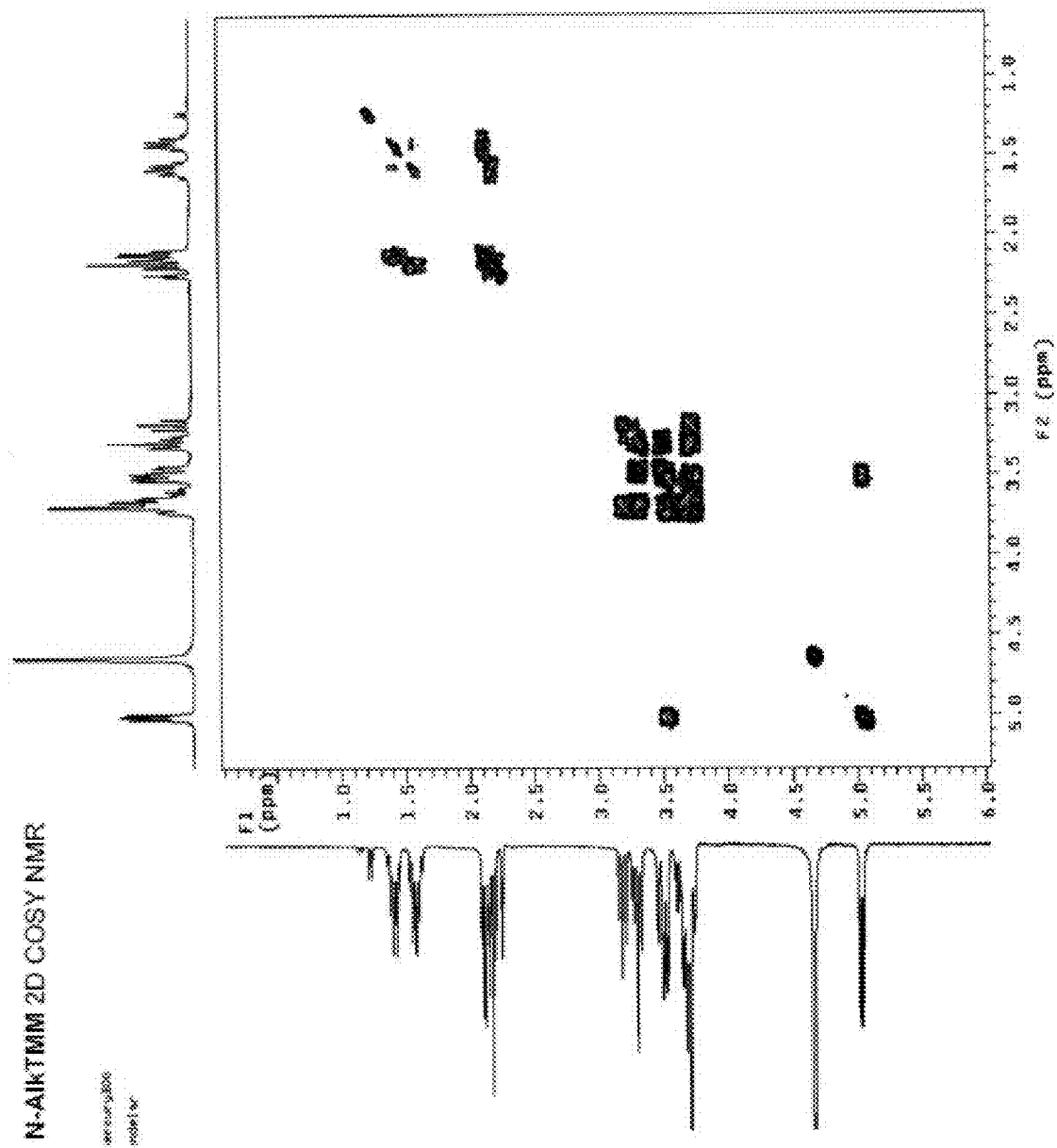
FIG. 24 shows a 2D COSY NMR spectrum of N-AlkTMM.
Figure 25:
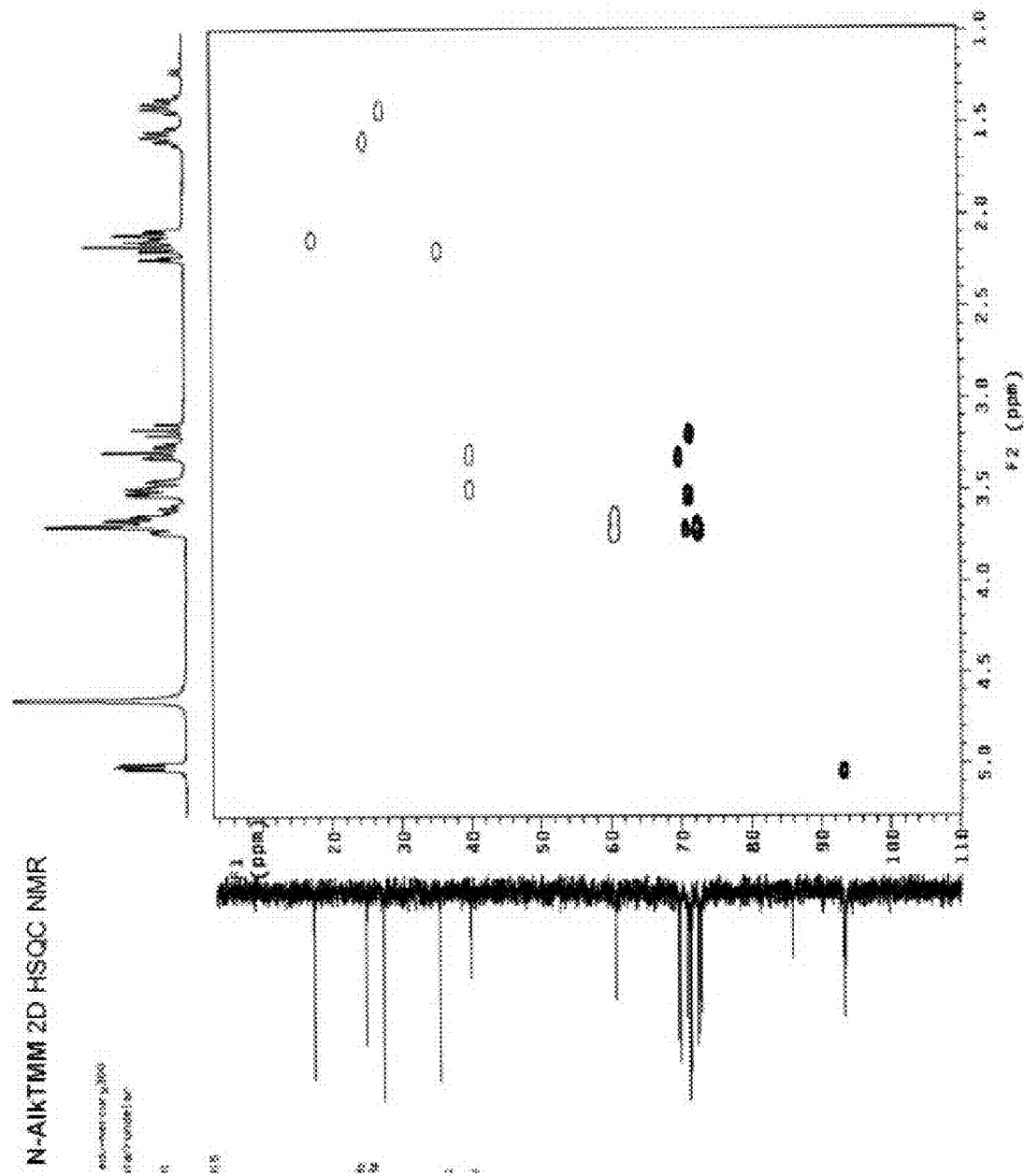
FIG. 25 shows a 2D HSQC NMR spectrum of N-AlkTMM.
Figure 26:
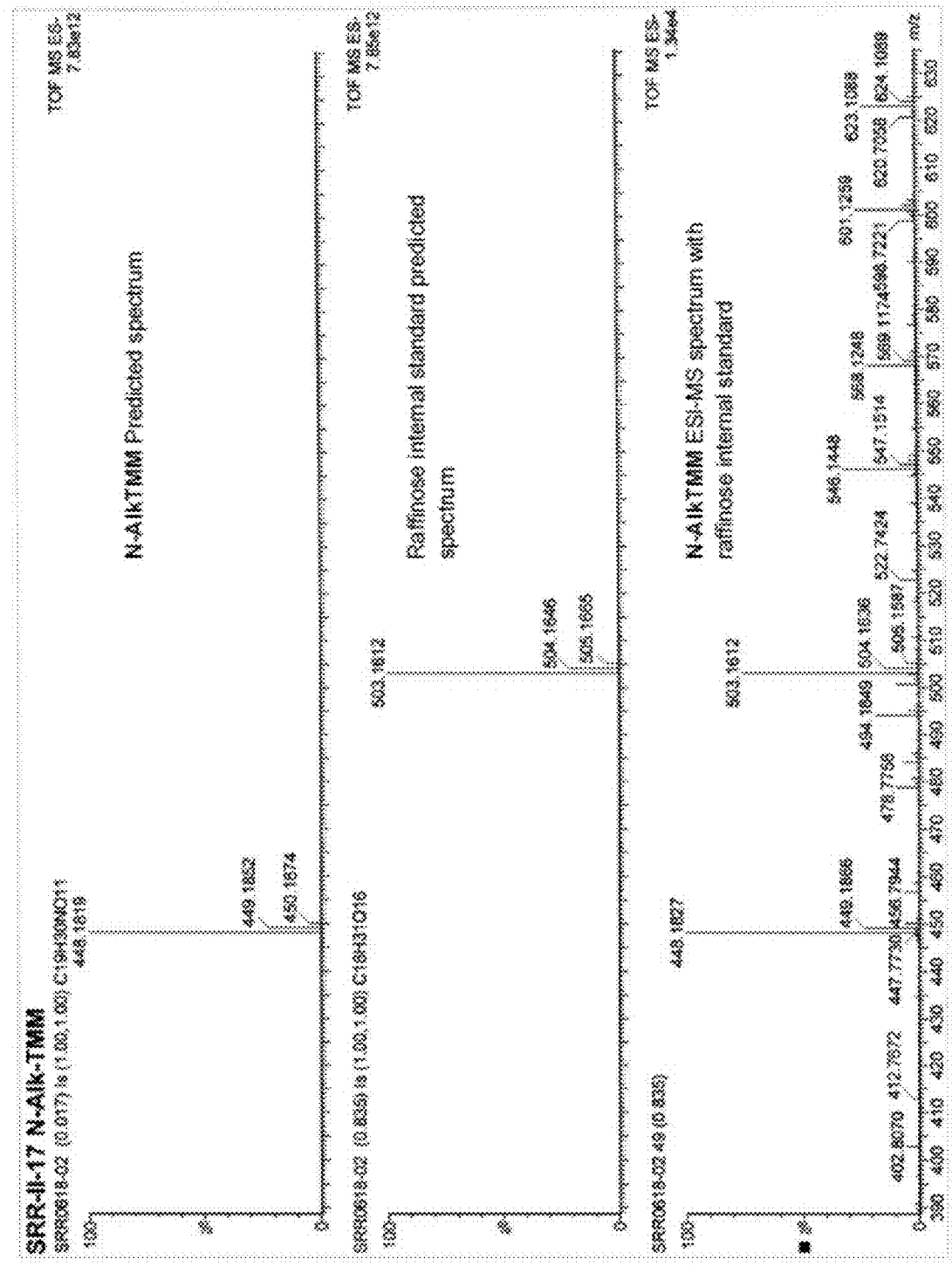
FIG. 26 shows a TOF mass spectrum of N-AlkTMM.

To demonstrate how the disclosed compounds can provide insight into MM dynamics, O- and N-AlkTMM were used to image AGM and TDM biosynthesis in Msmeg using time-course fluorescence microscopy (FIG. 9 (lower panel) and 14-15). O- and N-AlkTMM exhibited similar labeling features, characterized by intensely fluorescent septa in dividing cells, highly polar labeling for short pulses, and diffuse surface labeling for longer pulses. It was also shown that AGM and trehalose glycolipids can be simultaneously imaged by co-administering O-AlkTMM and 6-TreAz, which bear orthogonal reactive tags, followed by delivery of green and red fluorophores using appropriate bioorthogonal reactions (FIG. 16). Cells only showed strong signal in both the 488 and Texas Red channels when co-treated with O-AlkTMM and 6-TreAz, indicating that both components can be detected simultaneously. The 488 channel (detecting O-AlkTMM labeling) showed fluorescence fairly evenly distributed around the lateral wall, which is consistent with the 4 h time point from the time-course fluorescence microscopy experiment (FIG. 14-15). Likewise, signal in the Texas Red channel (detecting 6-TreAz) showed fluorescence distributed around the cell surface, with some areas of higher intensity. These experiments represent the first direct visualization of the AGM layer in mycobacteria, and they underscore how the disclosed compounds may advance understanding of mycobacterial growth and division processes, which remain poorly characterized in comparison to other types of bacteria.

In summary, the disclosed compounds can enable sensitive, selective, and simultaneous detection of AGM and trehalose glycolipids in situ, providing a platform to study the MM in its native setting. The chemical reporters described herein are mycobacteria-specific, connoting potential for detection of bacteria in complex settings, for example, in sputum samples or during infection. Additionally, the ability of Ag85 to catalyze the transfer of non-native lipids from the disclosed compounds to AG represents a strategy for cell surface modification of live mycobacteria. Coupled with the ease of synthesizing the disclosed compounds, this strategy can facilitate chemical remodeling of the MM for various applications.

Example 3

Metabolic Labeling & Analysis of Bacteria—2

Methods
Bacterial Strains, Media, and Reagents.
The bacterial strains used in this work included Msmeg mc$^2$155 wild type, *Corynebacterium glutamicum* 534, *Escherichia coli* K12 MG1655, and *Bacillus subtilis* 168. Msmeg was cultured in Middlebrook 7H9 liquid medium supplemented with ADC (albumin, dextrose, and catalase), 0.5% glycerol, and 0.05% Tween-80. *C. glutamicum, E. coli*, and *B. subtilis* were cultured in LB liquid medium. All bacteria were cultured at 37° C., except *C. glutamicum*, which was cultured at 30° C.

Compound numbering in this Example refers to Scheme 3. Stock solutions of O-AlkTMM O-AzTMM analogues (1-4) were prepared in phosphate-buffered saline (PBS) at concentrations of 25 mM, sterile-filtered (0.2 m), and stored at −20° C. Prior to usage in labeling experiments, stock solutions of compounds 1-4 were diluted to the desired concentration with PBS and appropriate culture medium, and temporarily stored at 4° C. O-TCO-TMM (5), O-FITC-TMM (6), and 2-FlTre probe stocks were prepared in dimethylsulfoxide (DMSO) at 25 mM and stored at −20° C. Prior to usage in labeling experiments, stock solutions of compounds 5-6 were diluted to the desired concentrations with DMSO and appropriate culture medium and temporarily stored at 4° C. Other reagent stocks included: azide-modified carboxyrhodamine 110 (Az488, Click Chemistry Tools, 1 mM in DMSO, stored at −20° C.); alkyne-modified carboxyrhodamine 110 (Alk488, Click Chemistry Tools, 1 mM in DMSO, stored at −20° C.); DBCO-488 (Click Chemistry Tools, 1 mM in DMSO, stored at −20° C.); methyltetrazine-Cy3 or tetrazine-Cy3 (Click Chemistry Tools, 1 mM in DMSO, stored at −20° C.); sodium ascorbate (60 mM in H$_2$O, always freshly prepared); tris[(1-benzyl-1H-1,2,3-triazol-4-yl)methyl]amine (TBTA) ligand for CuAAC reactions (Click Chemistry Tools, 6.4 mM in tert-BuOH/DMSO 4:1, stored at −20° C.); CuSO$_4$ (50 mM in H$_2$O, stored at −20° C.).

General Procedures for Bacterial Labeling.
Starter cultures of bacteria were generated by inoculating a single colony from a freshly streaked LB agar plate into 3 mL liquid medium in a culture tube. Starter cultures were incubated at 37° C. (or 30° C. for *C. glutamicum*) with shaking until reaching mid-logarithmic phase and then diluted with liquid medium to the desired density for initiating experiments.

Labeling experiments were performed either in 96-well plate format or in aerated culture tubes. For experiments in 96-well plate format, bacteria were mixed with liquid medium and probe stock solution in sterile flat-bottom 96-well plates to achieve the desired cell density and probe concentration at a final volume of 200 μL. Plates were incubated at 37° C. (or 30° C. for *C. glutamicum*) with shaking in a Tecan plate reader (Infinite F200 PRO operated by Tecan iControl software) until the desired end-point (typical culture time 4 h).

For secondary labeling of bacteria with a fluorophore, suspensions of alkyne-, or azide-, or TCO-labeled cells (200 μL) were transferred to a v-bottom 96 well plate, centrifuged (3,600 rpm, 10 min, room temperature) and washed with PBS 1× containing 0.5% bovine serum albumin (PBSB) three times. Depending on which reaction the reporter required (CuAAC, SPAAC or tetrazine ligation), the cells were treated appropriately. For CuAAC, cells were first fixed with 4% paraformaldehyde in PBS for 10 min and washed three times with PBSB. Then, the CuAAC reaction was carried out by resuspension of cells in PBSB (138 μL) and sequential addition of stock solutions of 1 mM Az488 (or Alk488) (3 μL), 60 mM sodium ascorbate (3 μL), 6.4 mM TBTA (3 μL), and 50 mM $CuSO_4$ (3 μL) to give a final reaction volume of 150 μL and the following final reagent concentrations: Az488 (or Alk488), 20 μM; sodium ascorbate, 1.2 mM; TBTA, 128 PM; $CuSO_4$, 1 mM. After thorough mixing, reactions were incubated in the dark at room temperature for 30 min. Finally, cells were washed with PBSB three times and prepared for analysis by flow cytometry or fluorescence microscopy as described below. For SPAAC, cells were resuspended in PBSB (171 μL), then typically 9 μL of a stock solution of 1 mM DBCO-488 was added to give a final reaction volume of 180 μL and a final DBCO-488 concentration of 50 M. After thorough mixing, reactions were incubated in the dark at room temperature for 30 min. Finally, cells were washed with PBSB, fixed, and prepared for analysis by flow cytometry or fluorescence microscopy as described below. For the tetrazine ligation, cells were resuspended in PBSB (171 μL), then typically 9 μL of a stock solution of 1 mM tetrazine-Cy3 or methyltetrazine-Cy3 was added to give a final reaction volume of 180 μL and a final reagent concentration of 50 μM. After thorough mixing, reactions were incubated in the dark at room temperature for 30 min. Finally, cells were washed with PBSB, fixed, and prepared for analysis by flow cytometry or fluorescence microscopy as described below. For O-FITC-TMM labeling experiments, no secondary labeling was required. In this case, O-FITC-TMM-labeled cells were fixed with 4% paraformaldehyde in PBS for 10 min, washed three times with PBSB, and prepared for flow cytometry or fluorescence microscopy. For the SPAAC vs. tetrazine ligation cell-surface reaction kinetics comparison, experiments were carried out as described above with minor modifications. DBCO-488 and tetrazine-Cy3 were used at final concentrations of 20 μM each. To vary the cell-surface reaction times, cells were incubated with secondary labeling reagent for the indicated period of time, then immediately centrifuged and washed to remove unbound reagent.

Flow Cytometry.

After fluorescent labeling of bacteria according to the above general procedure, bacteria were transferred to 5 mL polystyrene Falcon tubes (BD Biosciences) and analyzed by flow cytometry. Flow cytometry was performed on a BD Biosciences FACSAria II flow cytometer. Fluorescence data was collected for 50,000 cells at an event rate of 500-1,000 events/sec and processed using BD FACSDIVA 8.0.1. All flow cytometry experiments were performed with three replicate samples, and data shown were representative of at least two independent experiments. Scatter-gated fluorescence analysis was used to obtain mean fluorescence intensities with doublet discrimination.

Fluorescence Microscopy.

10 μL of bacterial sample in PBS were spotted onto a microscope slide, lightly spread into a thin layer using the edge of a coverslip, and allowed to air dry in the dark. Fluoromount-G mounting medium (SouthernBiotech) was applied, then cover slips were placed over the sample and immobilized with adhesive. Microscopy was carried out using an EVOS FL (Life Technologies) inverted microscope equipped with a 100×1.4 numerical aperture Plan-Apochromat oil immersion lens. Fluorescence imaging was performed using GFP (maximum excitation/emission=470/510 nm) and RFP (maximum excitation/emission=531/593 nm) LED light cubes. Images were captured with a Sony ICX445 CCD camera and processed using the FIJI distribution of ImageJ. Image acquisition and processing were performed identically for all test and control samples being compared. Imaging data shown were representative of at least two independent experiments.

Results

Figure 61:
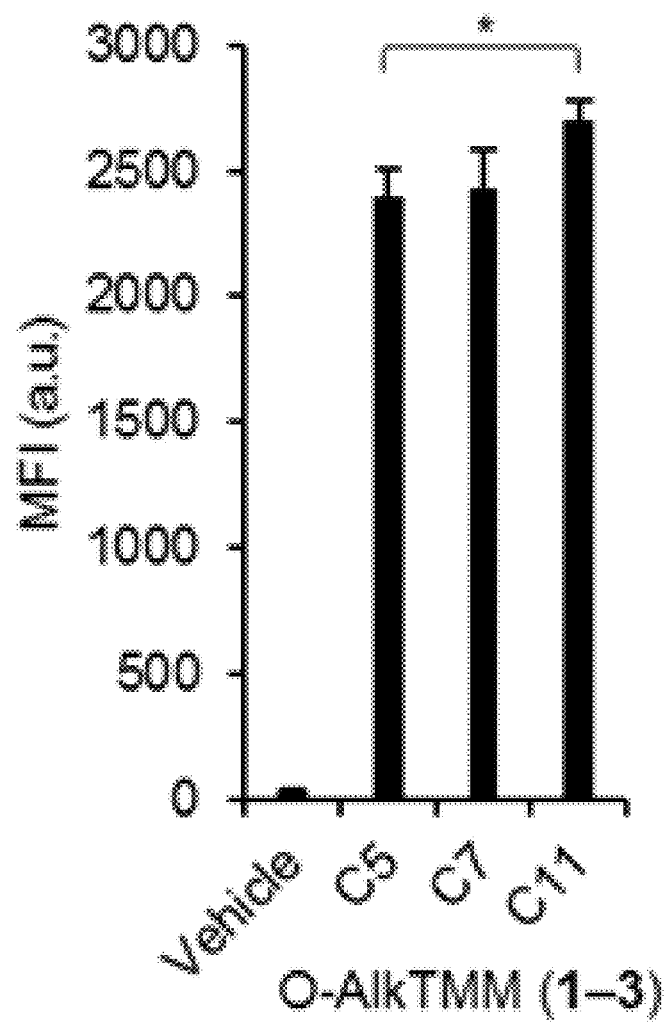
FIG. 61 shows the dependence of metabolic labeling on TMM reporter acyl chain length. Msmeg was incubated with 50 μM of AlkTMM-C5, AlkTMM-C7, or AlkTMM-C11 (or left untreated) for 4 h, reacted with Az488 by CuAAC, and analyzed by flow cytometry.

With compounds 1-6 in hand, the first objective was to evaluate the O-AlkTMM series (1-3) to determine whether changes in chain length had an impact on labeling efficiency. Native mycolic acids are α-branched and β-hydroxylated, and they contain anywhere from 22-100 total carbons, depending on the species. The shortened linear chain of the TMM reporter, O-AlkTMM-C7, was a fairly significant simplification of the native mycolate, but the compound was still efficiently incorporated into the mycomembrane. In this Example, it was hypothezied that longer-chain reporters would have favorable incorporation. To test this hypothesis, Msmeg was cultured in 50 μM of each reporter, then subjected to CuAAC reaction with an azido-488 fluorophore and analyzed by flow cytometry (FIG. 61). Although it was somewhat surprising to observe little difference in labeling between the compounds (a small increase was observed for the longer-chain analogue 3). There are criteria to be considered for selection of TMM reporter chain length for a given application. The smaller C5 and C7 reporters are conveniently water-soluble, whereas larger C11 (and higher) reporters require organic co-solvent (e.g., DMSO or ethanol) to solubilize. On the other hand, the TMM reporters with longer chains are more likely to faithfully replicate the biophysical properties of native TMM within a cellular environment.

Figure 62:
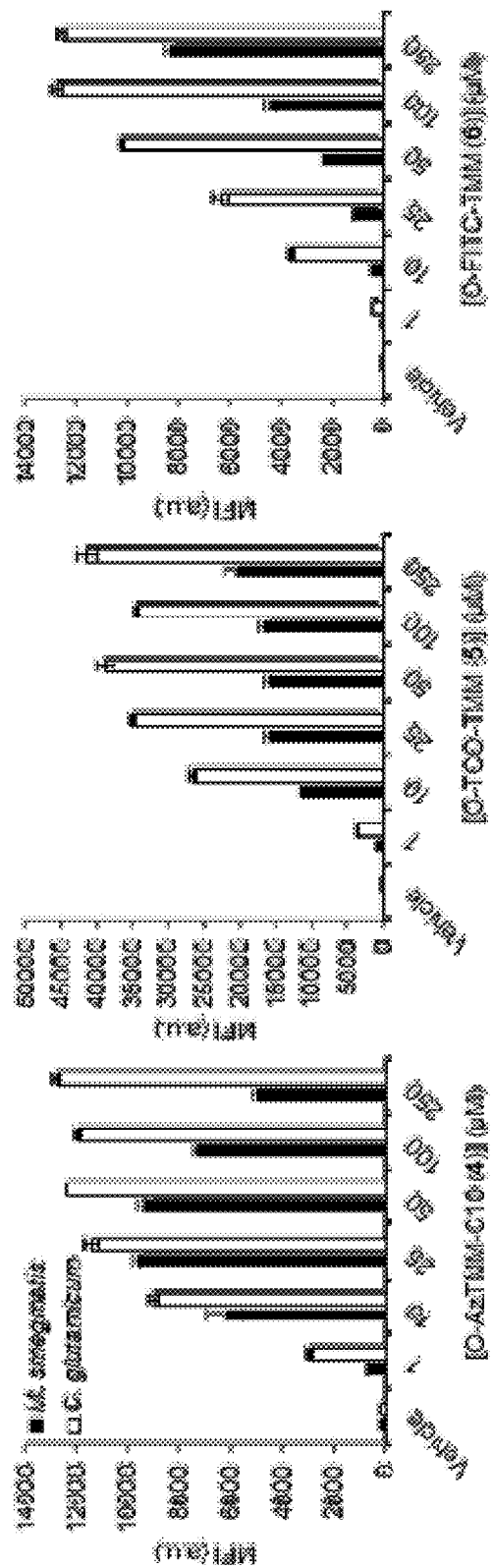
FIG. 62 shows concentration-dependent metabolic labeling of Msmeg and Cg using azide-, trans-cyclooctene-, and fluorophore-modified TMM reporters O-AzTMM-C10, O-TCO-TMM, and O-FITC-TMM. Msmeg or Cg was incubated with O-AzTMM-C10, O-TCO-TMM, or O-FITC-TMM (or left untreated) for 4 h, then in a second step the cells were reacted with DBCO-488 (for O-AzTMM-C10), tetrazine-Cy3 (for O-TCO-TMM), or left untreated (for O-FITC-TMM) and analyzed by flow cytometry. Error bars denote the standard deviation of three replicate experiments. MFI, mean fluorescence intensity; a.u., arbitrary units. *p value <0.05.

TMM reporter (1-3)-labeled bacteria must be fixed prior to carrying out traditional CuAAC reactions on the cell surface. By contrast, TMM reporters 4-6 were designed to enable probing of mycoloylation in living systems, which was investigated next. Each reporter was evaluated over the same concentration range (0-250 μM) in Msmeg and Cglut (FIG. 62). O-AzTMM-C10 (4) labeling was followed by SPAAC reaction on live cells with a dibenzocyclooctyne (DBCO)-488 fluorophore; O-TCO-TMM (5) labeling was followed by tetrazine ligation on live cells with a tetrazine-Cy3 fluorophore; since O-FITC-TMM (6) directly delivers the fluorophore during metabolic incorporation, no secondary step was required for this reporter. Cellular fluorescence was quantified by flow cytometry. All three reporters led to efficient metabolic labeling of both Msmeg and Cglut as compared to the control cells. Labeling saturation was observed for both O-AzTMM-C10 (4) and O-TCO-TMM (5) at approximately 25 μM concentration, whereas for O-FITC-TMM saturation occurred at higher concentrations (>100 μM), presumably due to the larger size of the fluorophore. Interestingly, the reporters with the larger TCO and FITC tags, 5 and 6, were incorporated into Cglut much more efficiently than in Msmeg. This could be due to increased uptake of the larger reporters across the mycomembrane of Cglut, which has shorter mycolic acids and higher fluidity than Msmeg. Notably, growth inhibition or altered cell morphology was not observed upon treatment of bacteria with compounds 1-6 at the highest tested concentrations, demonstrating the apparent non-perturbing nature of these reporters.

TMM reporters 4-6 provide the ability to probe mycoylation in live bacteria for the first time. O-FITC-TMM (6), or related fluorophore-modified TMM reporters (which can be readily accessed from 8 as shown in Scheme 3B), can be used when a one-step live-cell labeling workflow is desired. For example, one-step labeling may be preferred for its simplicity (e.g., fewer reagents and washes) or when there is concern about whether the secondary fluorophore (or other reagent) has sufficient access to the tagged biomolecule. Two-step labeling can be desirable for many reasons, including generally higher metabolic incorporation efficiency and the versatility to deliver virtually any type of secondary reagent to the tagged biomolecule without having to synthesize and evaluate a new reporter. The TMM reporters that allow two-step live-cell labeling workflows, O-AzTMM-C10 (4) and O-TCO-TMM (5), are both useful in these scenarios. TCO-tetrazine ligations, with rate constants ranging from $10^3$-$10^6$ $M^{-1}$ $s^{-1}$, are the fastest known bioorthogonal reactions, making them 3-6 orders of magnitude faster than SPAAC reactions employing DBCO, which have reported rate constants of approximately 0.3 $M^{-1}$ $s^{-1}$. Thus, it was hypothesized that O-TCO-TMM (5), in combination with the tetrazine ligation, would give optimal cell-surface labeling. To test this, Msmeg was treated with either 4 or 5 and then reacted with DBCO-488 or tetrazine-Cy3, respectively, for incubation times ranging from 1-30 min.

Figure 63:
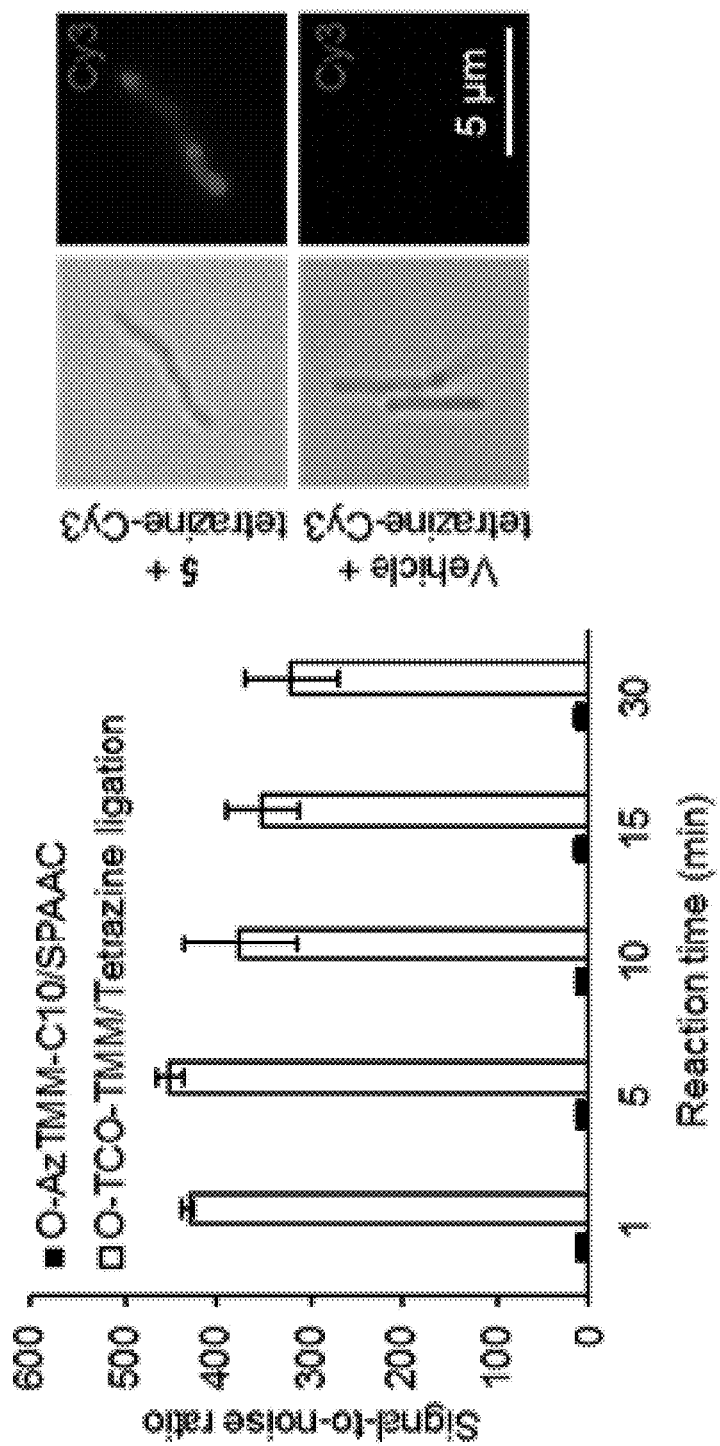
FIG. 63 shows cell-surface reaction kinetics comparison between O-AzTMM-C10 with SPAAC and O-TCO-TMM with tetrazine ligation. Msmeg was cultured in O-AzTMM-C10 or O-TCO-TMM (25 μM each) or left untreated, then reacted with DBCO-488 or tetrazine-Cy3 (20 μM each) for varying times and analyzed by flow cytometry. Error bars denote the standard deviation of three replicate experiments. (B) Fluorescence imaging of O-TCO-TMM-labeled Msmeg after 1 min tetrazine reaction. Scale bar (5 μm) applies to all images. Grayscale images are transmitted light images.

The signal-to-noise (S/N) ratios for each condition, which were determined by flow cytometry, are shown in FIG. 63. O-TCO-TMM-labeled cells could be detected by tetrazine ligation with a S/N ratio of >400:1 at only 1 min (FIG. 63). O-AzTMM-C10-labeled cells could also be detected in 1 min by SPAAC, although the S/N ratio was much lower at 13:1. Interestingly, the S/N ratio for the SPAAC reaction increased moderately with time (up to 17:1), while it dropped moderately for the tetrazine reaction (down to about 300:1). Overall, O-TCO-TMM (5), in conjunction with the tetrazine ligation, is considered to be an excellent reporter for rapid two-step labeling in living systems, and it should prove useful in situations where very low concentrations of reagents are needed (e.g., in animal infection models).

Figure 64A:
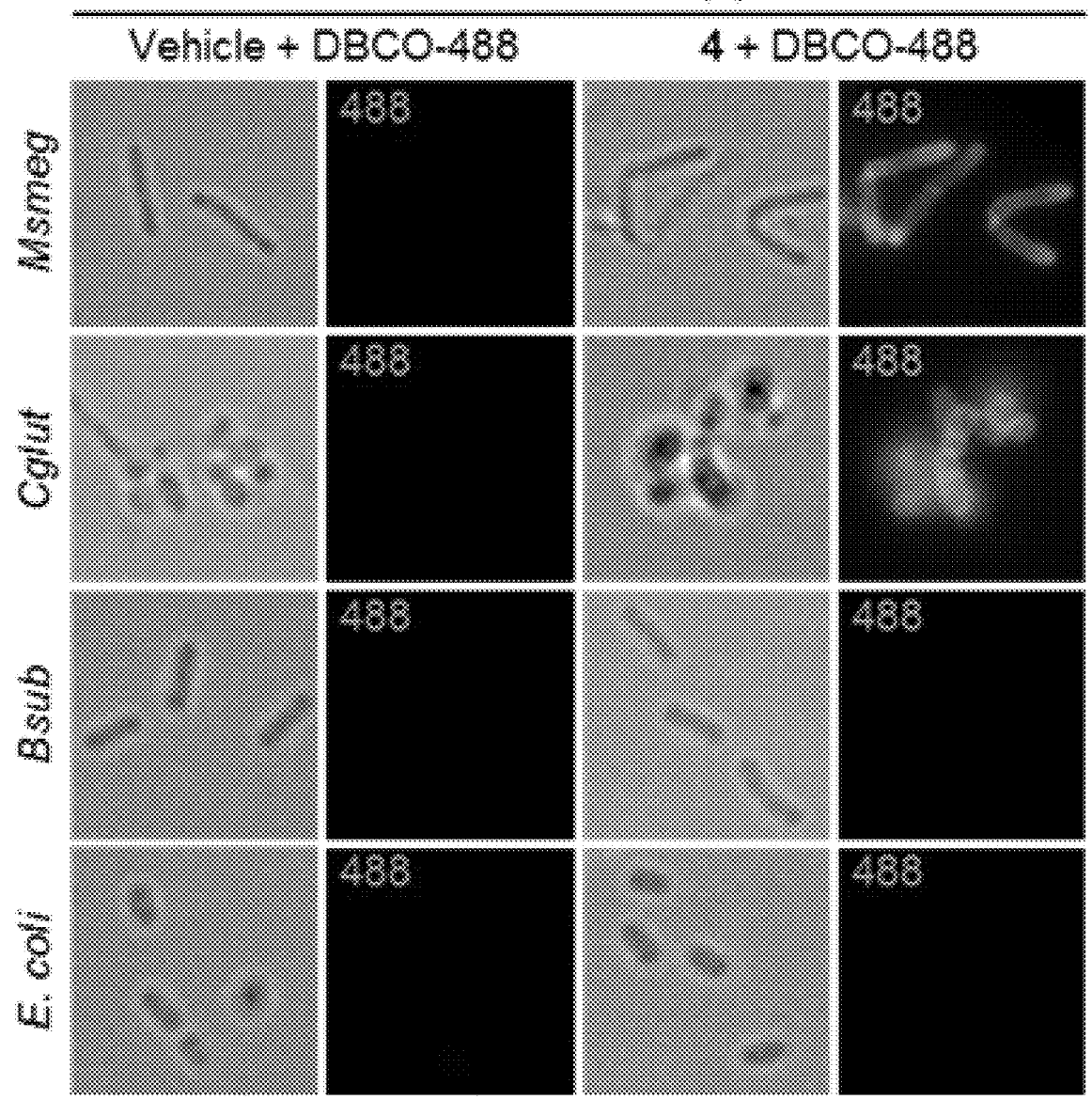
FIGS. 64(A)-(C) show the specificity of TMM reporters for MM-containing members of the Corynebacterineae suborder. Msmeg, Cglut, Bsub, or E. coli were incubated with (A): O-AzTMM-C10 (25 M), (B): O-TCO-TMM (25 M), (C): O-FITC-TMM (100 M), or left untreated for 4 h, then in a second step the cells were reacted with DBCO-488 (for AzTMM-C10), tetrazine-Cy3 (for O-TCO-TMM), or left untreated (for O-FITC-TMM) and analyzed by fluorescence microscopy. Scale bar (5 μm) applies to all images.
Figure 64B:
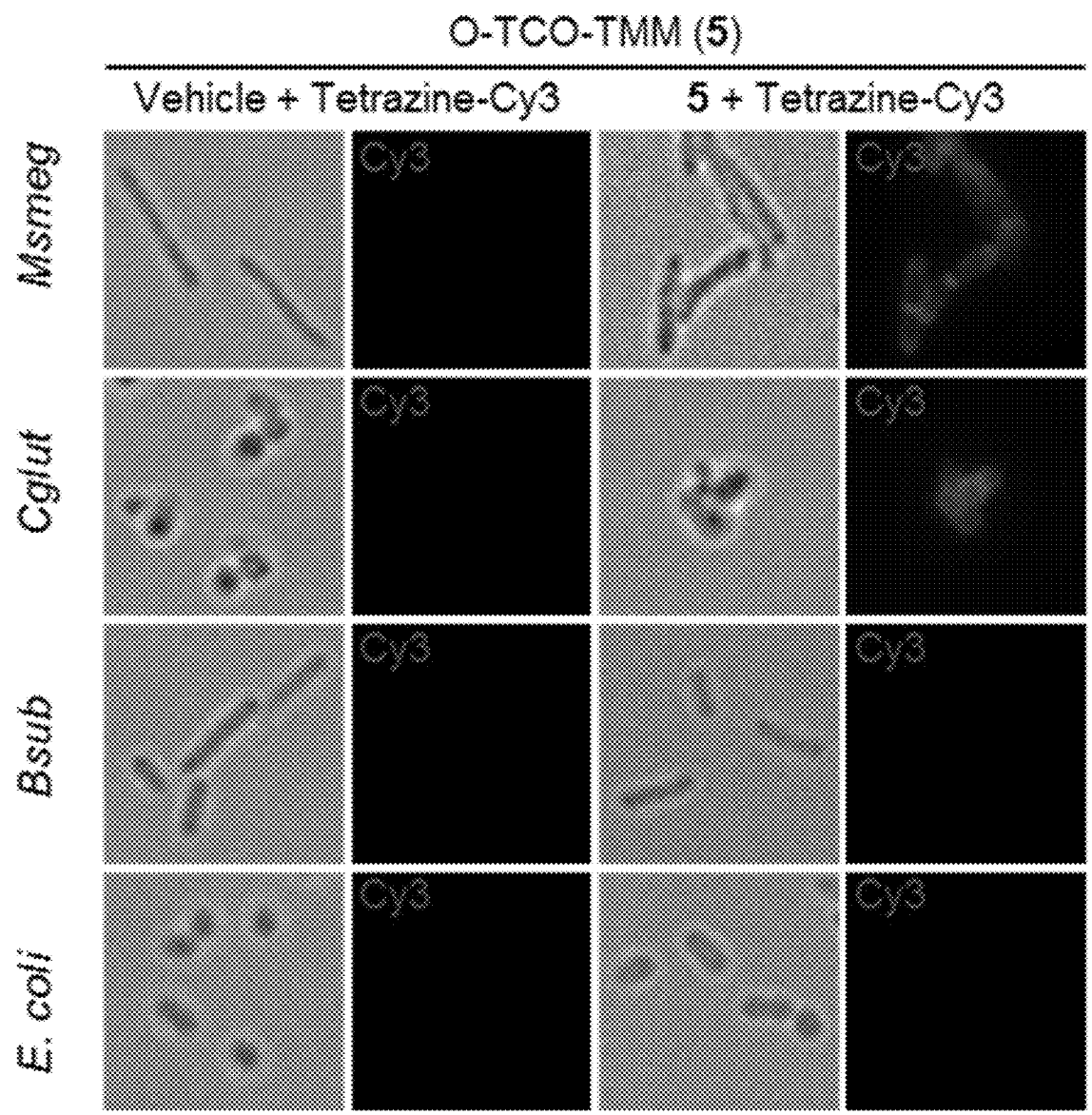
Figure 64C:
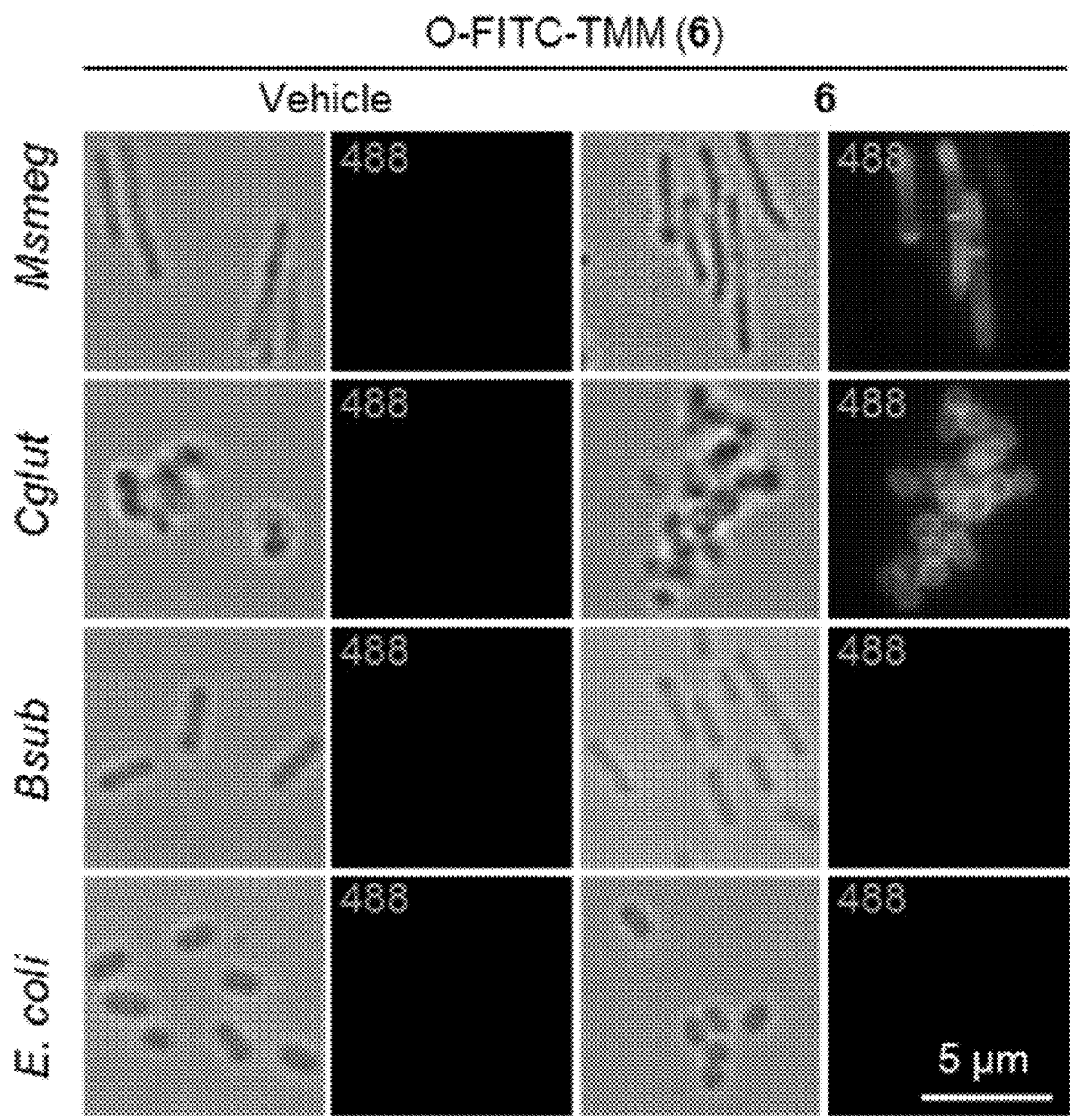
Figure 65A:
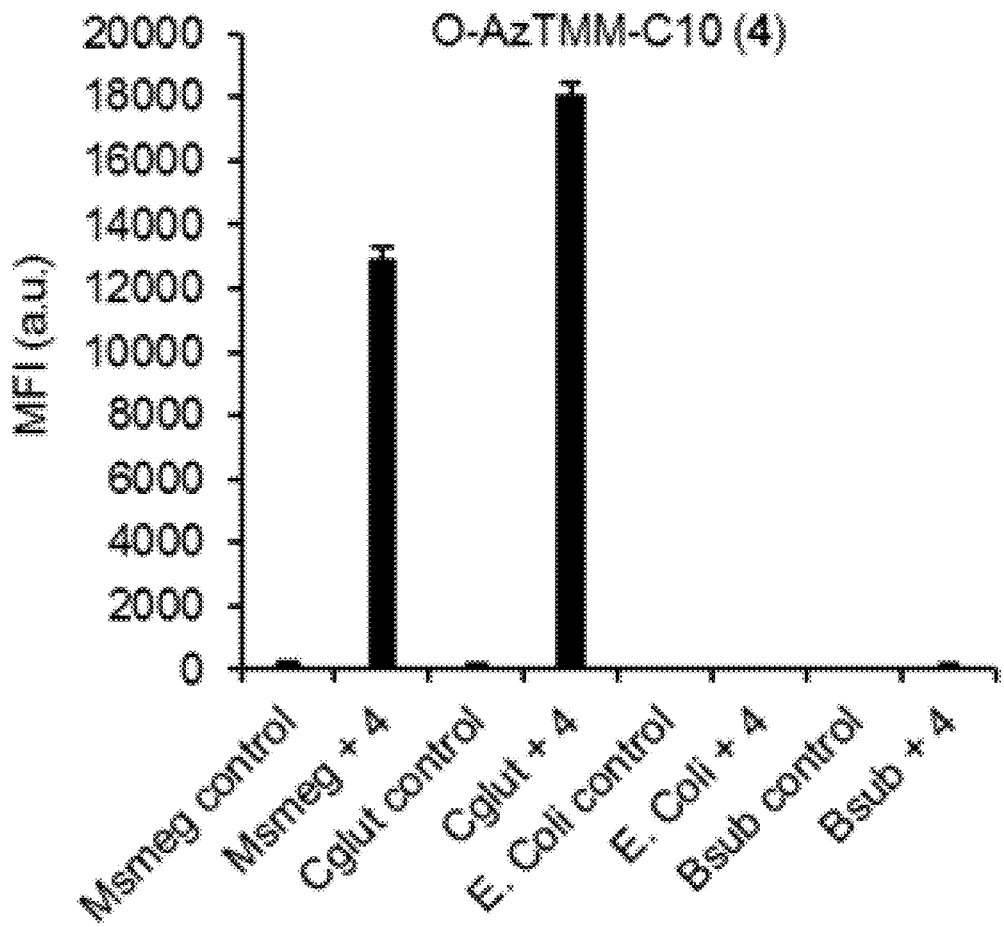
FIGS. 65(A)-(C) show specificity of TMM reporters for MM-containing members of the Corynebacterineae suborder. Msmeg, Cglut, Bsub, or E. coli were incubated with (A): O-AzTMM-C10 (25 M), (B): O-TCO-TMM (25 M), (C): O-FITC-TMM (100 M), or left untreated for 4 h, then in a second step the cells were reacted with DBCO-488 (for O-AzTMM-C10), tetrazine-Cy3 (for O-TCO-TMM), or left untreated (for O-FITC-TMM) and analyzed by fluorescence microscopy and flow cytometry. Error bars denote the standard deviation of three replicate experiments. MFI, mean fluorescence intensity; a.u., arbitrary units.
Figure 65B:
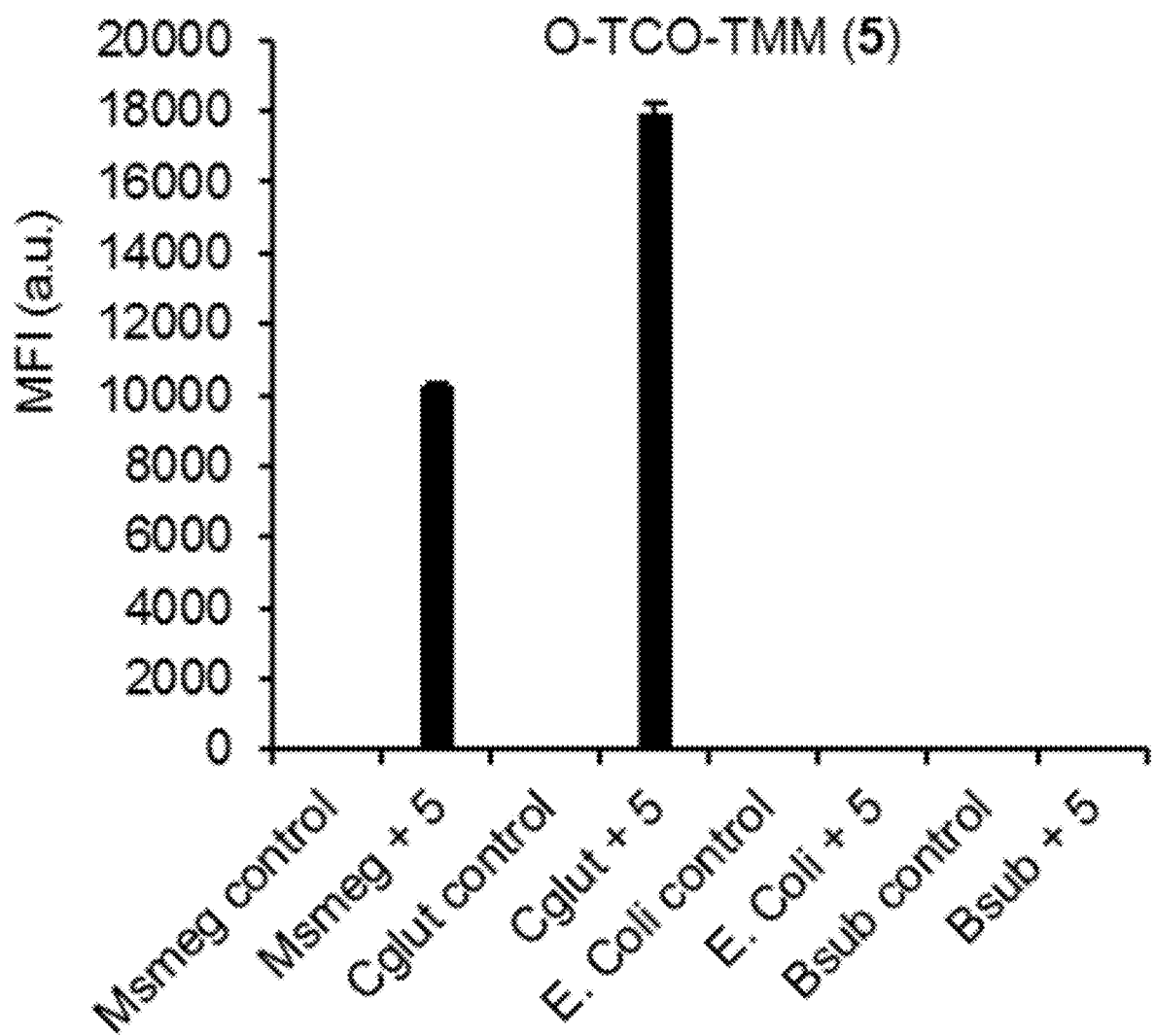
Figure 65C:
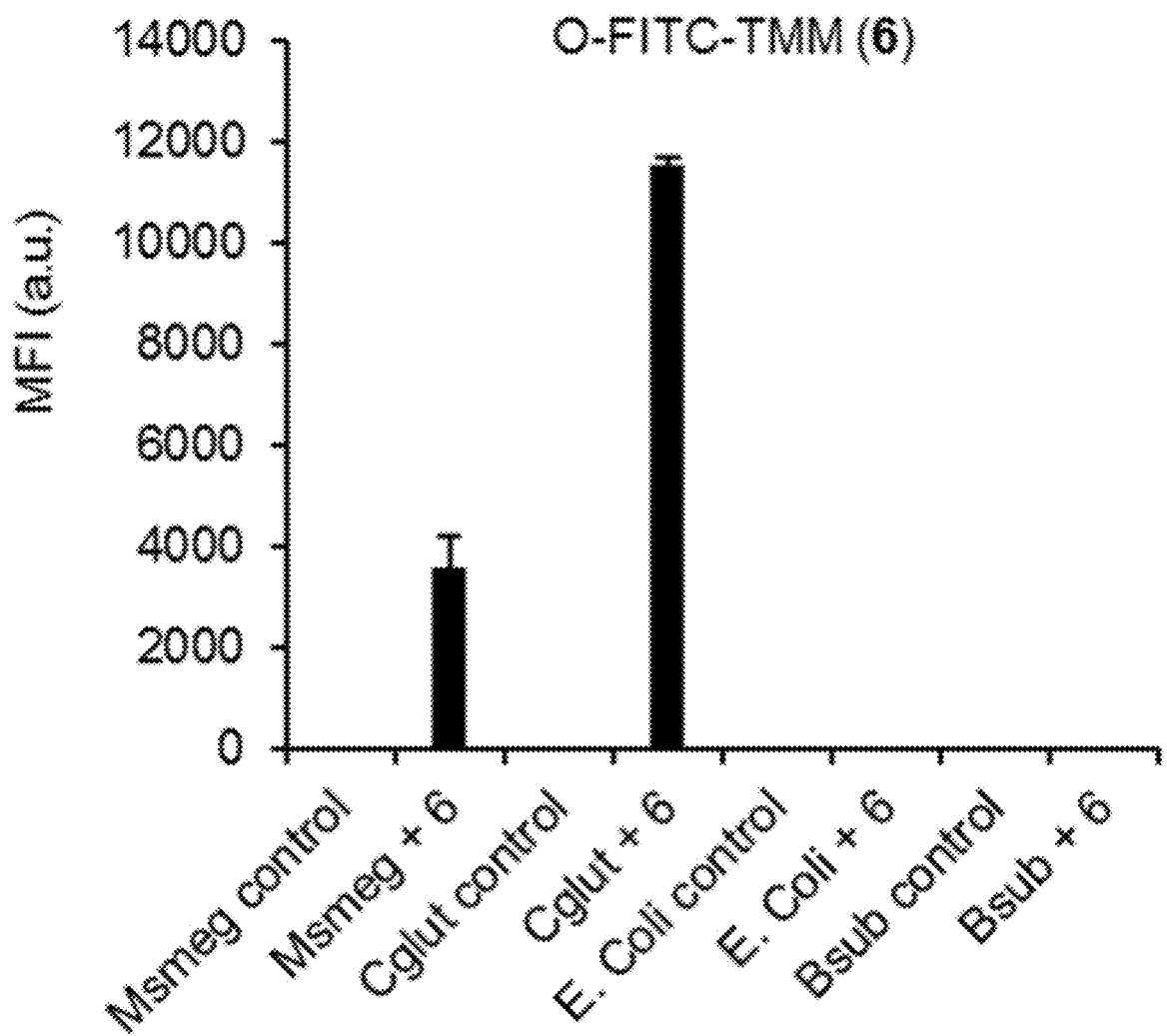

Only species in the Corynebacterineae suborder possess the mycomembrane and its associated biosynthetic pathways. To assess the specificity of TMM reporters 4-6 for mycomembrane-containing bacteria, labeling experiments were performed essentially as described above in Msmeg, Cglut, *Bacillus subtilis* (Bsub, a model Gram-positive organism), and *Escherichia coli* (*E. Coli*, a model Gram-negative organism). Cellular fluorescence was analyzed by fluorescence microscopy (FIGS. 64(A)-(C)) and quantified by flow cytometry (FIGS. 65(A)-(C)). Microscopy data indicated that the three new TMM reporters exhibited high specificity for members of the Corynebacterineae, with robust labeling of Msmeg and Cglut but no labeling of Bsub or *E. coli* (FIGS. 64(A)-(C)). Quantitative flow cytometry data was in full agreement with the microscopy data (FIGS. 65(A)-(C)). In addition, the microscopy images showed that metabolic labeling with compounds 4-6 resulted in cell-surface fluorescence concentrated at the poles and septa of bacteria, which is consistent with the polar growth mode of Corynebacterineae.

In summary, reported herein is the efficient synthesis and evaluation of a collection of TMM-based metabolic reporters that can facilitate research on the mycomembrane. The chemical tags appended to the TMM analogues' acyl chains allow labeling and analysis of mycoloylated cell envelope components through two-step strategies employing the major bioorthogonal reactions (CuAAC, SPAAC, or tetrazine ligation) or one-step strategies employing TMM reporters bearing pre-attached fluorophores. The reporters allow probing of mycoloylation and cell-surface engineering of living mycobacteria for the first time. The versatile synthetic intermediates (i.e., 4 and 8) and high specificity of TMM analogues for labeling mycobacteria, should allow TMM analogues to be exploited for the development of novel strategies for targeting mycobacteria with various types of chemical payload.

Example 4

Synthesis, Characterization & Metabolic Labeling of Bacteria of FRET Probes

FRET-TDM (5) was synthesized from diol 1 as shown in Scheme 4 and described below. (Compound numbering in this Example refers to Scheme 4)

General Methods for Synthesis.

Materials and reagents were obtained from commercial sources without further purification unless otherwise noted. Anhydrous solvents were obtained either commercially or from an alumina column solvent purification system. All reactions were carried out in oven-dried glassware under inert gas unless otherwise noted. Analytical TLC was performed on glass-backed silica gel 60 Å plates (thickness 250 m) and detected by charring with 5% $H_2SO_4$ in EtOH. Column chromatography was performed using flash-grade silica gel 32-63 m (230-400 mesh). $^1$H NMR spectra were recorded at 500 MHz with chemical shifts in ppm (δ) referenced to solvent peaks. $^{13}$C NMR spectra were recorded at 125 MHz. NMR spectra were obtained on a Varian Inova 500 instrument. Coupling constants (J) are reported in hertz (Hz). High-resolution electrospray ionization (HR ESI) mass spectra were obtained using a Waters LCT Premier XE using either raffinose or reserpine as the lock mass.

Scheme 4:

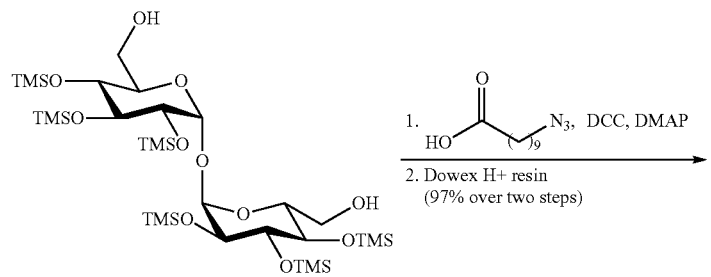

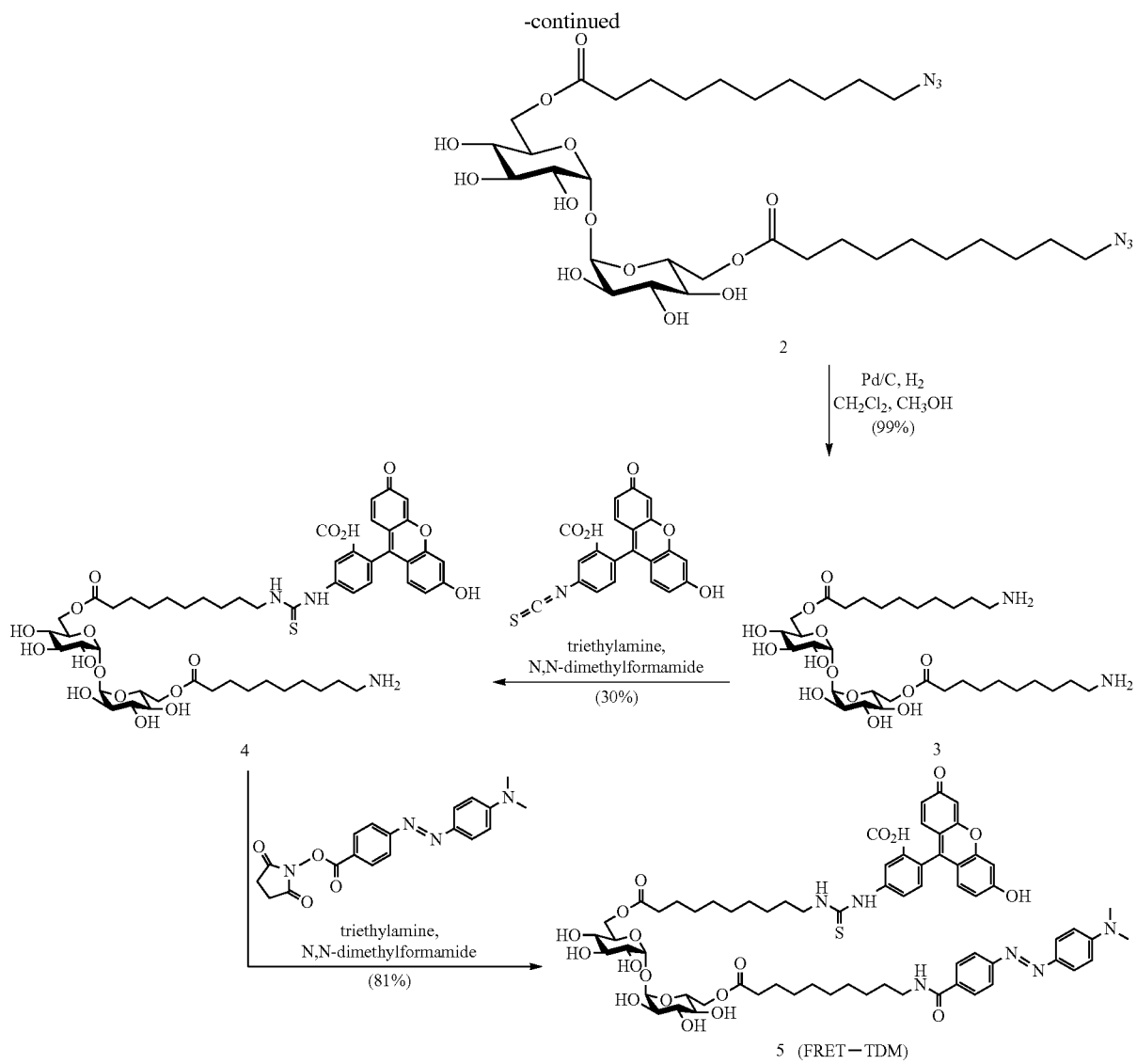

Di-6,6'-O-(10-azidodecanoyl)-α,α-D-trehalose (2)

Figure 41:
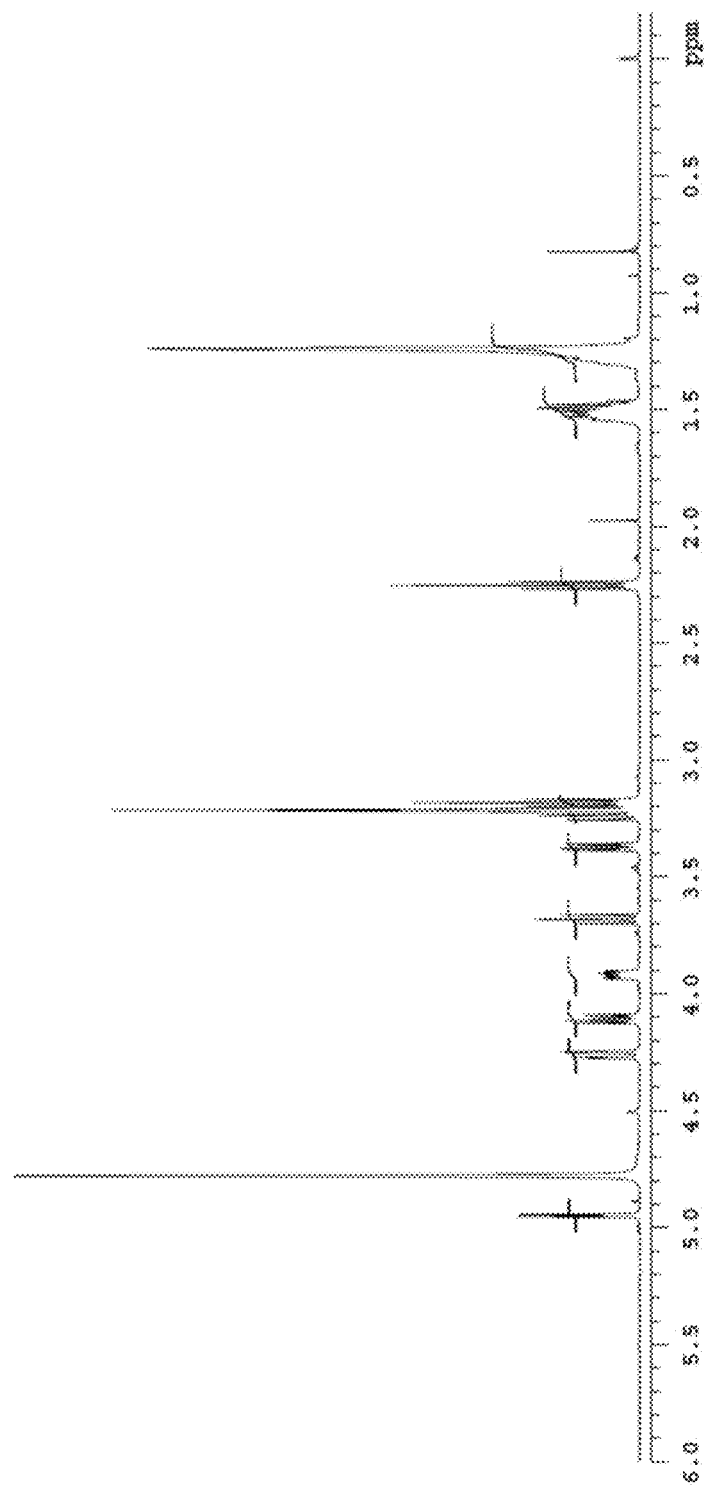
FIG. 41 shows a $^1H$ NMR spectrum of Di-6,6'-O-(10-azidodecanoyl)-α,α-D-trehalose.
Figure 42:
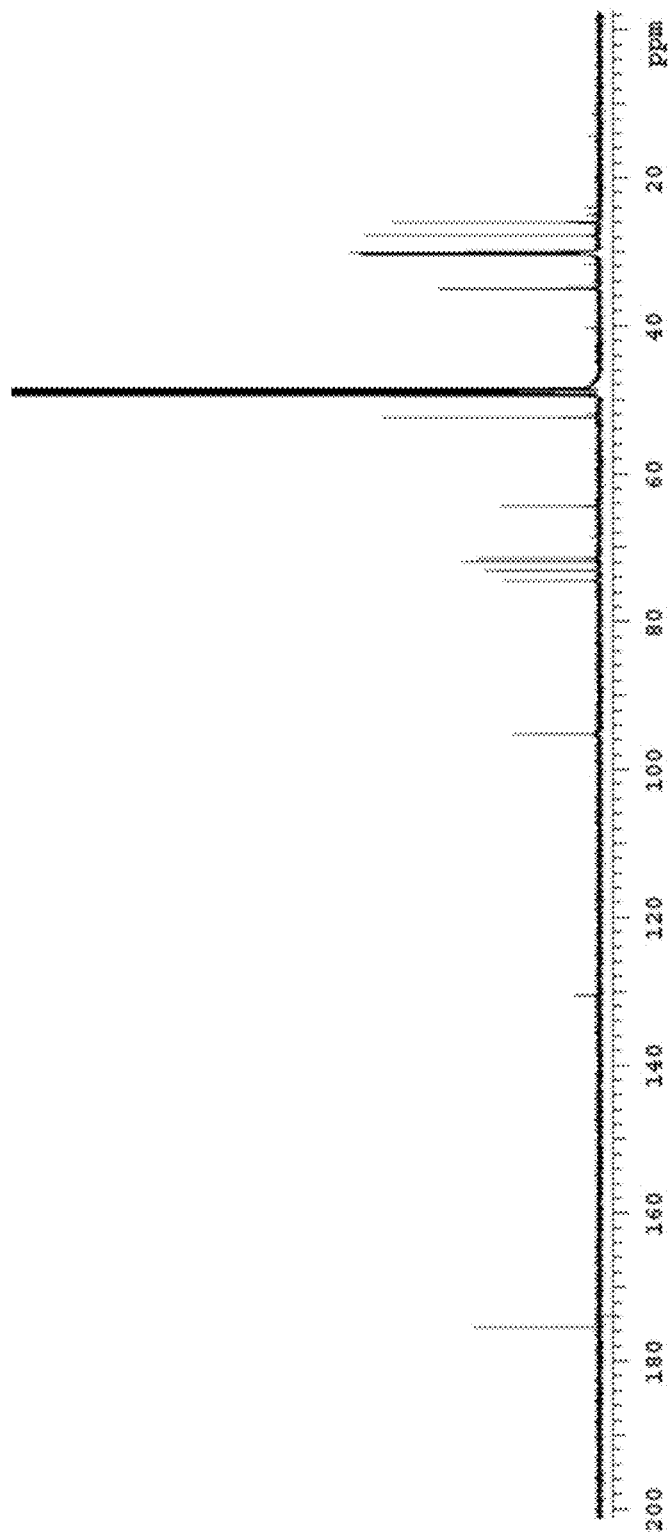
FIG. 42 shows a $^{13}C$ NMR spectrum of Di-6,6'-O-(10-azidodecanoyl)-α,α-D-trehalose.

An oven-dried round-bottom flask was charged with DCC (1.900 g, 9.209 mmol) and DMAP (0.190 g, 1.555 mmol). After drying the reagents under high vacuum and placing the flask under a nitrogen atmosphere, anhydrous $CH_2Cl_2$ (15 mL) was added. To the stirring solution was added 10-azidodecanoic acid (1.900 g, 8.908 mmol) followed by slow, dropwise addition of a freshly prepared solution of 2,3,4,2', 3',4'-hexakis-O-(trimethylsilyl)-α,α-trehalose 1 (1.00 g, 1.29 mmol) in anhydrous $CH_2Cl_2$ (15 mL). After 24 h, TLC (hexanes/ethyl acetate 5:1) showed generation of the diester product ($R_f$=0.65). The reaction was quenched by addition of excess $CH_3OH$ and concentrated by rotary evaporation. After resuspension of the crude product in $CH_2Cl_2$, the insoluble byproduct DCU was removed by filtration. The filtrate containing crude product was concentrated by rotary evaporation and purified by silica gel chromatography (hexanes/ethyl acetate 8:1 containing 1% $Et_3N$) to give the diester intermediate. The intermediate was dissolved in anhydrous $CH_3OH$ (80 mL) and placed under a nitrogen atmosphere. Dowex 50WX8-400 $H^+$ ion-exchange resin was added and the reaction was stirred for 1 h at room temperature, after which TLC ($CH_2Cl_2/CH_3OH$ 5:1) indicated that the reaction was complete ($R_f$=0.51). After the ion-exchange resin was filtered off, the filtrates were concentrated by rotary evaporation, and filtered to give 2 (0.960 g, 97% over two steps) as a white solid. $^1H$ NMR (FIG. 41) (500 MHz, $CD_3OD$) δ 4.95 (d, J=4.0 Hz, 2H, H-1), 4.26 (dd, J=2.0, 12 Hz, 2H, H-6a or 6b), 4.11 (dd, J=5.0, 12 Hz, H-6a or 6b), 3.91 (ddd, J=1.5, 5.0, 9.5 Hz, 2H, H-5), 3.68 (t, J=10 Hz, 2H, H-3), 3.37 (dd, J=3.5, 9.5 Hz, 2H, H-2), 3.23 (t, J=10.5 Hz, 2H, H-4), 3.18 (t, J=6.5 Hz, 4H, $CH_2$—$N_3$), 2.25 (t, J=7.5 Hz, 4H, α-$CH_2$), 1.54-1.46 (m, 8H, $CH_2$s), 1.30-1.23 (m, 20H, $CH_2$s); $^{13}C$ NMR (FIG. 42) (100 MHz, $CD_3OD$) δ 175.4, 95.2, 74.5, 73.1, 71.9, 71.5, 64.4, 52.4, 35.0, 30.4, 30.2, 30.1, 29.9, 27.8, 26.0. ESI MS negative mode: calcd. for $C_{19}H_{29}O_{12}$ [M–H]$^-$ m/z, 731.38; found, 731.33.

Di-6,6'-O-(10-aminodecanoyl)-α,α-D-trehalose (3)

Figure 43:
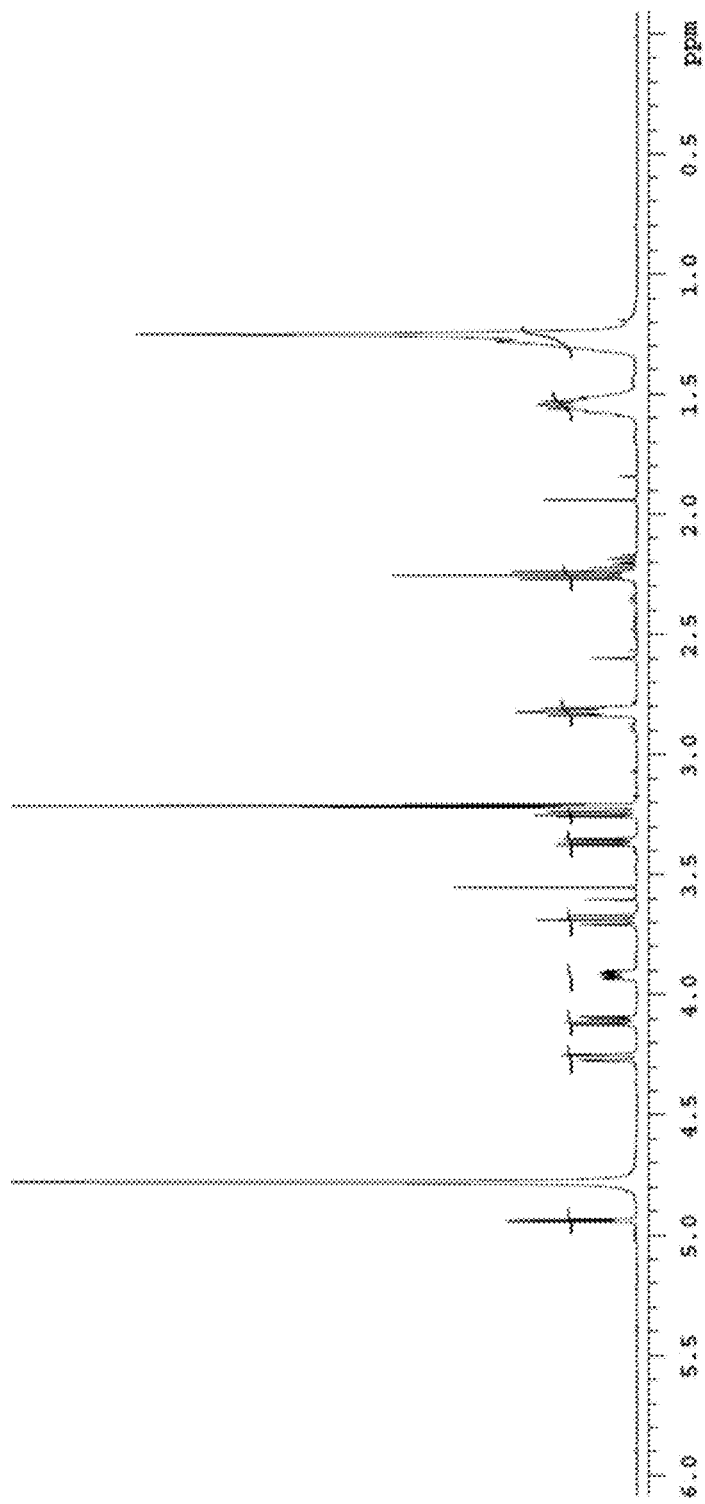
FIG. 43 shows a $^1H$ NMR spectrum of Di-6,6'-O-(10-aminodecanoyl)-α,α-D-trehalose.
Figure 44:
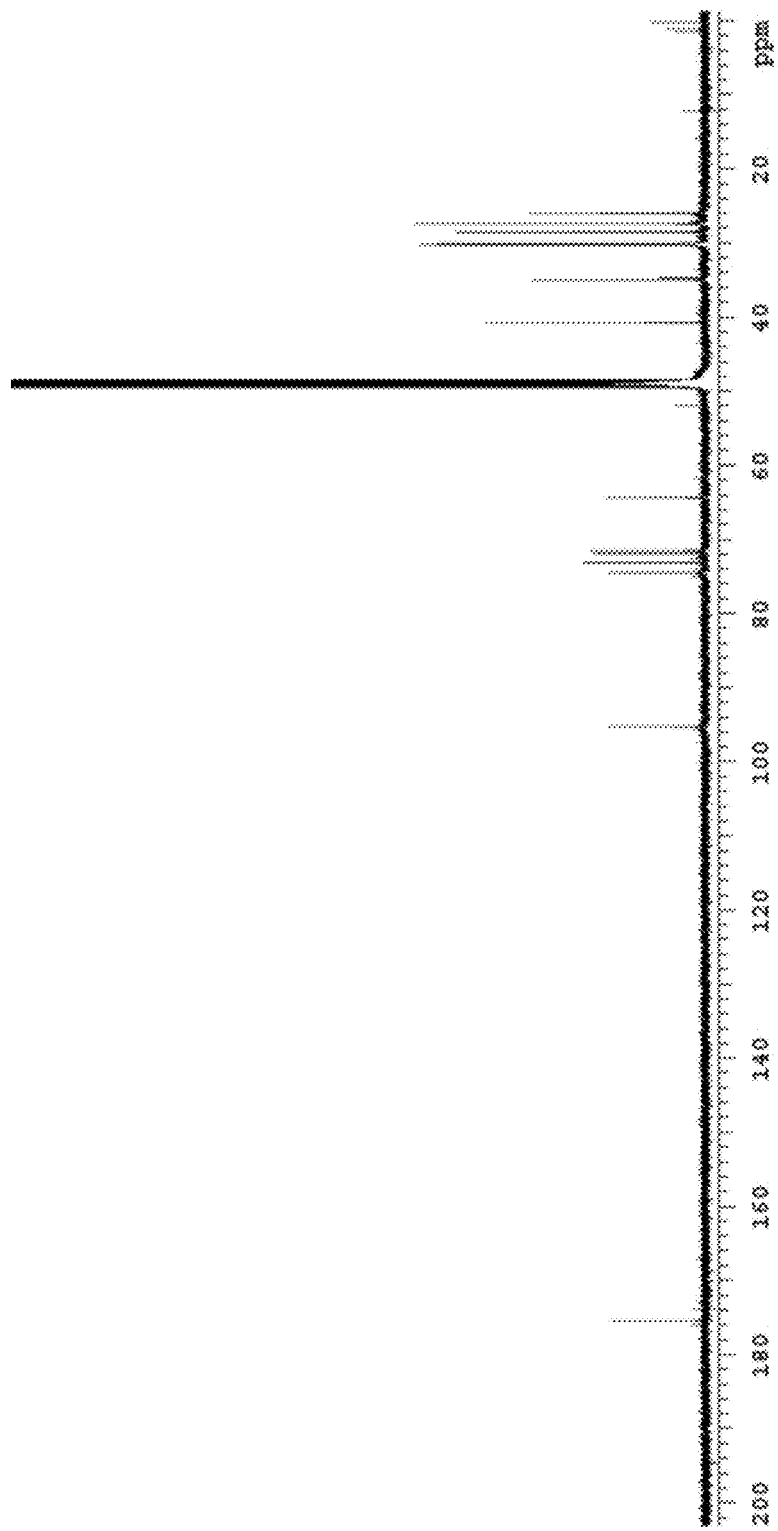
FIG. 44 shows a $^{13}C$ NMR spectrum of Di-6,6'-O-(10-aminodecanoyl)-α,α-D-trehalose.

To a solution of compound 2 (150 mg, 0.205 mmol) in $CH_2Cl_2:CH_3OH$ (2:1, 6 mL) under an argon atmosphere was added Pd/C (15 mg). A hydrogen-filled balloon was connected to the reaction flask and the argon atmosphere was exchanged for hydrogen. After stirring under a hydrogen atmosphere at room temperature overnight, the reaction mixture was filtered through Celite and the filtrate was concentrated by rotary evaporation to give the reduced product 3 (139 mg, 99%) as a white solid. $^1$H NMR (FIG. 43) (500 MHz, CD$_3$OD): δ 4.94 (d, J=4.0 Hz, 2H, H-1), 4.26 (dd, J=2.5, 12.5 Hz, 2H, H-6a or H-6b), 4.11 (dd, J=5.5, 11.5 Hz, 2H, H-6a or H-6b), 3.92 (ddd, J=2.0, 5.5, 10.5 Hz, 2H, H-5), 3.69 (t, J=9.5 Hz, 2H, H-3), 3.36 (dd, J=3.5, 9.5 Hz, 2H, H-2), 3.24 (t, J=10 Hz, 2H, H-4), 2.82 (t, J=7.5 Hz, 4H, CH$_2$—NH$_2$), 2.26 (t, J=7.0 Hz, 4H, α-CH$_2$), 1.58-1.51 (m, 8H, CH$_2$s), 1.33-1.22 (m, 20H, CH$_2$s). $^{13}$C NMR (FIG. 44) (125 MHz, CD$_3$OD): 174.42, 95.30, 74.51, 73.15, 71.89, 71.49, 64.35, 40.77, 35.00, 30.24, 30.21, 30.11, 30.09, 28.55, 27.39, 26.00. HR ESI MS positive mode: calcd. for C$_{32}$H$_{61}$NO$_{13}$ [M+H]$^+$: 681.4174, found: 681.4171.

6-O-(10-aminodecanoyl)-6'-O-(10-[(fluorescein-5-yl)thioureido]decanoyl)-α,α-D-trehalose (4)

Figure 45:
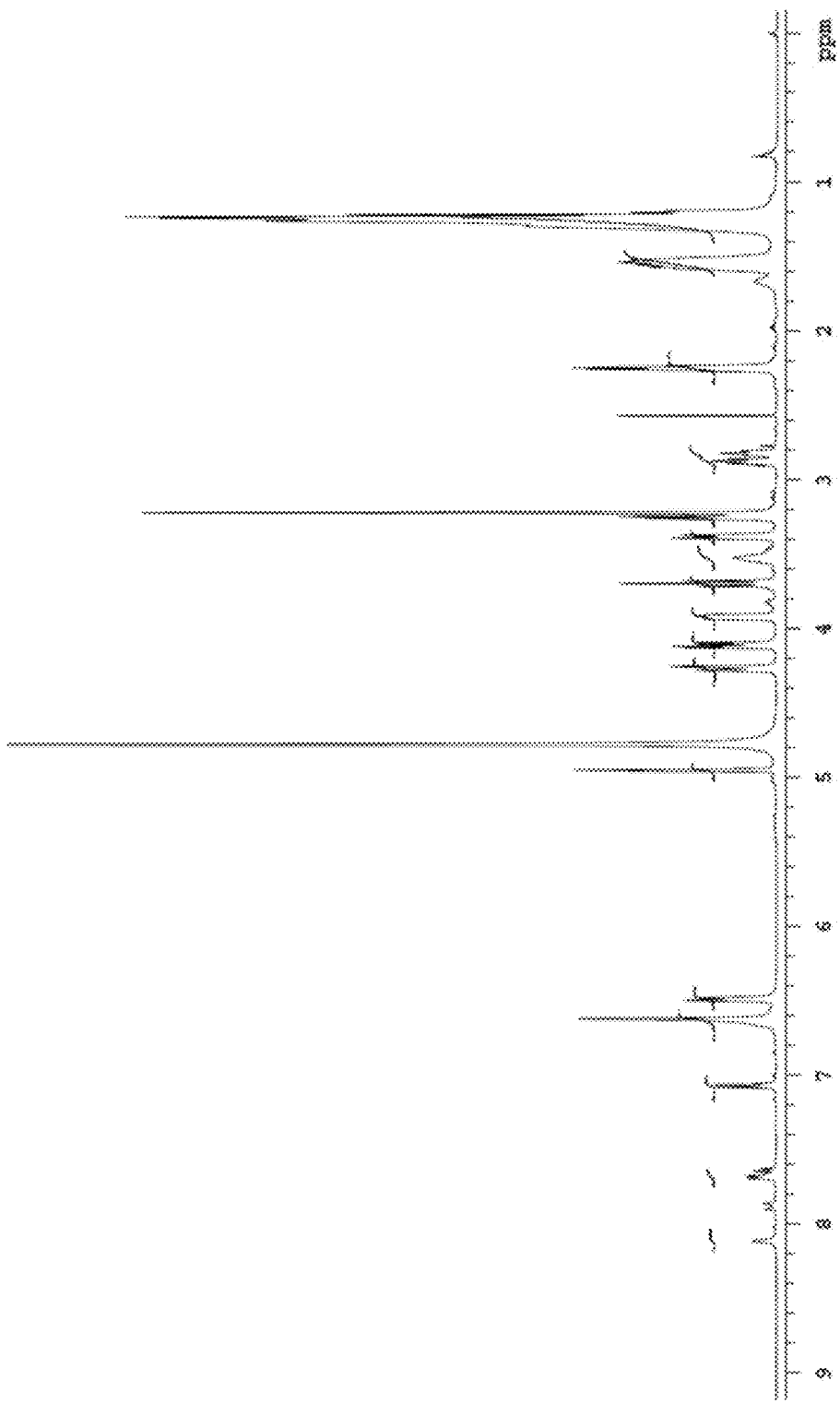
FIG. 45 shows a $^1H$ NMR spectrum of 6-O-(10-aminodecanoyl)-6'-O-(10-[(fluorescein-5-yl)thioureido]decanoyl)-α,α-D-trehalose.
Figure 46:
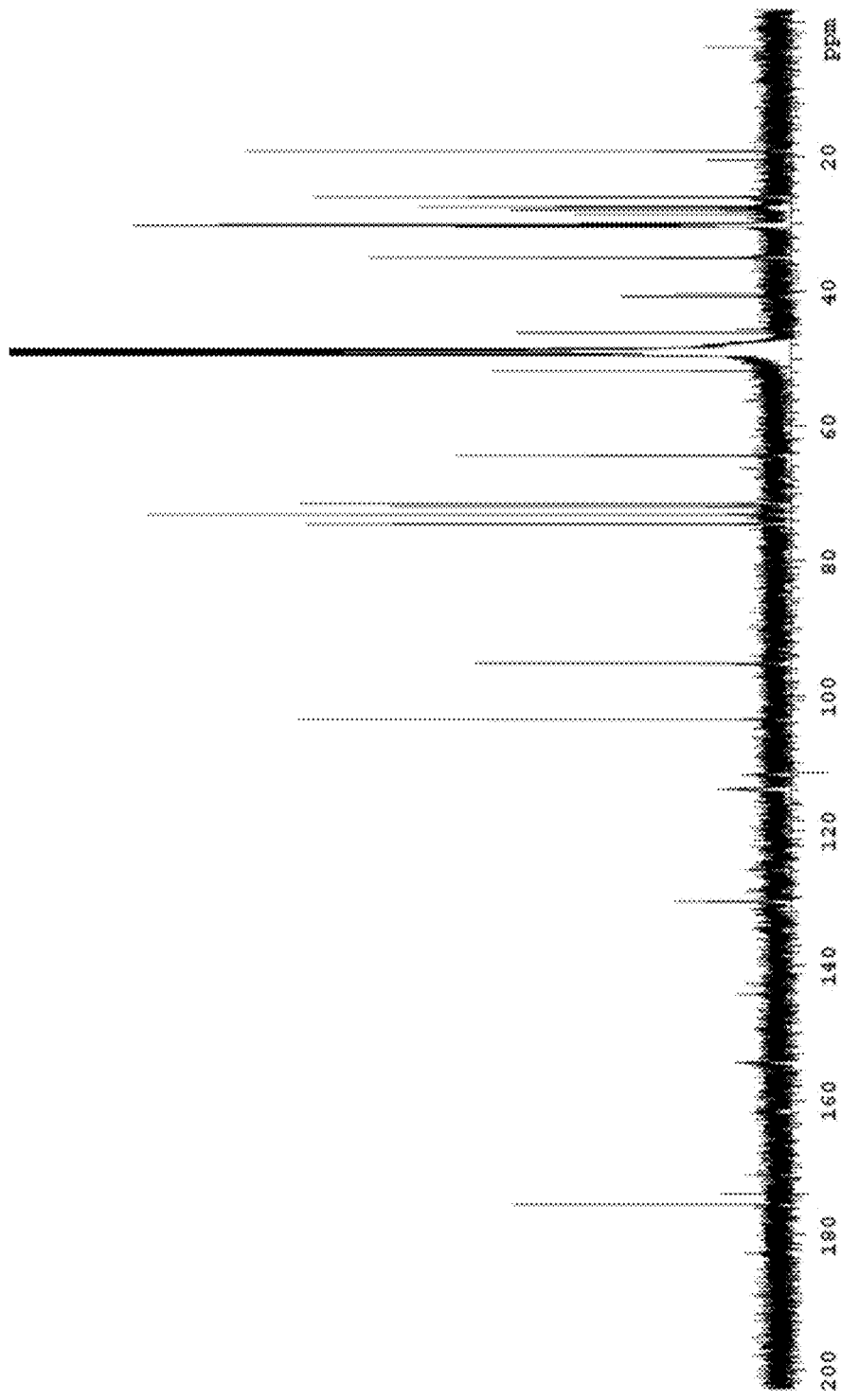
FIG. 46 shows a $^{13}C$ NMR spectrum of 6-O-(10-aminodecanoyl)-6'-O-(10-[(fluorescein-5-yl)thioureido]decanoyl)-α,α-D-trehalose.

To a solution of compound 3 (30 mg, 0.044 mmol) stirring in CH$_3$OH (1 mL) was added a solution of fluorescein isothiocyanate (FITC, 17 mg, 0.044 mmol) and Et$_3$N (8 μL, 0.08 mmol) dissolved in N,N-dimethylformamide (DMF) (4 mL). After stirring for 6 h, TLC (n-BuOH/EtOH/H$_2$O, 5:3:2) showed optimal conversion of 3 to 4. The reaction mixture was concentrated by rotary evaporation and purified using a Biotage Isolera One automated flash chromatography system (2×10 g C18 columns in sequence; 30% CH$_3$CN in H$_2$O→70% CH$_3$CN in H$_2$O) to give product 4 (14 mg, 30%) as a yellow solid. $^1$H NMR (FIG. 45) (500 MHz, CD$_3$OD) δ 8.11 (s, broad, 1H), 7.69 (d, J=8.5 Hz, 1H), 7.08 (d, J=8.0 Hz, 1H), 6.67-6.59 (m, 4H), 6.49 (d, J=7.5 Hz, 2H), 4.96 (d, J=4.0 Hz, 2H, H-1 and H-1'), 4.27 (dd, J=2.5, 11.5 Hz, 2H, H-6a or H-6b and H-6a' or H-6b'), 4.11 (dd, J=5.5, 11.5 Hz, 2H, H-6a or H-6b and H-6a' or H-6b'), 3.94-3.91 (m, 2H, H-5 and H-5'), 3.70 (t, J=9.5 Hz, 2H, H-3 and H-3'), 3.56-3.49 (m, 2H, CH$_2$—NH-fluoresceinyl), 3.40-3.37 (m, 2H, H-2 and H-2'), 3.26-3.22 (m, 2H, H-4 and H-4'), 2.89-2.81 (m, 2H, CH$_2$—NH$_2$), 2.27-2.23 (m, 4H, α-CH$_2$s), 1.60-1.48 (m, 8H, CH$_2$s), 1.33-1.19 (m, 20H, CH$_2$s). $^{13}$C NMR (FIG. 46) (125 MHz, CD$_3$OD): δ 182.70, 175.44, 173.88, 171.23, 161.95, 154.39, 144.28, 142.67, 130.47, 129.02, 125.80, 113.87, 111.74, 103.49, 95.17, 74.52, 73.14, 71.88, 71.48, 64.37, 46.16, 40.77, 35.08, 35.00, 30.42, 30.34, 30.26, 30.23, 30.10, 30.08, 30.07, 29.90, 28.54, 27.97, 27.56, 27.50, 27.36, 26.05, 25.98. HR ESI MS positive mode: m/z calcd. for C$_{53}$H$_{71}$N$_3$O$_{18}$S [M+2H]$^{2+}$: 535.7305, found: 535.7337.

6-O-(10-(dabcyl)amidodecanoyl)-6'-O-(10-[(fluorescein-5-yl)thioureido]decanoyl)-α,α-D-trehalose (5, FRET-TDM)

Figure 40:
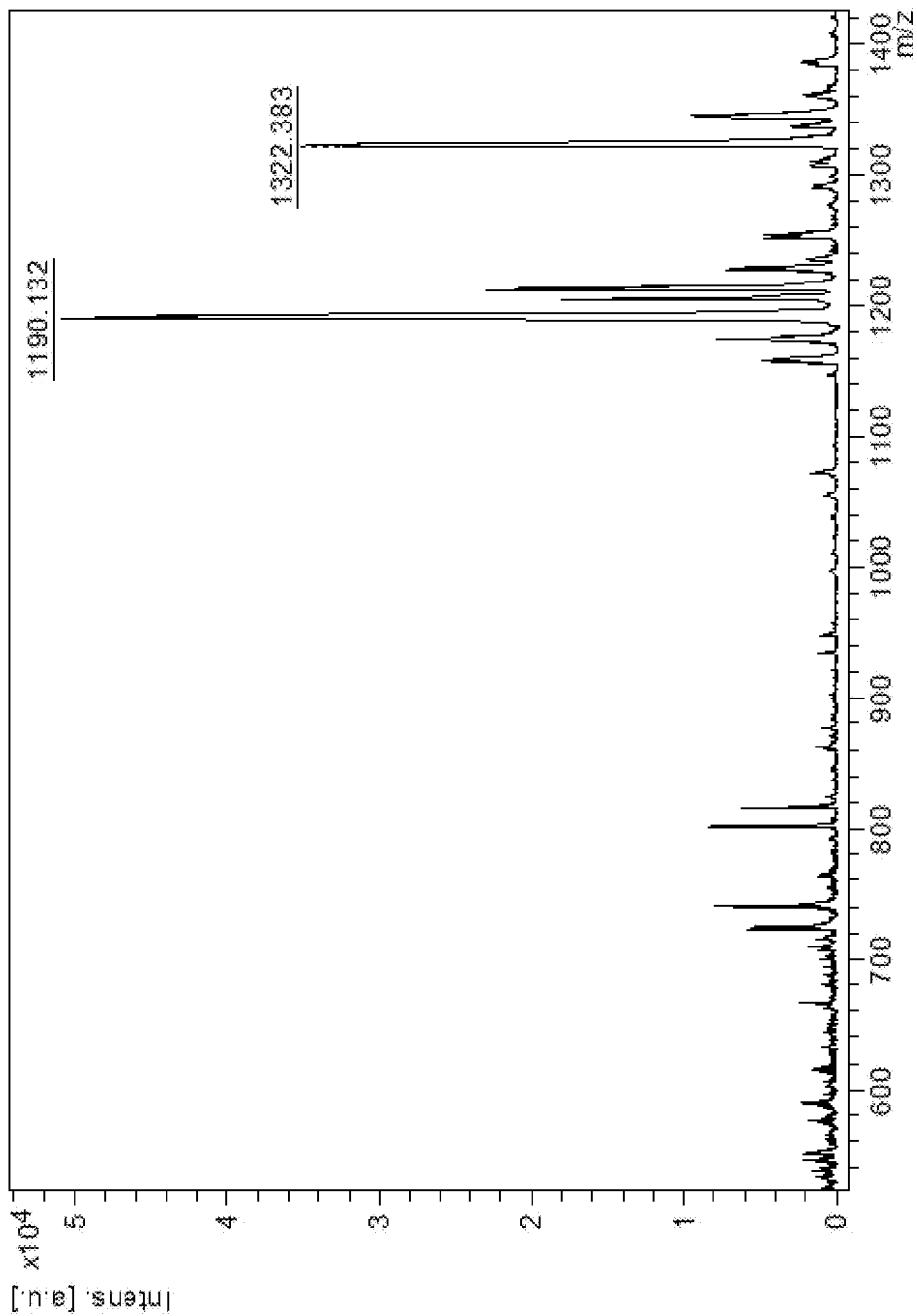
FIG. 40 shows a matrix-assisted laser desorption/ionization-mass spectrometry (MALDI-MS) spectrum of a disclosed FRET-TDM probe.
Figure 47:
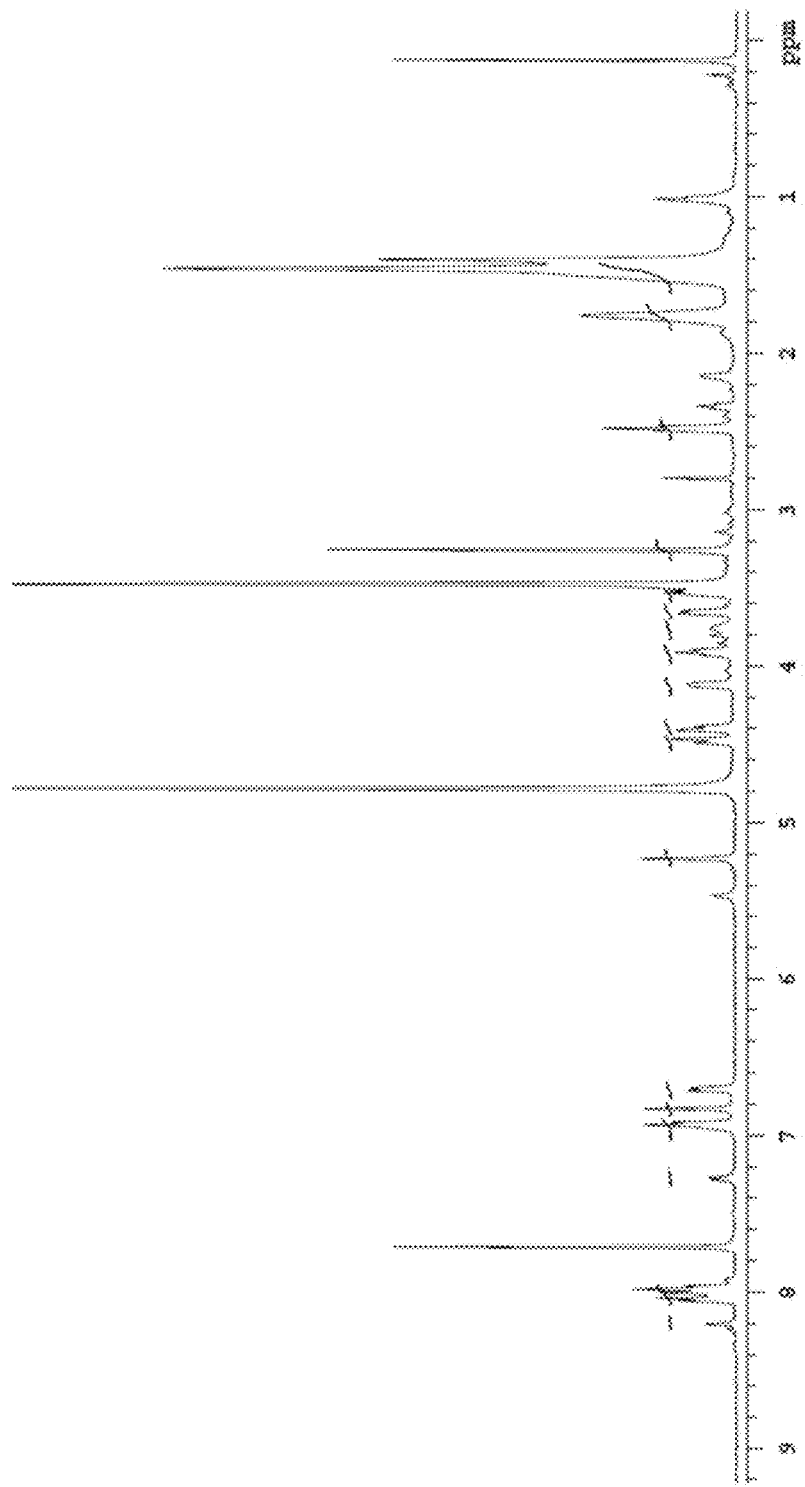
FIG. 47 shows a $^1H$ NMR spectrum of 6-O-(10-aminodecanoyl)-6'-O-(10-[(fluorescein-5-yl)thioureido]decanoyl)-α,α-D-trehalose.
Figure 48:
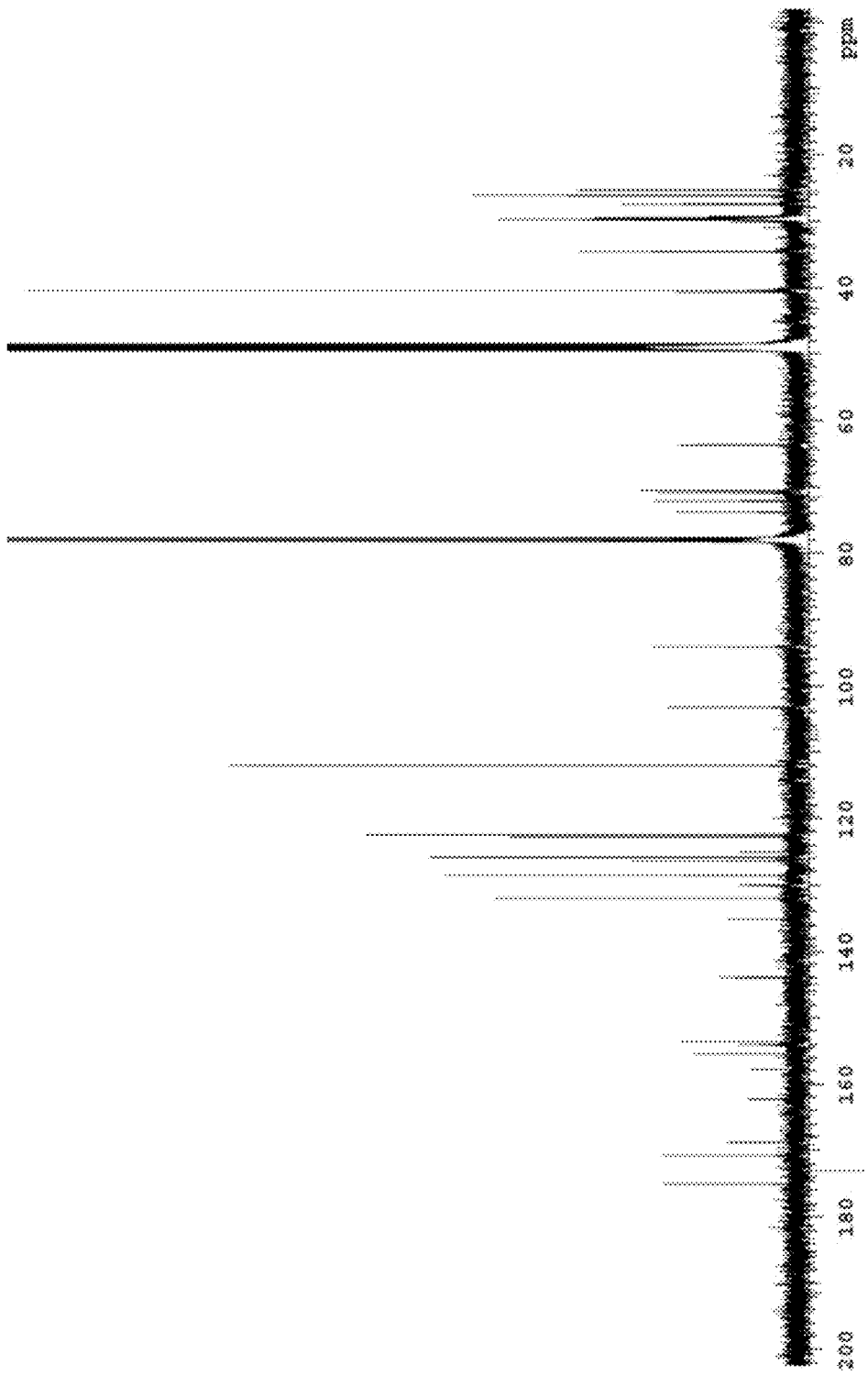
FIG. 48 shows a $^{13}C$ NMR spectrum of 6-O-(10-(dabcyl)amidodecanoyl)-6'-O-(10-[(fluorescein-5-yl)thioureido]decanoyl)-α,α-D-trehalose.

To a solution compound 4 (10 mg, 0.009 mmol) stirring in CH$_3$OH (0.5 mL) was added a solution of dabcyl NHS ester (3 mg, 0.009 mmol) and Et$_3$N (4 μL, 0.03 mmol) dissolved in DMF (2 mL). After stirring for 5 h, TLC (n-BuOH/EtOH/H$_2$O, 5:3:2) showed complete consumption of 3. The reaction mixture was concentrated by rotary evaporation and purified using a Biotage Isolera One automated flash chromatography system (2×10 g C18 columns in sequence; 30% CH$_3$CN in H$_2$O→70% CH$_3$CN in H$_2$O) to give product 5 (10 mg, 81%) as an orange-yellow solid. $^1$H NMR (FIG. 47) (500 MHz, CD$_3$OD containing 10% CDCl$_3$) δ 8.21 (s, broad, 1H), 8.06-7.96 (m, 7H), 7.27 (d, J=8.0 Hz, 1H), 6.96-6.90 (m, 4H), 6.83 (s, broad, 2H), 6.70 (d, J=8.0 Hz, 2H), 5.23 (d, J=4.0 Hz, 2H, H-1 and H-1'), 4.48 (dd, J=2.0, 11.5 Hz, 2H, H-6a or H-6b and H-6a' or H-6b'), 4.40 (dd, J=5.5, 12.5 Hz, 2H, H-6a or H-6b and H-6a' or H-6b'), 4.15-4.09 (m, 2H, H-5 and H-5'), 3.91 (t, J=8.5 Hz, 2H, H-3 and H-3'), 3.84-3.87 (m, 2H, CH$_2$—NH— fluoresceinyl), 3.68-3.63 (m, 2H, H-2 and H-2'), 3.56-3.50 (m, 4H, H-4, H-4', and CH$_2$—NH-dabcyl), 3.26 (s, 6H, dabcyl CH$_3$s), 2.48 (t, J=7.5 Hz, 4H, α-CH$_2$s), 1.86-1.79 (m, 8H, CH$_2$s), 1.58-149 (m, 20H, CH$_2$s). $^{13}$C NMR (FIG. 48) (125 MHz, CD$_3$OD containing 10% CDCl$_3$): δ 175.07, 170.83, 168.82, 162.31, 157.84155.45, 154.02, 153.60, 144.07, 143.94, 135.16, 132.03, 130.00, 128.52, 125.04, 122.77, 122.43, 111.99, 103.24, 94.14, 73.82, 72.21, 70.91, 63.72, 45.12, 40.67, 40.44, 30.10, 29.84, 29.79, 29.73, 29.68, 29.63, 29.58, 29.48, 29.46, 29.26, 27.47, 27.35, 26.09, 25.29. HR ESI MS positive mode: m/z calcd. for C$_{68}$H$_{86}$N$_6$O$_{19}$S [M+2H]$^{2+}$: 661.2834, found: 661.2787. The FRET-TDM probe was also characterized via MALDI-MS showing M+H at 1322 and fragmentation peak at 1190 (FIG. 40).

FRET Quenching Efficiency of FRET-TDM-1.

Figure 49:
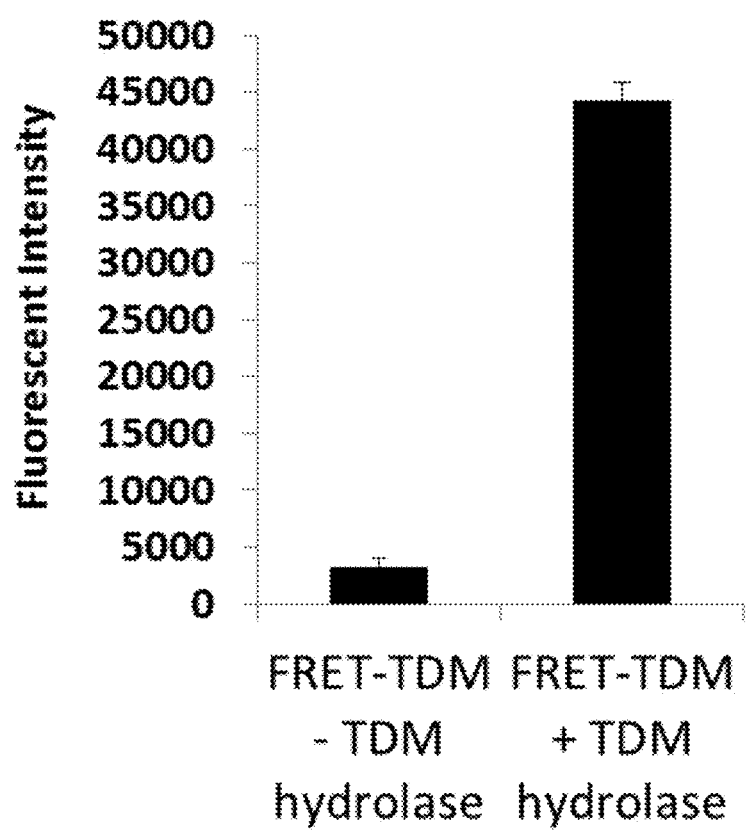
FIG. 49 shows a plot demonstrating the FRET-TDM capability of a disclosed compound.

The FRET-TDM compound was investigated for its ability to act as a FRET probe that is detectable following biological metabolism. Specifically, the FRET-TDM (10 μM) was incubated in the presence of 500 nM TDMH in Tris buffer versus Tris buffer alone for 1 min. Samples were then analyzed using a fluorescence plate reader. The results shown in FIG. 49 indicate that the disclosed trehalose compounds may be used as FRET probes.

FRET Quenching Efficiency of FRET-TDM-2.

Figure 50:
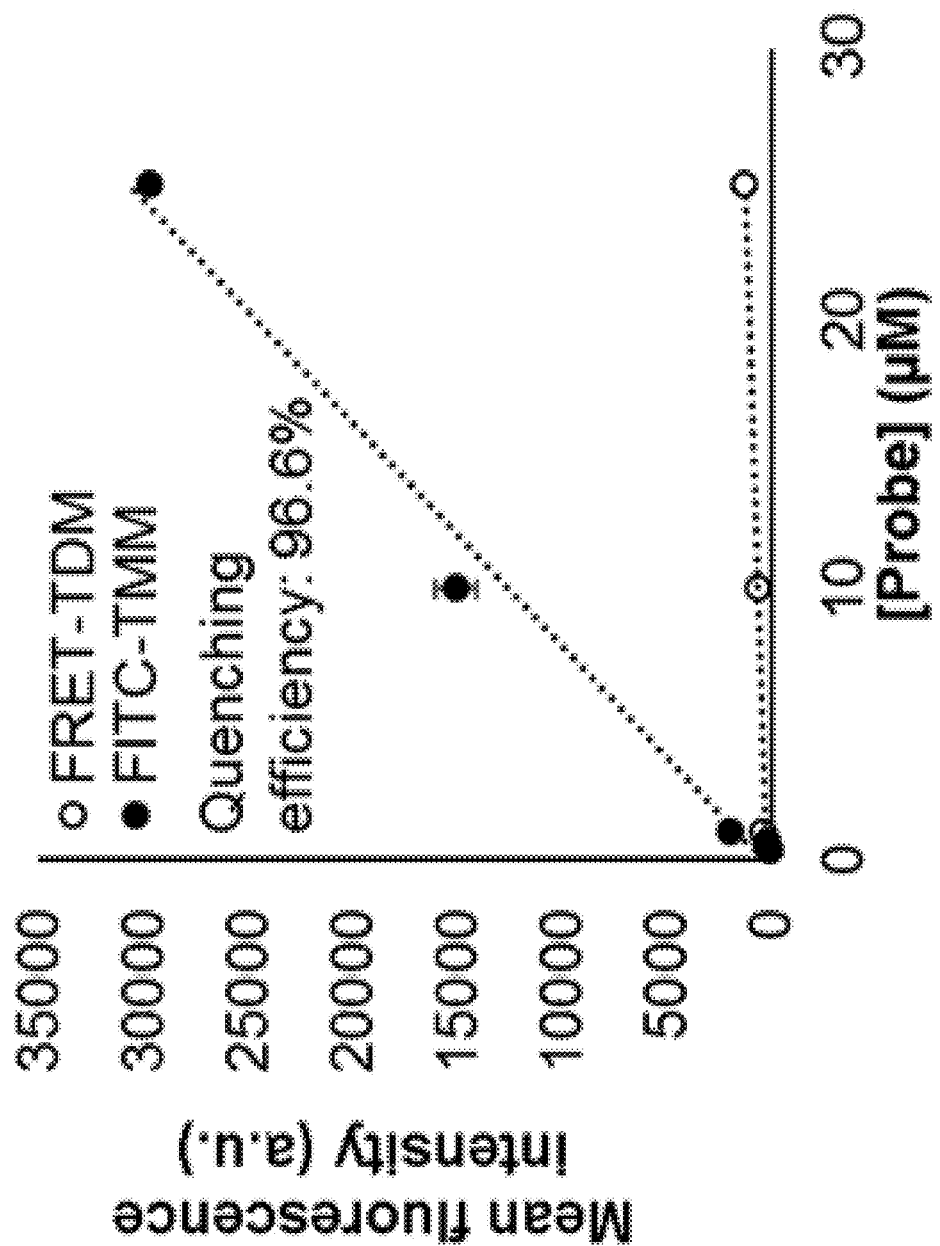
FIG. 50 shows a plot of fluorescence turn-on of FRET-TDM in the presence of recombinant M. smegmatis TDMH.

To determine the quenching efficiency of FRET-TDM in its intact "dark" state versus in its cleaved "bright" state, the fluorescence (Ex 488/Em 525) of varying concentrations of FRET-TDM and FITC-TMM (which is the unquenched product of TMDH-catalyzed cleavage of FRET-TDM) in HEPES buffer (50 mM, pH 7.4) were measured using a Tecan F200 multimodal plate reader. After performing a linear fit of the fluorescence data, the quenching efficiency of FRET-TDM was calculated to be 96.6% (FIG. 50).

Activation of FRET-TDM by Recombinant, Purified TDM Hydrolase.

Figure 51:
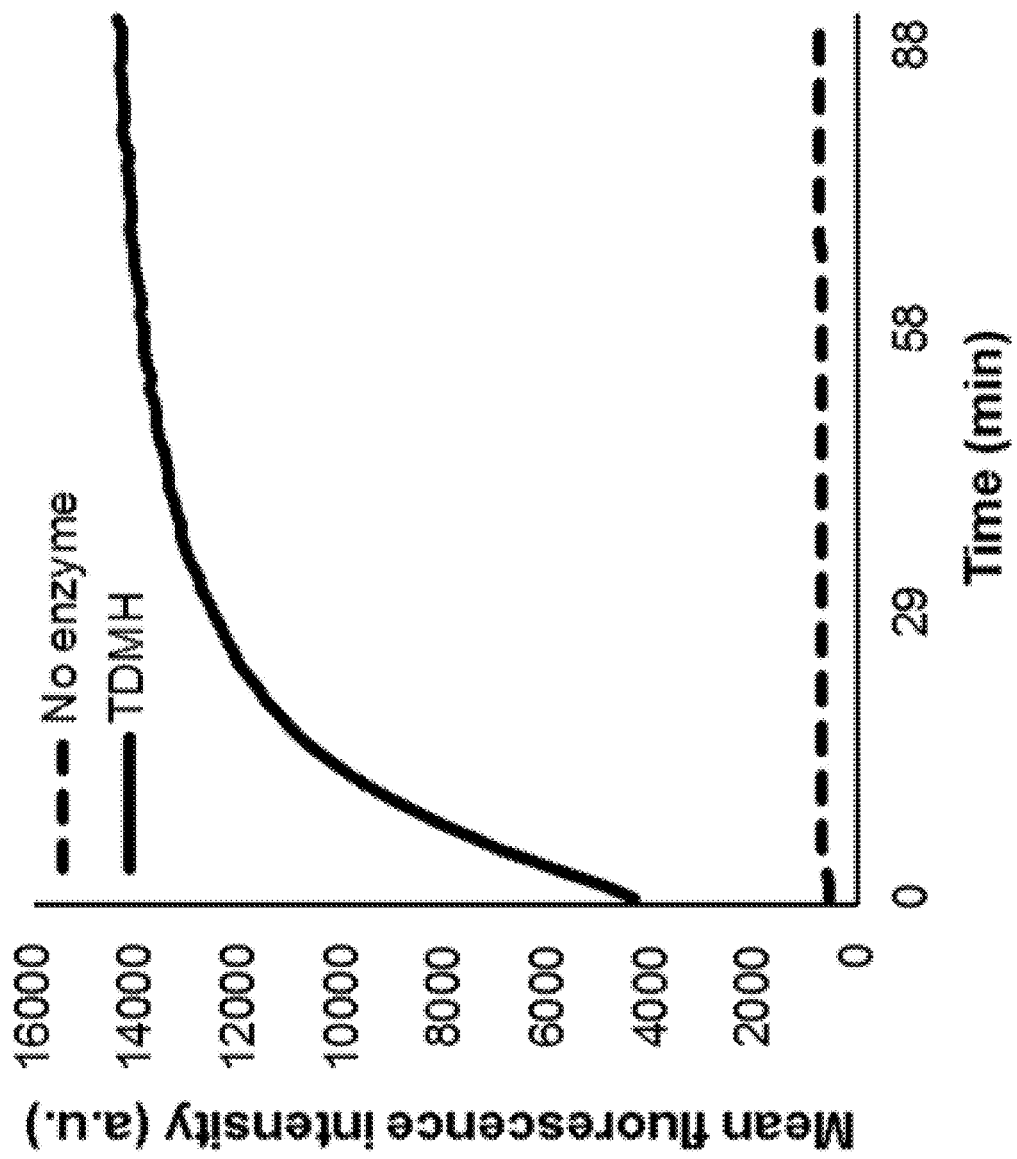
FIG. 51 shows a plot of fluorescence turn-on of 1 μM FRET-TDM in the presence of recombinant M. smegmatis TDMH.

His$_6$-tagged Trehalose dimycolate hydrolase (TDMH) from *M. smegmatis* was expressed and purified from *E. coli* as described. FRET-TDM (0.1-10 μM) was incubated in the presence (or absence) of TDMH (500 nM) in HEPES buffer (50 mM, pH 7.4) at 37° C. and fluorescence (Ex 488/Em 525) was monitored using a Tecan F200 multimodal plate reader. Saturable, time-dependent fluorescence was observed in the presence of TDMH but not in the no-enzyme control (FIG. 51).

Activation of FRET-TDM by TDM Hydrolase in *E. coli* Lysate.

Figure 52:
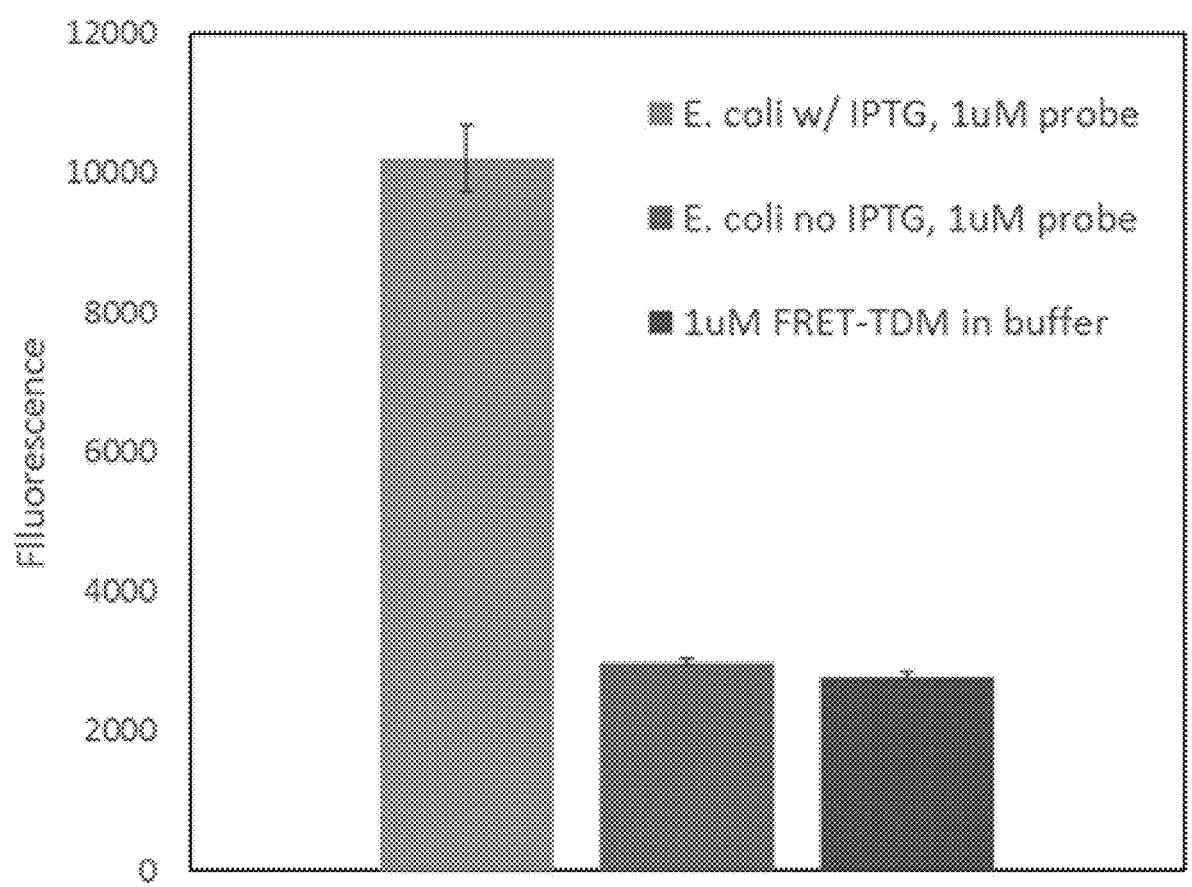
FIG. 52 shows a plot of fluorescence of 1 μM FRET-TDM by E. coli that was (i) induced to express TDMH by addition of IPTG (orange) or (ii) not induced to express TDMH (green).

The specificity of FRET-TDM activation by TDMH was tested in a more complex background of cell lysate. TDMH-expressing *E. coli* was either induced to express TDMH by addition of isopropyl β-D-1-thiogalactopyranoside (IPTG) or left uninduced (in this case, no TDMH would be present since it is not endogenous to *E. coli*), then grown in LB medium at 37° C. to an optical density (600 nm) of approximately 1. The cells were pelleted, washed, and lysed into HEPES buffer (50 mM, pH 7.4). The protein concentrations of the lysates were assessed by Bradford assay, then 10 µg/mL of each sample (+IPTG or −IPTG) was treated with 1 µM FRET-TDM. After 4 h incubation in a 96 well plate at 37° C., fluorescence (Ex 488/Em 525) was measured using a Tecan F200 multimodal plate reader (FIG. 52). No change in fluorescence was observed between the FRET-TDM-only sample (blue) and the *E. coli* −IPTG+FRET−TDM sample (green), which was not induced to express TDMH. However, significant fluorescence turn-on was observed in the *E. coli* +IPTG+FRET−TDM sample (orange), which was induced to express TDMH by addition of IPTG.

Activation of FRET-TDM by TDM Hydrolase in *M. smegmatis* Lysate.

Figure 53:
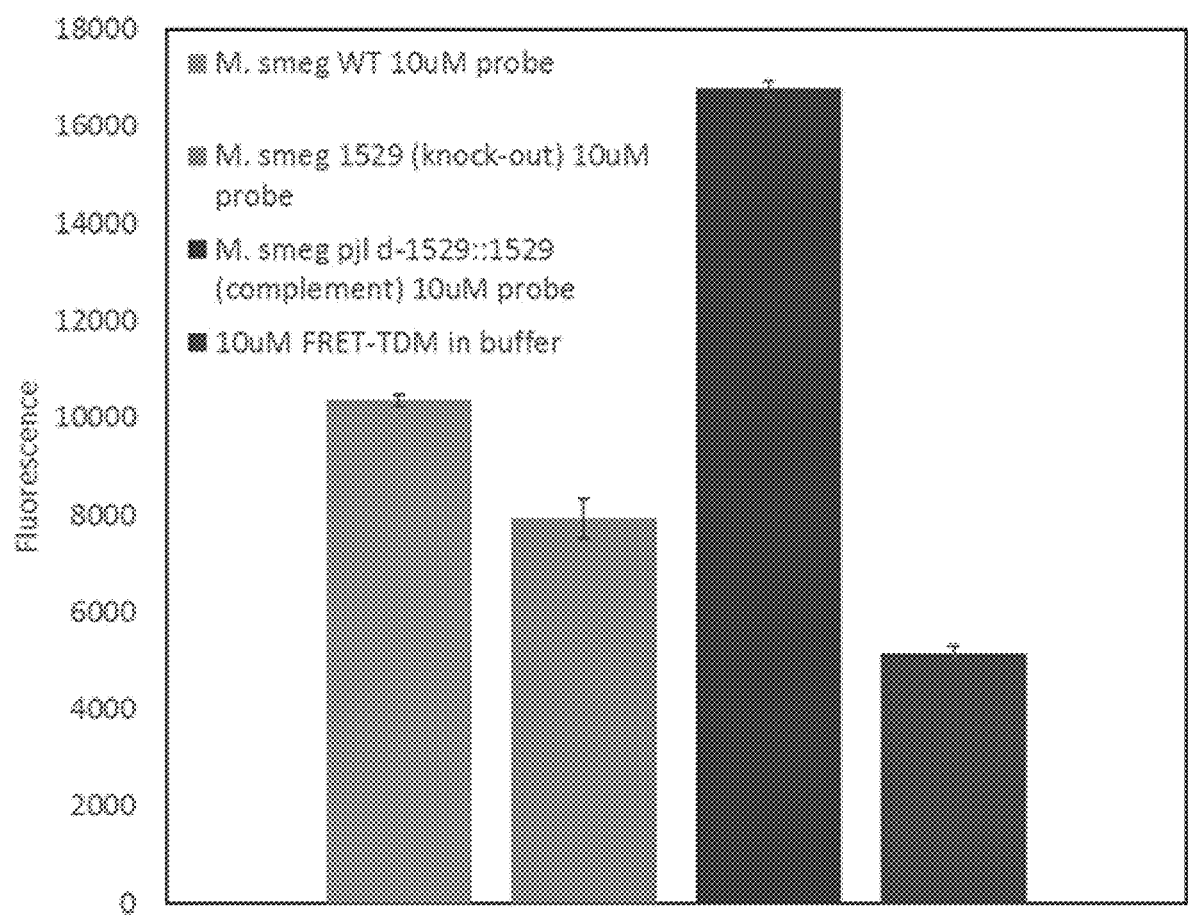
FIG. 53 shows a plot of fluorescence of 10 μM FRET-TDM by 10 μg/mL lysate from M. smegmatis (i) wild type, which expresses TDMH endogenously (orange); (ii) M. smegmatis ΔMSMEG_1529, which is a TDMH knock-out mutant (green); (iii) M. smegmatis ΔMSMEG_1529::MSMEG_1529, which is a complement strain with TDMH overexpression (blue); (iv) in buffer only (purple).

*M. smegmatis* is a mycobacterial species that, like the pathogen *M. tuberculosis*, naturally expresses TDMH. No other bacterial species are known to express the TDMH enzyme. To determine whether FRET-TDM is activated by endogenous TDMH in mycobacteria, *M. smegmatis* wild type, TDMH knock-out mutant, and TDMH-overexpression strains were grown in 7H9 medium at 37° C. to an optical density (600 nm) of approximately 1. The cells were pelleted, washed, and lysed into HEPES buffer (50 mM, pH 7.4). The protein concentrations of the lysates were assessed by Bradford assay, then 10 µg/mL of each sample was treated with 10 µM FRET-TDM. After 4 h incubation in a 96 well plate at 37° C., fluorescence (Ex 488/Em 525) was measured using a Tecan F200 multimodal plate reader (FIG. 53). Fluorescence turn-on was observed in all three strains versus the no-lysate control (purple). However, the significant decrease of signal in the knock-out mutant (green) compared to wild-type *M. smegmatis* indicates that endogenous levels of TDMH indeed activate FRET-TDM. Because fluorescence signal was not completely reduced to the control level in the knock-out mutant, it is likely that other mechanisms for FRET-TDM activation exist in *M. smegmatis* (it is notable that this is not the case in *E. coli*, as shown in FIG. 52). Finally, an *M. smegmatis* strain engineered to overexpress TDMH (blue) had very strong fluorescence compared to wild-type, showing that FRET-TDM activation can be dependent upon the level of TDMH.

Activation of FRET-TDM by TDM Hydrolase in Whole Cells of *M. smegmatis*.

Figure 54:
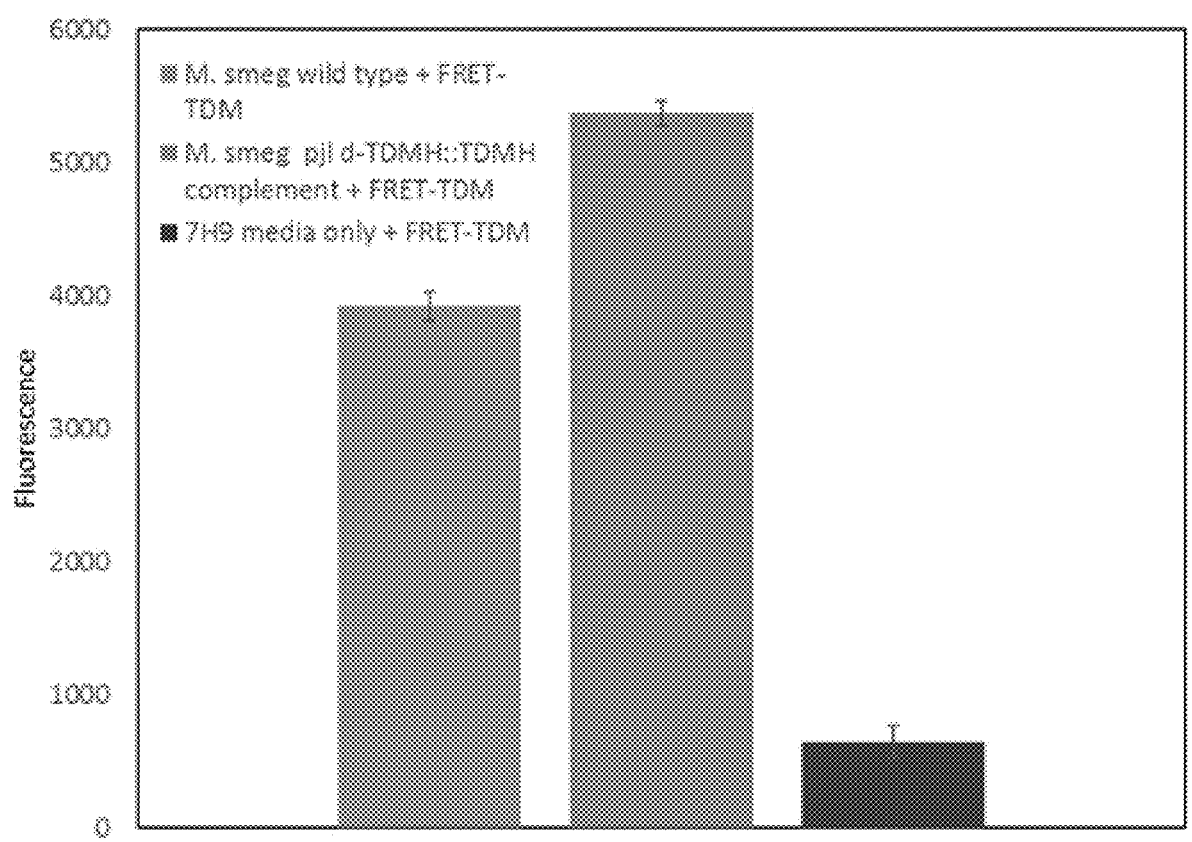
FIG. 54 shows a plot of fluorescence of 1 μM FRET-TDM by whole cells of M. smegmatis (i) wild type (orange); (ii) overexpression strain (green); and (iii) in 7H9 medium only as a no-cell control (blue).

To determine whether FRET-TDM is activated by endogenous TDMH in whole cells of mycobacteria, *M. smegmatis* wild type and TDMH-overexpression strains were cultured in 7H9 medium in the presence or absence of 1 µM FRET-TDM. After 4 h incubation in a 96 well plate at 37° C., cellular fluorescence (Ex 488/Em 525) was measured using a Tecan F200 multimodal plate reader (FIG. 54). Fluorescence turn-on was observed in both strains versus the no-cells control (blue) and elevated in the overexpression strain, indicating that TDMH-dependent FRET-TDM activation can be performed in whole cells.

The data indicate that FRET-TDM can be activated in a TDMH-dependent manner in complex samples (including lysates and whole, live cells). Given the specificity of TDMH to mycobacteria, this capability may serve as a method for the rapid, sensitive, and accurate diagnosis of mycobacterial infections, for instance by sputum smear microscopy. The lack of background signal in *E. coli* lysate further supports the specificity of FRET-TDM for mycobacteria. Improved specificity may be obtained by developing FRET-TDM compounds bearing acyl chains that more closely resemble mycolic acids (i.e., containing alpha branches with or without beta hydroxyl groups, and potentially other modifications that are known to occur in mycolic acids), as described in this application. Enhanced sensitivity may be obtained by developing FRET-TDM compounds with optimized fluorophore/quencher pairs and distances, as described in this application. A similar approach based on a FRET-based fluorogenic TMM substrate analogue targeting mycobacteria-specific Ag85 enzymes is also possible given the described findings on Ag85 specificity for TMM analogues described in this application.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:
1. A compound according to formula (II):

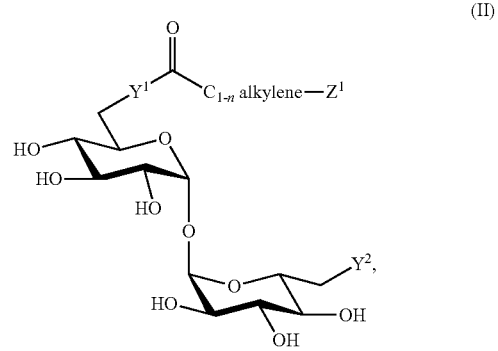

wherein
Y$^1$ is O or NH;
Y$^2$ is OC(O)C$_{1-n}$ alkylene-Z$^2$, or NHC(O)C$_{1-n}$ alkylene-Z$^2$;
Z$^1$ is a fluorophore;
Z$^2$ is a quencher of the fluorophore of Z$^1$; and
n is 0 to 50,
wherein C$_{1-n}$ alkylene is optionally substituted.
2. The compound of claim 1, wherein
Y$^1$ is O; and
Y$^2$ is OC(O)C$_{1-n}$ alkylene-Z$^2$.
3. The compound of claim 1, wherein the quencher comprises a dabcyl group.

4. The compound of claim 3, wherein the quencher is

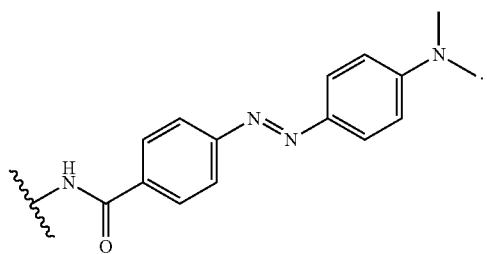 [SMILES: *NC(=O)c1ccc(/N=N/c2ccc(N(C)C)cc2)cc1]

5. The compound of claim 1, wherein Z' is a fluorophore selected from the group consisting of a fluorescein, xanthene, cyanine, naphthalene, coumarin, oxadiazole, pyrene, oxazine, acridine, arylmethine, tetrapyrrole, and quantum dot.

6. The compound of claim 5, wherein $Y^1$ is O; and $Y^2$ is $OC(O)C_{1-n}$ alkylene-$Z^2$.

7. The compound of claim 5, wherein Z' is a fluorescein.

8. The compound of claim 7, wherein $Z^1$ is

9. The compound of claim 5, wherein the quencher comprises a dabcyl group.

10. The compound of claim 9, wherein the quencher is

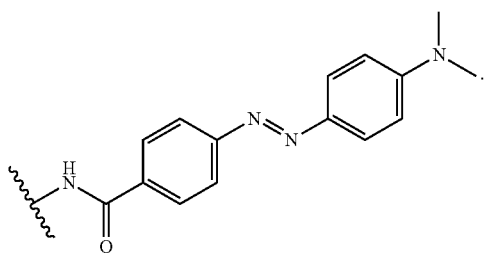 [SMILES: *NC(=O)c1ccc(/N=N/c2ccc(N(C)C)cc2)cc1]

11. The compound of claim 7, wherein the quencher comprises a dabcyl group.

12. The compound of claim 11, wherein the quencher is

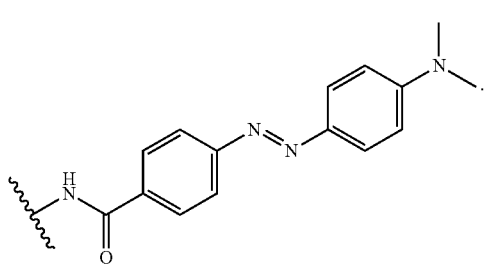 [SMILES: *NC(=O)c1ccc(/N=N/c2ccc(N(C)C)cc2)cc1]

13. The compound of claim 5 of formula

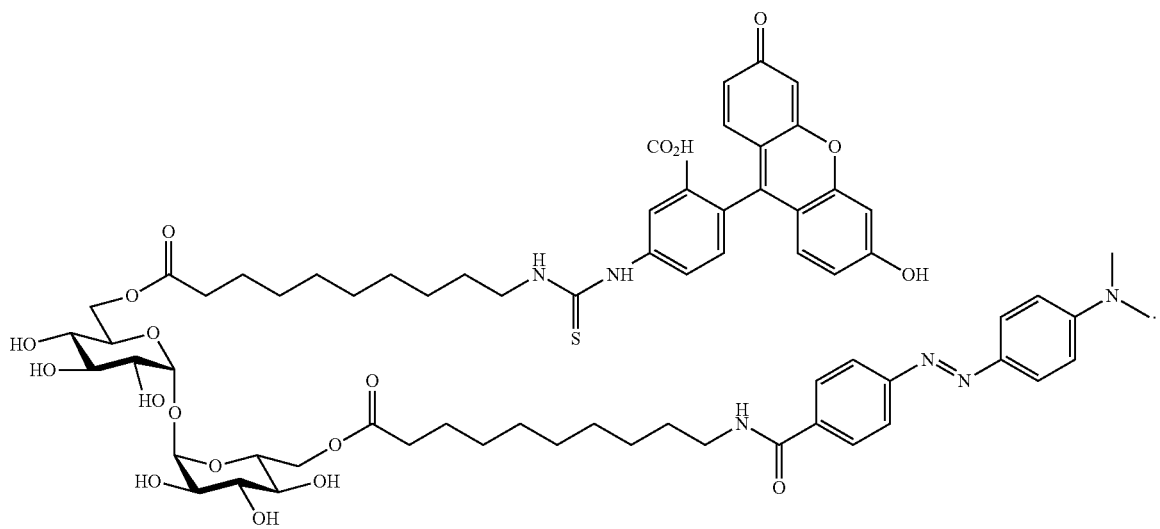

14. The compound of claim 1, wherein each $C_{1-n}$alkylene is a branched $C_{1-n}$alkylene optionally substituted with hydroxy.

15. The compound of claim 14, wherein the branched $C_{1-n}$alkylene has a branch at the alpha position.

16. The compound of claim 15, wherein the optional hydroxy substituent is attached to a carbon adjacent to the branch at the alpha position in the branched $C_{1-n}$alkylene.

17. A compound according to formula (II):

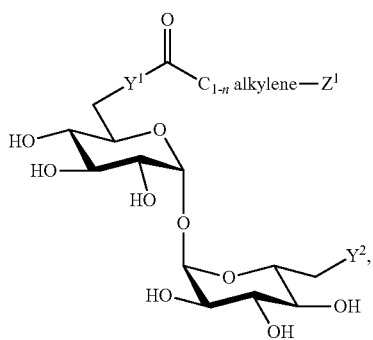

(II)

wherein $Y^1$ is O or NH;

$Y^2$ is OC(O)$C_{1-n}$ alkylene-$Z^2$, or NHC(O)$C_{1-n}$ alkylene-$Z^2$;

$Z^1$ is a fluorophore;

$Z^2$ is a quencher; and n is 0 to 50, wherein $C_{1-n}$ alkylene is optionally substituted and the compound acts as a fluorescence resonance energy transfer (FRET) probe that is detectable after undergoing cellular metabolism.

18. A method of detecting mycobacteria comprising:

a. contacting a sample with a compound according to claim 1;

b. detecting the labeled mycobacteria.

19. The method of claim 18, wherein the sample is sputum, cerebrospinal fluid, pericardial fluid, synovial fluid, ascitic fluid, blood, bone marrow, urine, feces, or a cell.

20. The method of claim 18, wherein the mycobacteria is Mycobacteria tuberculosis.

* * * * *